(12) United States Patent
Davidson et al.

(10) Patent No.: US 6,470,222 B1
(45) Date of Patent: Oct. 22, 2002

(54) DENTAL DELIVERY SYSTEM

(75) Inventors: Willard S. Davidson; Cheryl L. Davidson, both of Wabasha, MN (US)

(73) Assignee: Rockford Dental Mfg. Co., Bend, OR (US)

( * ) Notice: Subject to any disclaimer, the term of this patent is extended or adjusted under 35 U.S.C. 154(b) by 0 days.

(21) Appl. No.: 09/486,459

(22) PCT Filed: Aug. 26, 1997

(86) PCT No.: PCT/US97/15005

§ 371 (c)(1),
(2), (4) Date: Jul. 26, 2000

(87) PCT Pub. No.: WO99/10828

PCT Pub. Date: Mar. 4, 1999

(51) Int. Cl.[7] .............................................. G05B 19/18
(52) U.S. Cl. ................................ 700/2; 433/98; 433/27
(58) Field of Search ............................... 700/2, 19, 20; 433/25, 27, 101, 229, 98

(56) References Cited

U.S. PATENT DOCUMENTS

| | | | | |
|---|---|---|---|---|
| 3,702,940 A | * | 11/1972 | Stewart | 307/923 |
| 3,886,660 A | * | 6/1975 | Thornton, Jr. et al. | 32/22 |
| 4,180,812 A | * | 12/1979 | Kaltenbach et al. | 340/706 |
| 4,538,988 A | | 9/1985 | Henrichsen et al. | 433/84 |
| 4,676,750 A | * | 6/1987 | Mason | 433/101 |
| 5,017,136 A | * | 5/1991 | Gatti | 433/98 |
| 5,201,899 A | * | 4/1993 | Austin, Jr. et al. | 433/98 |
| 5,538,423 A | | 7/1996 | Coss et al. | 433/27 |
| 5,931,669 A | * | 8/1999 | Fornoff et al. | 433/28 |
| 5,947,729 A | * | 9/1999 | Bell | 433/98 |

OTHER PUBLICATIONS

International Search Report dated Dec. 12, 1997, (PCT/US97/15005).

* cited by examiner

*Primary Examiner*—Thomas Black
*Assistant Examiner*—Ronald D Hartman, Jr.
(74) *Attorney, Agent, or Firm*—Trask Britt, PC

(57) ABSTRACT

A distributed intelligence system for controlling a plurality of groups and equipment for use in dentistry is disclosed wherein the system comprises four separate micro controllers; each micro controller contains its own predetermined routines and a first micro controller being located within control circuitry wherein the control circuitry generates control signals for a first group of tools or equipment, a second micro controller being located within foot switches wherein the foot switches generate control signals for a second group of tools or equipment, a third micro controller located within a control console wherein the control console generates control signals for a third group of tools or equipment and a forth micro controller being located within a power supply wherein the power supply generates control signals for a forth group of tools or equipment. The micro controllers are all interconnected by a wire cable and communicate with one another using a serial communication bus protocol.

9 Claims, 40 Drawing Sheets

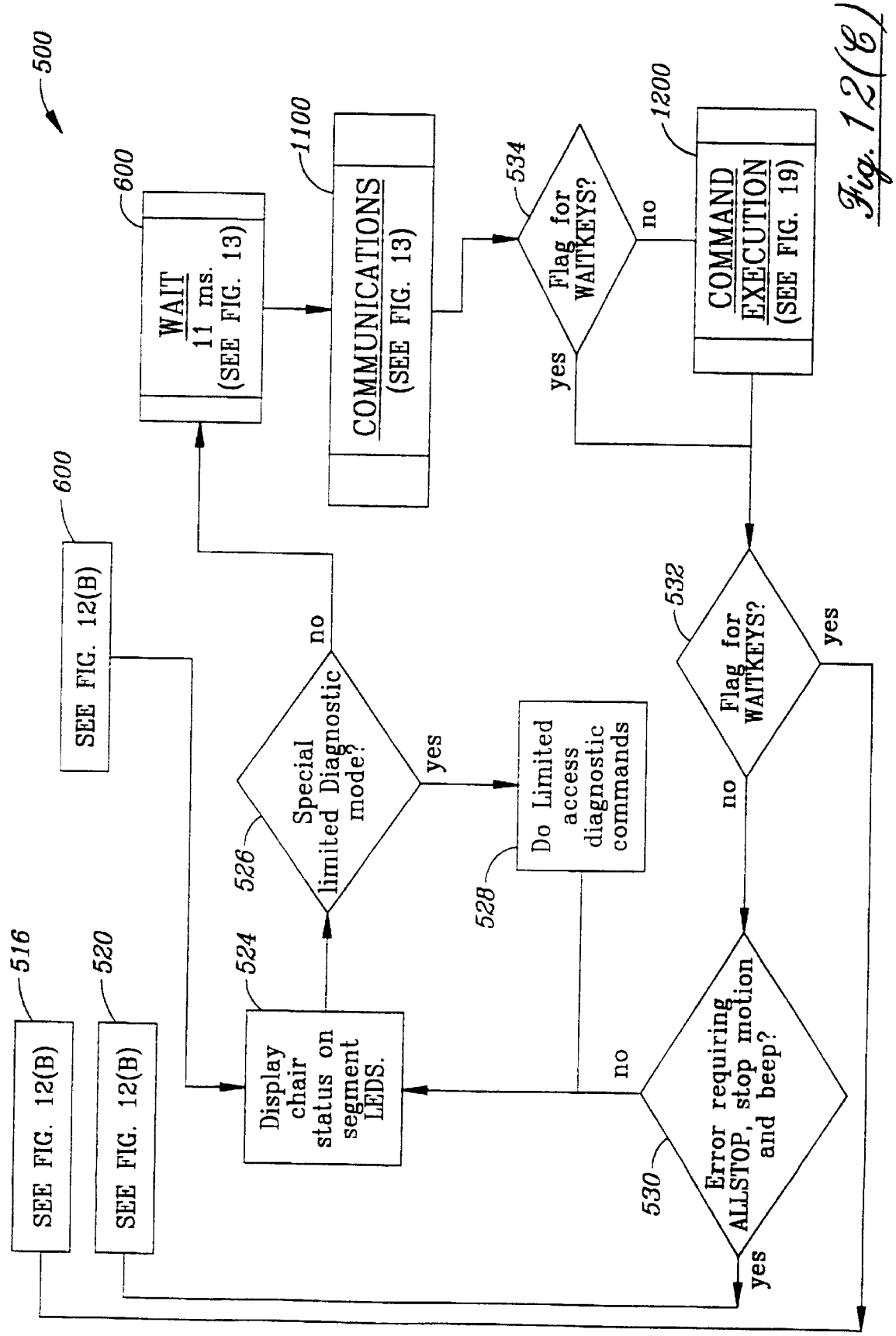

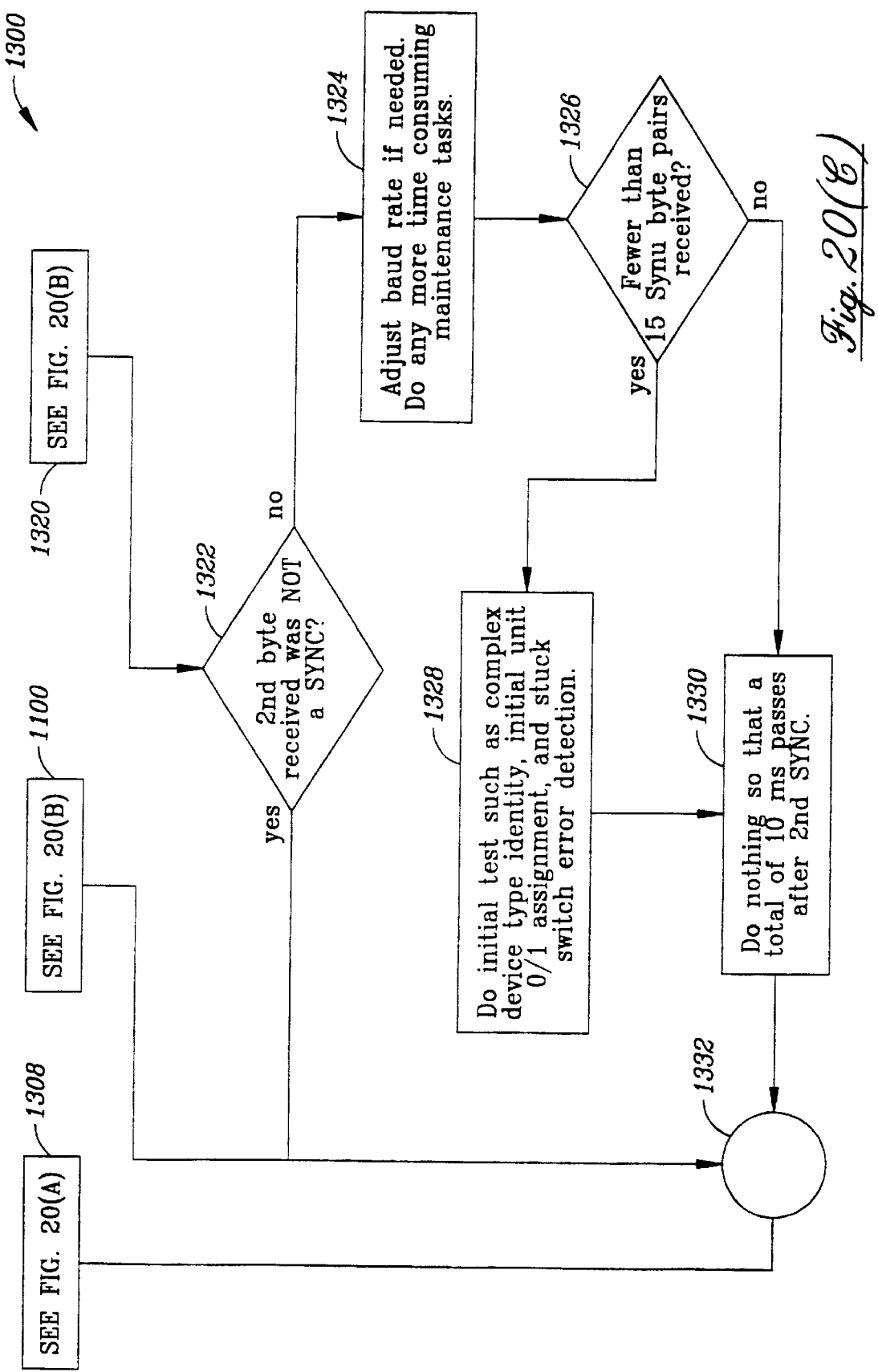

DENTAL DELIVERY SYSTEM

FIELD OF THE INVENTION

This invention relates generally to a system for controlling electrical, mechanical and hydraulic tools and equipment and, more particularly, to a system having distributed intelligence provided by a plurality of microcontrollers each having predetermined control and diagnostic routines for controlling tools and equipment used in dentistry.

BACKGROUND OF THE INVENTION

The practice of dentistry for the prevention, diagnosis and treatment of diseases, injuries and malfunctions of the teeth, jaw and mouth has made continuous advancements over the years with the patient being the primary beneficiary of such advancements. The tools used in dentistry, such as high-speed dental drills, have been improved and these advancements coupled with improvements in the equipment, such as the dental chair, have created an environment in which the patient is more relaxed, thereby, allowing the dentist to more effectively practice his/her skills.

Dentistry being devoted to the treatment of patients in the general population, encounters regulations which the executive authority feel necessary so as to protect the public at large. These regulations are revised and/or added to in order to accommodate ever increasing changes in public health, such as the treatment of Aids patients. Dentistry, in particular, its tools and equipment must be able to accommodate changes so as to accommodate the regulatory pressures that may evolve from time-to-time allowing the safe guarding of the overall health of the public at large.

The practice of dentistry and, more particularly, its tools and equipment, need to be constantly analyzed and updated to accommodate technical advancements which commonly occur in the form of computerized equipment. The computerized equipment itself needs to be constantly analyzed to safeguard its operation and also to be properly maintained by self-checking, built-in diagnostic routines embedded in the computerized equipment. Furthermore, the constantly advancing technology must be anticipated in the tools and equipment of dentistry such that existing tools and equipment need to have provisions to accommodate future devices having improvements thereof.

OBJECTS OF THE INVENTION

It is a primary object of the present invention to provide a system for controlling tools and equipment used in dentistry that incorporate computerized devices, such as microcontrollers, that not only control the operation of the dental tools and equipment, but also provide self-checking and diagnostic routines that automatically detect malfunctions in the tool and/or dental equipment, thereby, safe guarding the patient receiving the dental care.

It is a further object of the present invention to provide a distributed intelligence system, having processing capabilities, that is provided by separate microprocessors to control separate groups of tools and/or equipment.

Another object of the present invention is to provide a distributed intelligence system for controlling tools and equipment used for dental purposes that is connected together by a communication network such as that provided by a serial communication protocol so as to reduce the interconnecting cabling therebetween to a minimum.

Furthermore, it is an object of the present invention to provide a system for controlling tools and equipment used in dentistry which has control switches that are made readily available to the dentist and also has means that allow the patient to be oriented into a convenient and efficient position with respect to allowing the dentist to effectively utilize his/her skills.

According to the present invention, the foregoing and additional objects are attained by a distributed intelligence system for controlling a plurality of groups of tools and equipment used in dentistry and comprising control circuitry, one or more foot switches, a control console, power supply means, and cabling means. The control circuitry generates first control signals that are applied to a first group of tools and equipment and receives first status signals from the first group of tools and equipment. The control circuitry includes a first microcontroller containing predetermined routines for the generation of the first control signals and for being responsive to the first status signals. The control circuitry has protocol means for accommodating a serial communication bus. The one or more switches generate second control signals that are applied to a second group of tools and equipment and receive second status signals from the second group of tools and equipment. The one or more foot switches include a second microcontroller containing predetermined routines for the generation of the second control signals and for being responsive to the second status signals. The one or more switches have protocol means for accommodating the serial communication bus. The control console generates third control signals applied to a third group of tools and equipment and receives third status signals from the third group of tools and equipment. The control console includes a third microcontroller containing predetermined routines for the generation of the third control signals and for being responsive to the third status signals. The control console has protocol means for accommodating the serial communication bus. The power supply means is connected to the control circuitry, to the one or more foot switches, and to the control console. The power supply means generates fourth control signals applied to a fourth group of tools and equipment and receives fourth status signals for the fourth group of tools and equipment. The power supply means includes a fourth microcontroller containing predetermined routines for the generation of the fourth control signal and for being responsive to the fourth status signals. The power supply means has protocol means for accommodating the serial communication bus. The cable means interconnects the protocol means of the control circuitry, of the one or more foot switches, of the control console, and of the power supply means.

DETAILED DESCRIPTION OF THE PREFERRED EMBODIMENTS

Figure 1:
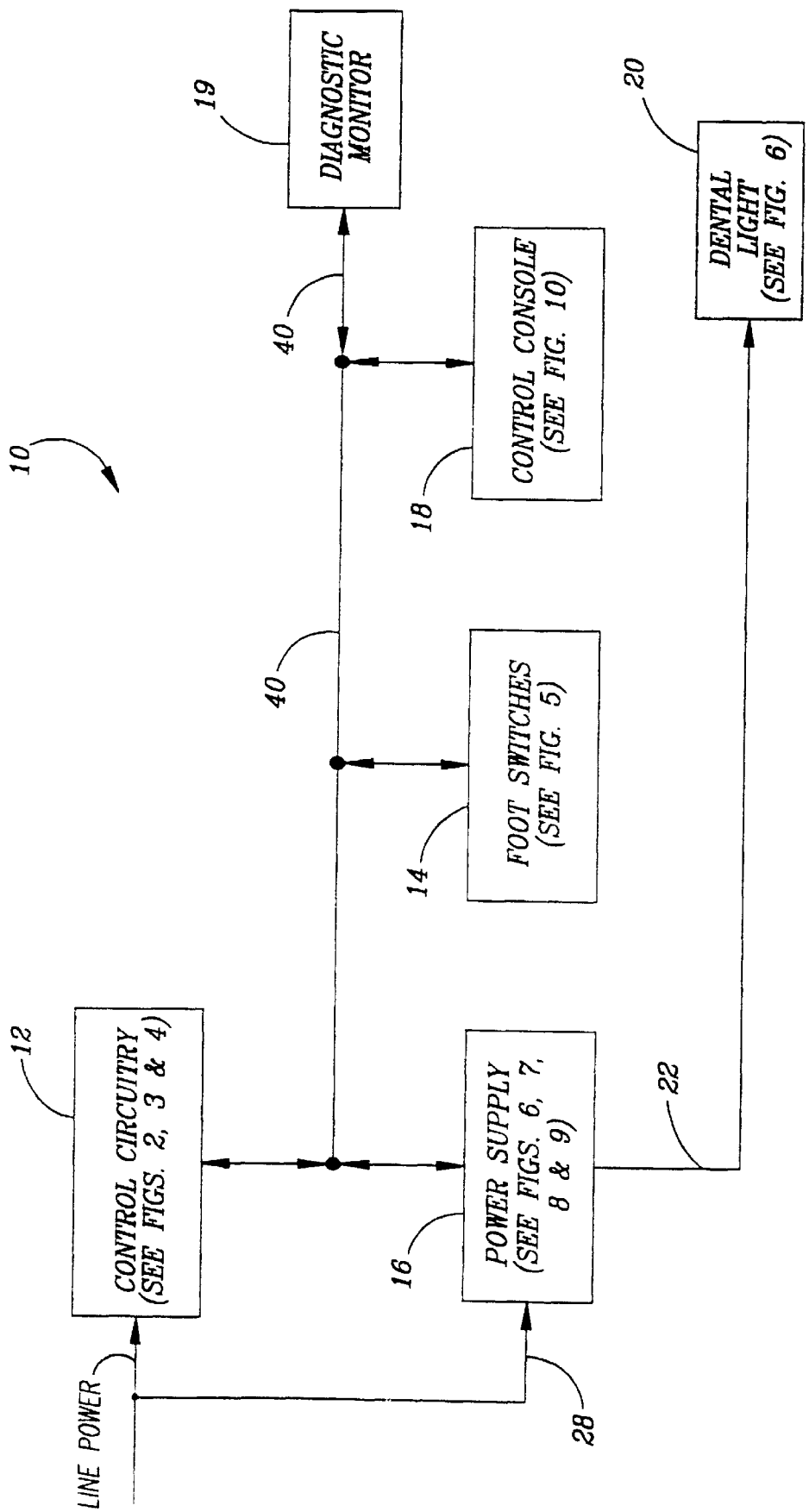
FIG. 1 is a block diagram of the distributed intelligence system 10.

With reference to the drawings, wherein the same reference numbers indicate the same elements throughout, there is shown in FIG. 1 a block diagram of the distributed intelligence system 10 for controlling groups of tools and equipment for dentistry. The distributed intelligence system 10 comprises control circuitry 12, foot switches 14, a power supply 16, and a control console 18 all of which include a control microprocessor, sometimes referred to as a microcontroller, and control procedures along with self-checking and diagnostic procedures.

In general, the control circuitry 12 includes a first microcontroller containing predetermined routines for the generation of the first control signals that are applied to a first group of tools and equipment used in dentistry, and which first microcontroller is responsive to first status signals provided by the first group of dental tools and equipment. The foot switches 14 include a second microcontroller containing predetermined routines for the generation of second control signals applied to a second group of tools and equipment used in dentistry, and which second microcontroller is responsible to second status signals provided by the second group of dental tools and equipment. The control console 18 includes a third microcontroller containing predetermined routines for the generation of third control signals routed to a third group of tools and equipment used in dentistry, and which third microcontroller is responsive to third status signals from the third group of dental tools and equipment. The power supply 16 includes a fourth microprocessor for generating fourth control signals applied to a fourth group of tools and equipment used in dentistry and which fourth microcontroller is responsive to fourth status signals generated by the fourth group of dental tools and equipment. The first, second, third and fourth microprocessors are interrelated to the first, second, third and fourth groups of equipment for the sake of the clarity of the description therebetween and other arrangements thereof are contemplated by the practice of the present invention. The power supply 16 and the control console 18 provide signals to a dental light 20, via signal path 22. A diagnostic monitor 19 provides power to all the equipment of FIG. 1 for diagnostic and back-up power conditions in a manner to be described. The diagnostic monitor 19 accesses all of the equipment of FIG. 1 for diagnostic, maintenance and manufacturing purposes all to be described hereinafter.

Figure 2:
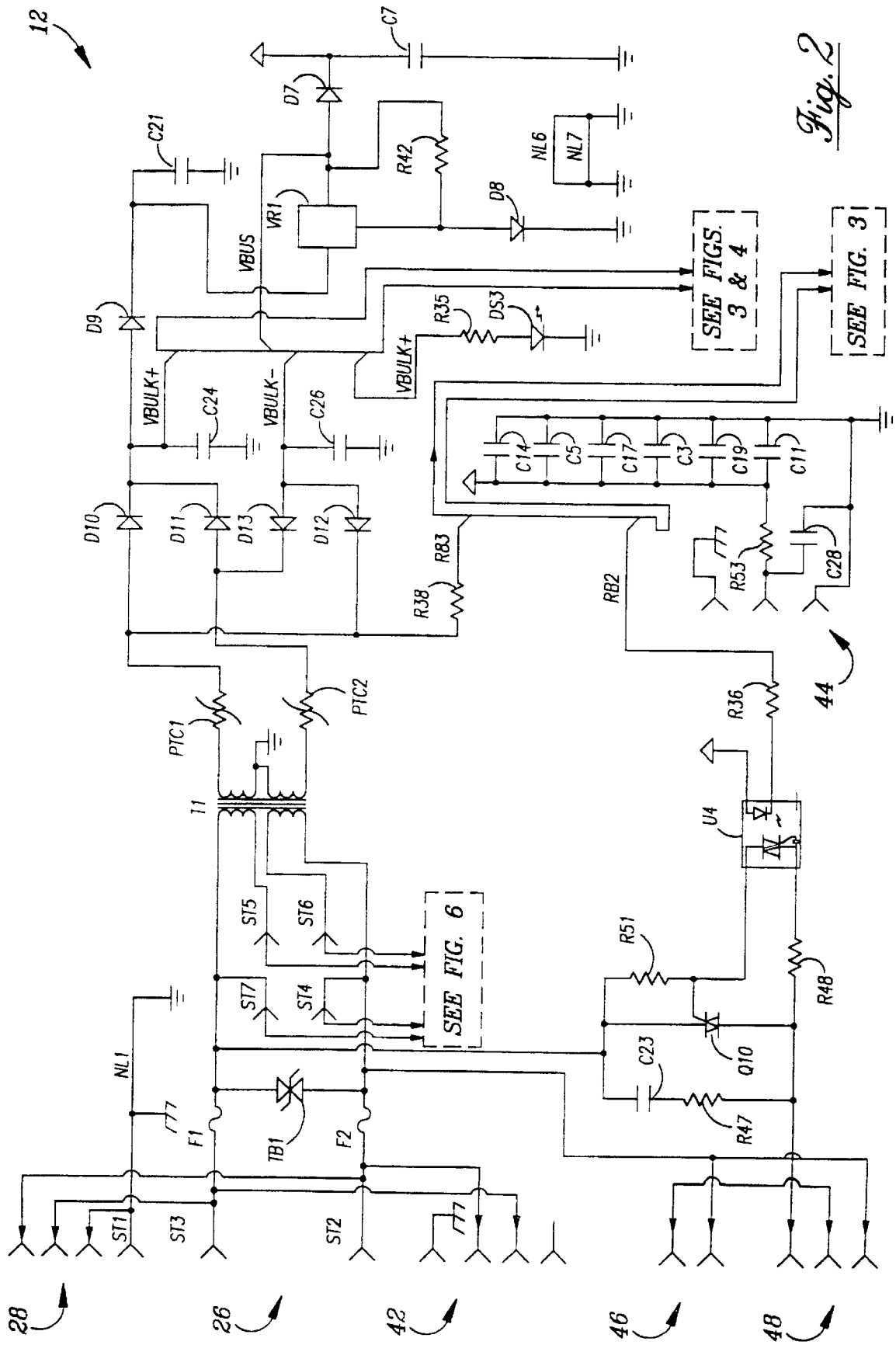
FIGS. 2, 3 and 4 accumulatively illustrate the details of the control circuitry of FIG. 1.
Figure 3:
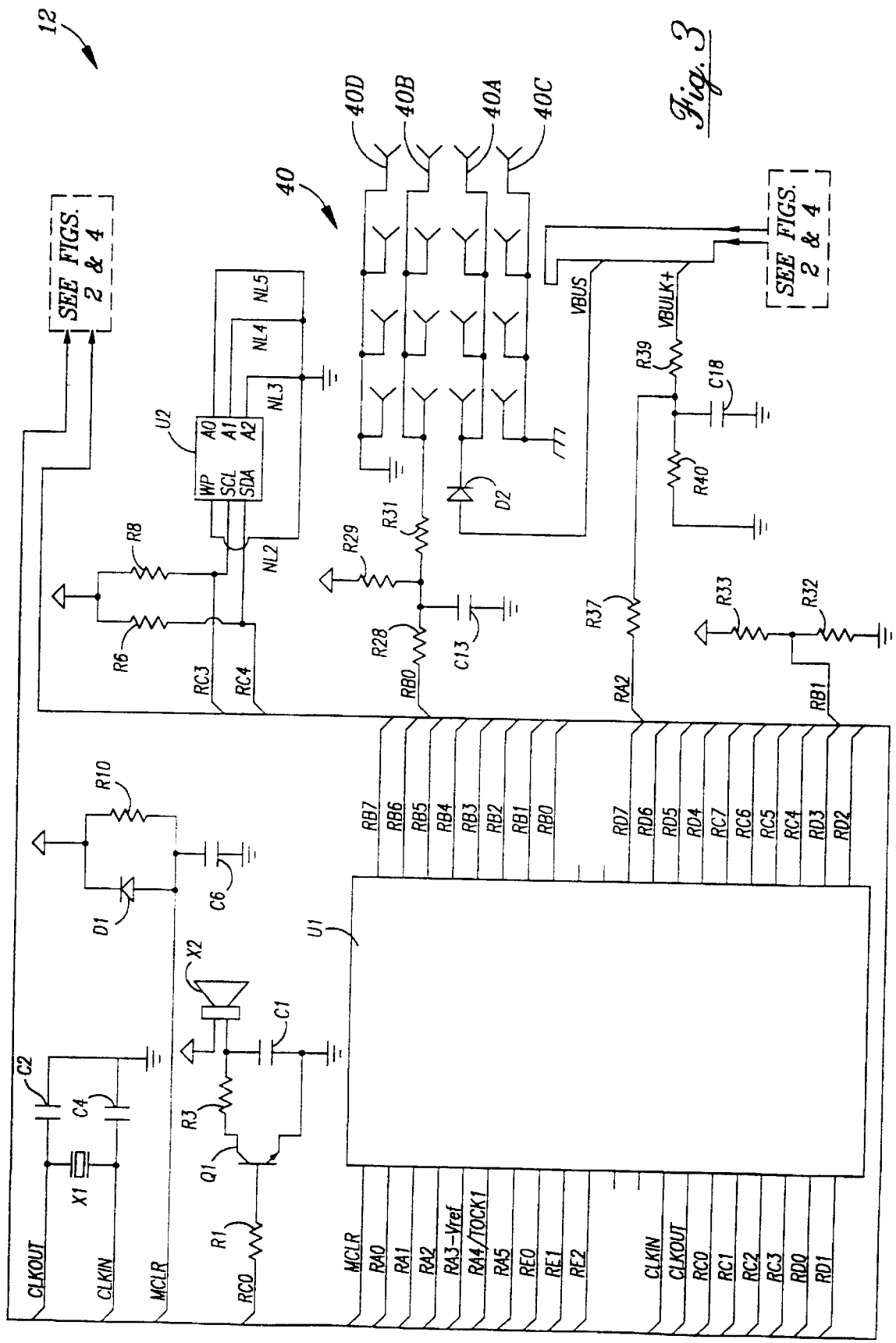
Figure 4:
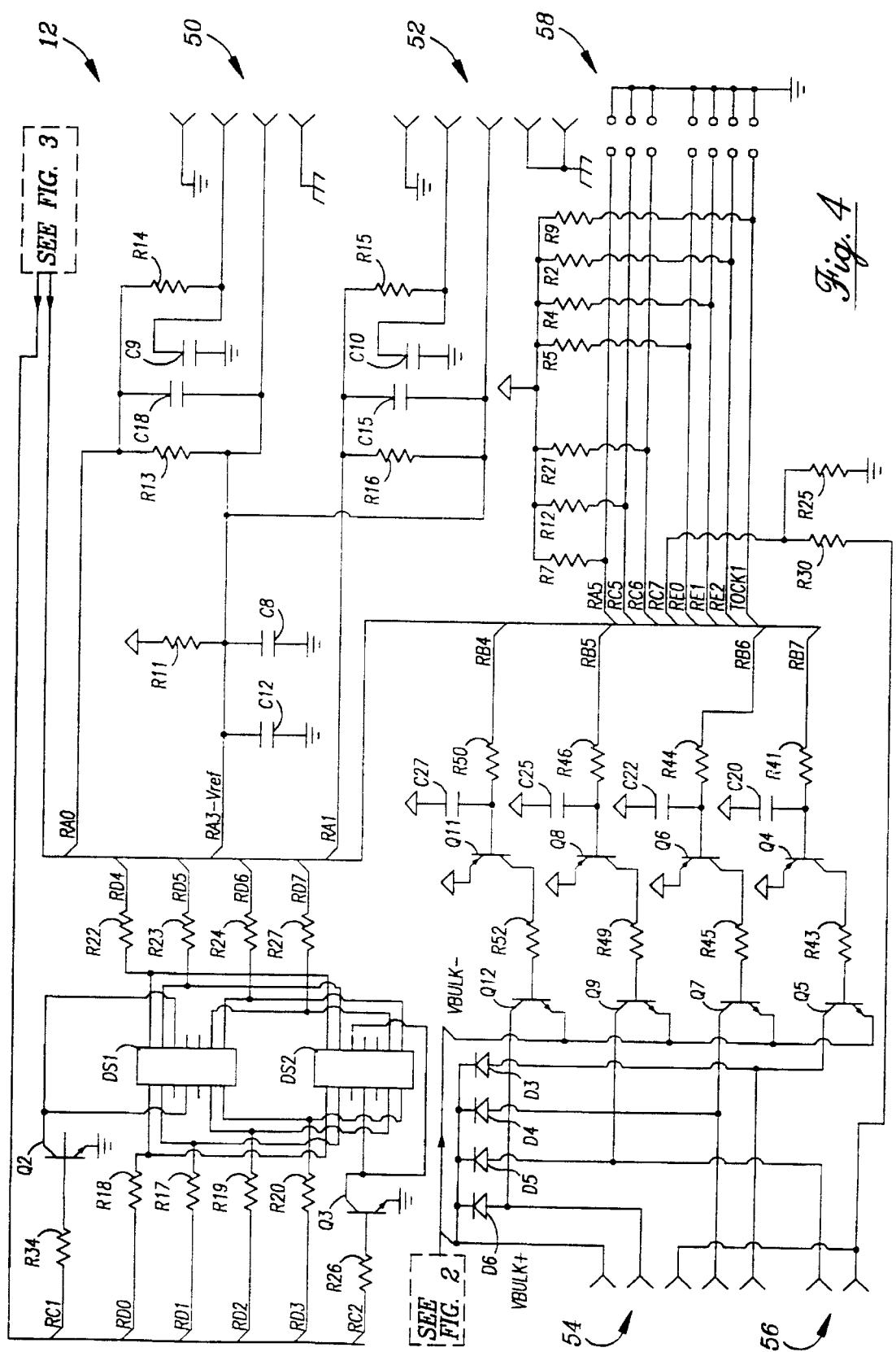

The control circuitry 12, and the power supply 16 receive excitation by way of signal paths 26 and 28 respectively. The control circuitry 12, the power supply 16, foot switches 14, and the control console 18, more particularly, the microcontrollers 1, 2, 3, and 4, respectively, each have protocol means for accommodating a serial communication bus 40 all of which are to be described hereinafter with reference to FIGS. 11–26. Further, as shown in FIG. 1, the diagnostic monitor 19 is connected to the serial communication bus 40 and has protocol means so as to communicate with the microcontrollers 1, 2, 3 and 4. The protocol means for communicating with a serial communication bus, such as bus 40, are known in the art. The serial communication bus 40 may also be referred to herein as the dental bus, especially with reference to FIGS. 11–26. The details of the control circuitry 12 is illustrated in FIGS. 2, 3, and 4 comprised of a plurality of elements having typical values or being of a particular type given in Table 1.

TABLE 1

| ELEMENT | COMPONENT VALUE/TYPE |
|---------|----------------------|
| C23 | 0.02 µF |
| C21 | 1000 µF |
| C24 | 220 µF |
| C26 | 220 µF |
| C2 | 22 PF |
| C4 | 22 PF |
| C1 | 0.1 µF |
| C3 | 0.1 µF |
| C5 | 0.1 µF |
| C6 | 0.1 µF |
| C9 | 0.1 µF |
| C10 | 0.1 µF |
| C12 | 0.1 µF |
| C14 | 0.1 µF |
| C17 | 0.1 µF |
| C18 | 0.1 µF |
| C20 | 0.1 µF |
| C22 | 0.1 µF |
| C25 | 0.1 µF |
| C27 | 0.1 µF |
| C28 | 0.1 µF |
| C7 | 4.7 µF 25V |
| C8 | 4.7 µF 25V |
| C11 | 4.7 µF 25V |
| C15 | 4.7 µF 25V |
| C16 | 4.7 µF 25V |
| C19 | 4.7 µF 25V |
| C13 | 0.001 µF |
| NL2 | CUTTABLE NET LINK |
| NL3 | CUTTABLE NET LINK |

TABLE 1-continued

| ELEMENT | COMPONENT VALUE/TYPE |
| --- | --- |
| NL4 | CUTTABLE NET LINK |
| NL5 | CUTTABLE NET LINK |
| NL6 | CUTTABLE NET LINK |
| NL7 | CUTTABLE NET LINK |
| NL1 | ALL LAYER NET LINK |
| F1 | 12A FUSE |
| F2 | 12A FUSE |
| HS1 | Heat Sink TO-220 |
| T1 | Transformer Tie-Wrap PREM MAGNETICS SPW614d TRANSFO |
| X1 | CRYSTAL, 10 MHZ |
| U1 | PIC 16C74A 10 MHZ (HS) (OTP) |
| U2 | CMOS SERIAL EEPROM |
| U4 | OPT. COUPLED TRIAC DRIVER, O C |
| R3 | 10 Ohm |
| R11 | 100 Ohm |
| R1 | 1K Ohm |
| R14 | 1K Ohm |
| R15 | 1K Ohm |
| R26 | 1K Ohm |
| R34 | 1K Ohm |
| R37 | 1K Ohm |
| R43 | 1K Ohm |
| R45 | 1K Ohm |
| R49 | 1K Ohm |
| R51 | 1K Ohm |
| R52 | 1K Ohm |
| R6 | 10K Ohm |
| R8 | 10K Ohm |
| R10 | 10K Ohm |
| R29 | 10K Ohm |
| R35 | 10K Ohm |
| R40 | 10K Ohm |
| R42 | 10K Ohm |
| R44 | 10K Ohm |
| R46 | 10K Ohm |
| R50 | 10K Ohm |
| R2 | 100K Ohm |
| R4 | 100K Ohm |
| R5 | 100K Ohm |
| R7 | 100K Ohm |
| R9 | 100K Ohm |
| R12 | 100K Ohm |
| R13 | 100K Ohm |
| R16 | 100K Ohm |
| R21 | 100K Ohm |
| R25 | 100K Ohm |
| R30 | 100K Ohm |
| R32 | 100K Ohm |
| R33 | 100K Ohm |
| R38 | 100K Ohm |
| R28 | 220 Ohm |
| R39 | 22K Ohm |
| R17 | 330 Ohm |
| R18 | 330 Ohm |
| R19 | 330 Ohm |
| R20 | 330 Ohm |
| R22 | 330 Ohm |
| R23 | 330 Ohm |
| R24 | 330 Ohm |
| R27 | 330 Ohm |
| R31 | 330 Ohm |
| R36 | 330 Ohm |
| R48 | 330 Ohm |
| R53 | 330 Ohm |
| R47 | 47 Ohm |
| Q1 | LOW POWER NPN TPANSISTOR |
| Q2 | LOW POWER NPN TRRNSISTOR |
| Q3 | LOW POWER NPN TRANSISTOR |
| Q4 | LOW POWER PNP TRANSISTOR |
| Q6 | LOW POWER PNP TRANSISTOR |
| Q8 | LOW POWER PNP TRANSISTOR |
| Q11 | LOW POWER PNP TRANSISTOR |
| D2 | POWER DIODE |
| D3 | POWER DIODE |
| D4 | POWER DIODE |
| D5 | POWER DIODE |

TABLE 1-continued

| ELEMENT | COMPONENT VALUE/TYPE |
| --- | --- |
| D6 | POWER DIODE |
| D7 | POWER DIODE |
| D8 | POWER DIODE |
| D9 | POWER DIODE |
| D10 | POWER DIODE |
| D11 | POWER DIODE |
| D12 | POWER DIODE |
| D13 | POWER DIODE |
| D1 | SIGNAL DIODE |
| DS1 | 7 SEGMENT LED, MAN74A |
| DS2 | 7 SEGMENT LED, MAN74A |
| DS3 | 7 SEGMENT LED, MAN74A |
| Q10 | 400V TRIAC (STEP BASE) |
| TB1 | 470 VOLT SURGE SUPPRESSOR |
| PTC1 | 1.35A PTC THERMISTOR |
| PTC2 | 1.35A PTC THERMISTOR |
| Q5 | TIP 110 NPN MEDIUM PQWER TRANS |
| Q7 | TIP 110 NPN MEDIUM POWER TRANS |
| Q9 | TIP 110 NPN MEDIUM POWER TRANS |
| Q12 | TIP 110 NPN MEDIUM POWER TRANS |
| VR1 | TIP 110 NPN MEDIUM POWER TRANS |

FIG. 2 illustrates the power excitation path 26 as comprising terminals ST1, ST2, and ST3 and which terminals are shared by power excitation path 28 that is routed to the power supply 16 as seen in FIG. 1. FIG. 2 further illustrates power excitation paths 42 and 44 that respectively carry auxiliary line power and suitable (+5V) excitation for light emitting devices (LED) utilized by the control circuitry 12. Further, FIG. 2 illustrates connectors 46 and 48 that respectively route the excitation to a first group of tools and equipment used in dentistry such as a pump and a capacitive motor for the dental equipment. As will be further described, the distributed intelligence system 10 deals with first, second, third and fourth groups of dental tools and equipment, but the invention is not limited to such a characterization because the groups may vary in number from 1 to n.

FIG. 2 primarily illustrates the power circuits for the control circuitry 12 comprising a transformer-rectifier-filter arrangement. The transformer-rectifier-filter arrangement comprises a voltage regulator VRI that develops a plurality of voltages VBULK+, VBULK− and VBUS voltages to be further described with reference to FIGS. 3 and 4. FIG. 3 further illustrates an optical coupling device U4 controlled by a signal designated as RB2 and which may be further described with reference to the microprocessor U1 illustrated in FIG. 3.

FIG. 3 illustrates the first microprocessor U1 as having signal designations, such as RB2, in which signals are routed throughout FIGS. 2, 3 and 4. The operation of the first microprocessor U1 including its servicing of the first group of tools and equipment of dentistry along with its diagnostic self-checking capability will be further described hereinafter.

The first microcontroller U1 communicates with the second, third and fourth microcontrollers by way of the serial communication bus 40 shown in FIG. 3 as comprising three conductors 40A, 40B, and 40C and preferably comprising a fourth conductor 40D. The conductors 40A, 40B, 40C and 40D respectively carry power excitation in the form of the voltage VBUS, data contained in communication signals such as signal RBO output of the first microcontroller U1, a return path for power excitation (VBUS) and the data (RBO), and a frame ground of the associated device, such as the control circuitry 12. The first microcontroller U1 is activated in response to the operation of the watch dog timer U2, to be further described, via signals RC3 and RC4. The first microcontroller U1 receives its clock signals, known in the art, from the operation of crystal X1 and capacitor C2 and C4 arranged as shown in FIG. 3. The input and output signals for the first microprocessor U1 are further routed to the circuitry of FIG. 4.

FIG. 4 illustrates the control signals RC1, RD0, RD1, RD2, RD3, RC2, RD4, RD5, RD6, RD7 as being applied to the display counters DS1 and DS2 (to be further described hereinafter) by way of serial resistors and/or transistor switches. FIG. 4 further illustrates the control signals RA0, RA3-Vref, and RA1 as being applied to connectors 50 and 52 via serial and parallel resistors and capacitors arranged and shown in FIG. 4. Connections 50 and 52 are inputs that are used to sense the position of the primary piece of equipment of the present invention, that is, the dental chair. The connectors 50 and 52 are routed to the first group of dental tools and equipment. Furthermore, FIG. 4 illustrates the control signals RB4, RB5, RB6 and RB7 as being routed to connectors 54 and 56 by way of resistors and capacitors serially arranged with transistor switches as shown in FIG. 4. The connectors 54 and 56 are routed to the first group of dental tools and equipment related to the present invention. FIG. 4 further illustrates an array 58 having pins whose connections to ground are selected by optional control jumpers and which pins respectively carry signals RA5, RC5, RC6, RC7, RE0, RE1, RE2 and TOCK1. The purpose of the optional control jumpers is to allow factory and service personnel to configure the operation of the system 10 of FIG. 1. The microprocessor on the main control board 12 senses the presence or absence of these jumpers to make minor modifications to its operational control flow. For example, one of these jumpers needs to be present for mechanical limit setting to occur. The first microcontroller U1 communicates, via the serial communication path 40, with the foot switches 14 that may be fully described with reference to FIG. 5 showing a plurality of elements having a typical value or being of a type as given in Table 2.

TABLE 2

| ELEMENT | COMPONENT VALUE/TYPE |
|---------|----------------------|
| C101 | 22 pf |
| C102 | 22 pf |
| C103 | 0.1 μF |
| C105 | 0.1 μF |
| C107 | 0.1 μF |
| C106 | 4.7 μF |
| C104 | 0.001 μF |
| NL101 | CUTTABLE NET LINK |
| SW101 | C&K switch |
| X101 | CRYSTAL, 10 MHZ |
| U101 | PIC 16C54A 10 MHZ (XT) (OTP) |
| R107 | 1K Ohm |
| R109 | 1K Ohm |
| R110 | 1K Ohm |
| R111 | 1K Ohm |
| R112 | 1K Ohm |
| R113 | 1K Ohm |
| R104 | 10K Ohm |
| R101 | 100K Ohm |
| R105 | 100K Ohm |
| R106 | 100K Ohm |
| R108 | 100K Ohm |
| R102 | 220 Ohm |
| R103 | 330 Ohm |
| D101 | POWER DIODE |
| D102 | SIGNAL DIODE |

Figure 5:
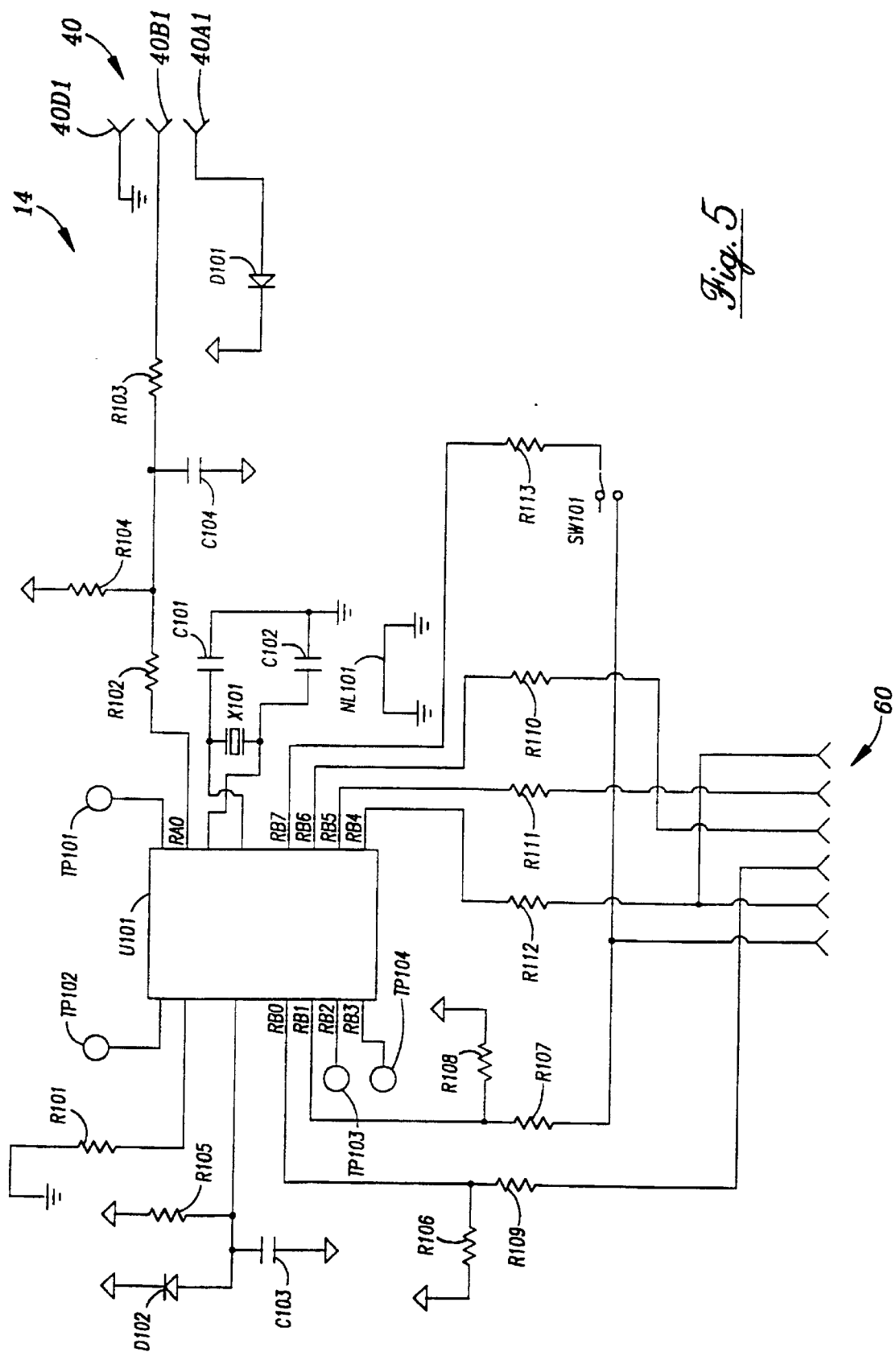
FIG. 5 illustrates the details of the foot switches of FIG. 1.

FIG. 5 illustrates a second microprocessor U101 as having the control signal RA0 which carries data on the data conductor shown as 40B1 of the serial communication bus 40 used to interconnect the foot switches 14 to the other equipment of the distributed intelligence system 10. The communication bus 40 also carries the power (VBUS) conductor 40A1 and the frame ground on conductor 40D1. The operation of the second microcontroller U101 is to be further describer hereinafter. The second microcontroller U101 provides control signals RB0, RB1, RB4, RB5, RB6 and RB7 that are routed to foot switches, via connector 60, for controlling the dental tools and equipment related to the second group thereof that are applied thereto by the resistor paths, such as resistors R106 and R109 for signal RB0 as shown in FIG. 5. The control signal RB0, RB1, RB4, RB5, RB6 and RB7 are actually connected to operator actuated switches and one of the primary purposes of the logic of FIG. 5 is to report the status of these switches to the control circuitry 12 of FIGS. 2–4. The control signal RB7 also passes through switch SW101 (learn) to be further described hereinafter. The second microprocessor U101, via control signal RA0 and the serial communication path 40, communicates with the power supply 16 illustrated in FIGS. 6, 7, 8 and 9 and comprised of elements having a typical value or being of a type as given in Table 3.

TABLE 3

| ELEMENT | COMPONENT VALUE/TYPE |
|---------|----------------------|
| C202 | 0.02 μF |
| C205 | 22 pF |
| C206 | 22 pF |
| C201 | 0.1 μF |
| C207 | 0.1 μF |
| C208 | 0.1 μF |
| C203 | 4.7 μF |
| C204 | 0.001 μF |
| NL2 | CUTTABLE NET LINK |
| NL1 | ALL LAYER NET LINK |
| F204 | 1AFA FUSE |
| F209 | 2AFA FUSE |
| F201 | 3.2ASB FUSE |
| F202 | 3.2ASB FUSE |
| F206 | 4ASB FUSE |
| F205 | 5ASB FUSE |
| F207 | 5ASB FUSE |
| F203 | 10ASB FUSE |
| X201 | CRYSTAL, 10 MHZ |
| U202 | PIC 16C56 10 MHZ (XT) (OTP) |
| U201 | OPT. COUPLED TRIAC DRIVER, O C |
| R209 | 100 Ohm |
| R202 | 1K Ohm |
| R211 | 10K Ohm |
| R214 | 10K Ohm |
| R210 | 100K Ohm |
| R217 | 100K Ohm |
| R218 | 100K Ohm |
| R219 | 100K Ohm |
| R220 | 100K Ohm |
| R221 | 100K Ohm |
| R222 | 100K Ohm |
| R223 | 100K Ohm |
| R224 | 100K Ohm |
| R225 | 100K Ohm |
| R226 | 100K Ohm |
| R227 | 100K Ohm |
| R203 | 22 Ohm |
| R213 | 220 Ohm |
| R208 | 330 Ohm |
| R215 | 330 Ohm |
| R207 | 47 Ohm |
| R216 | 470 Ohm |
| R201 | 470K Ohm |
| R204 | 680K Ohm |
| R205 | 680K Ohm |
| R206 | 680K Ohm |
| R212 | 680K Ohm |

TABLE 3-continued

| ELEMENT | COMPONENT VALUE/TYPE |
|---|---|
| D202 | POWER DIODE |
| D201 | SIGNAL DIODE |
| DS201 | LED |
| DS202 | LED |
| DS203 | LED |
| PTC201 | 1.35A PTC THERMISTOR |

Figure 6:
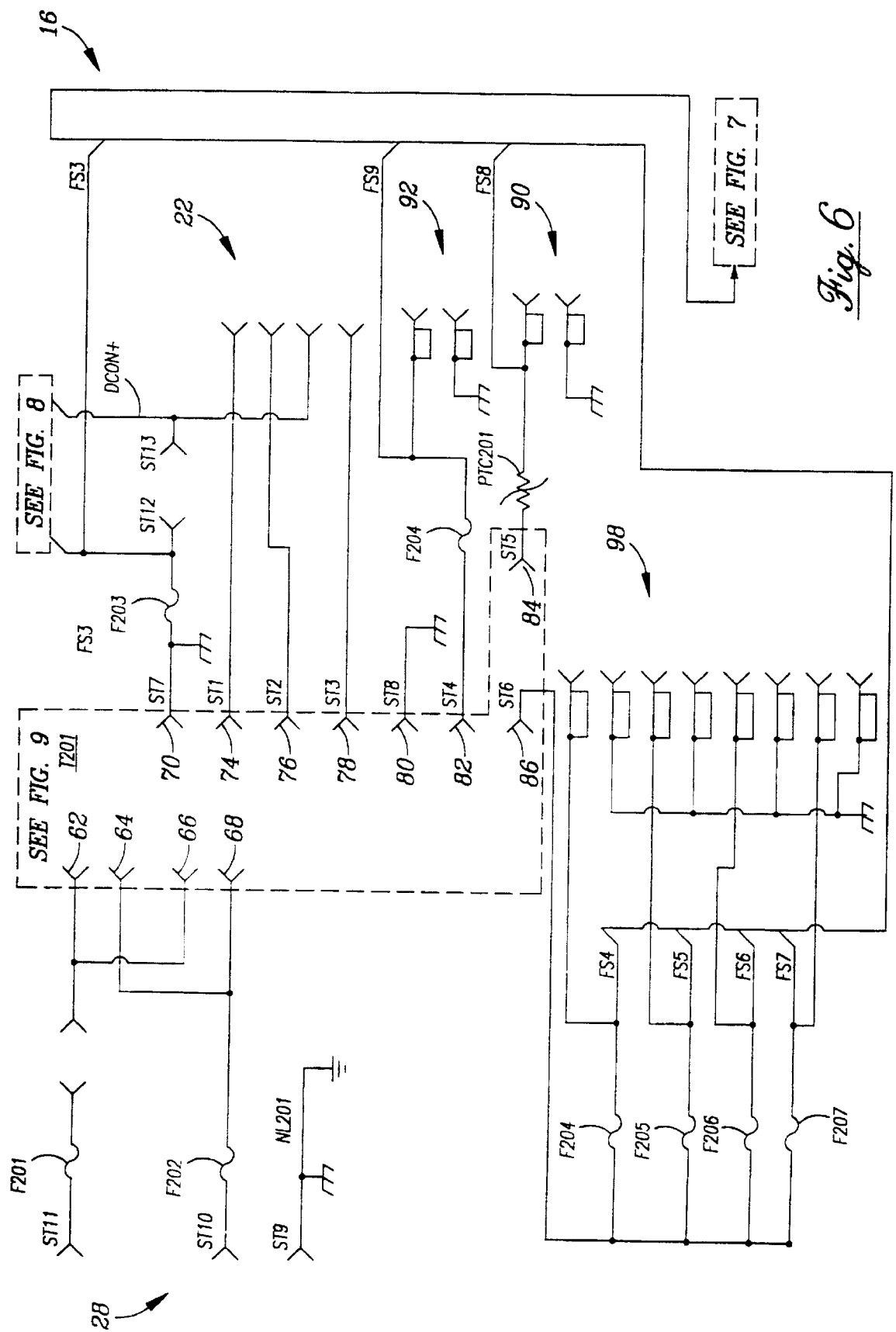
FIGS. 6, 7, 8 and 9 accumulatively illustrate the details of the power supply of FIG. 1.
Figure 8:
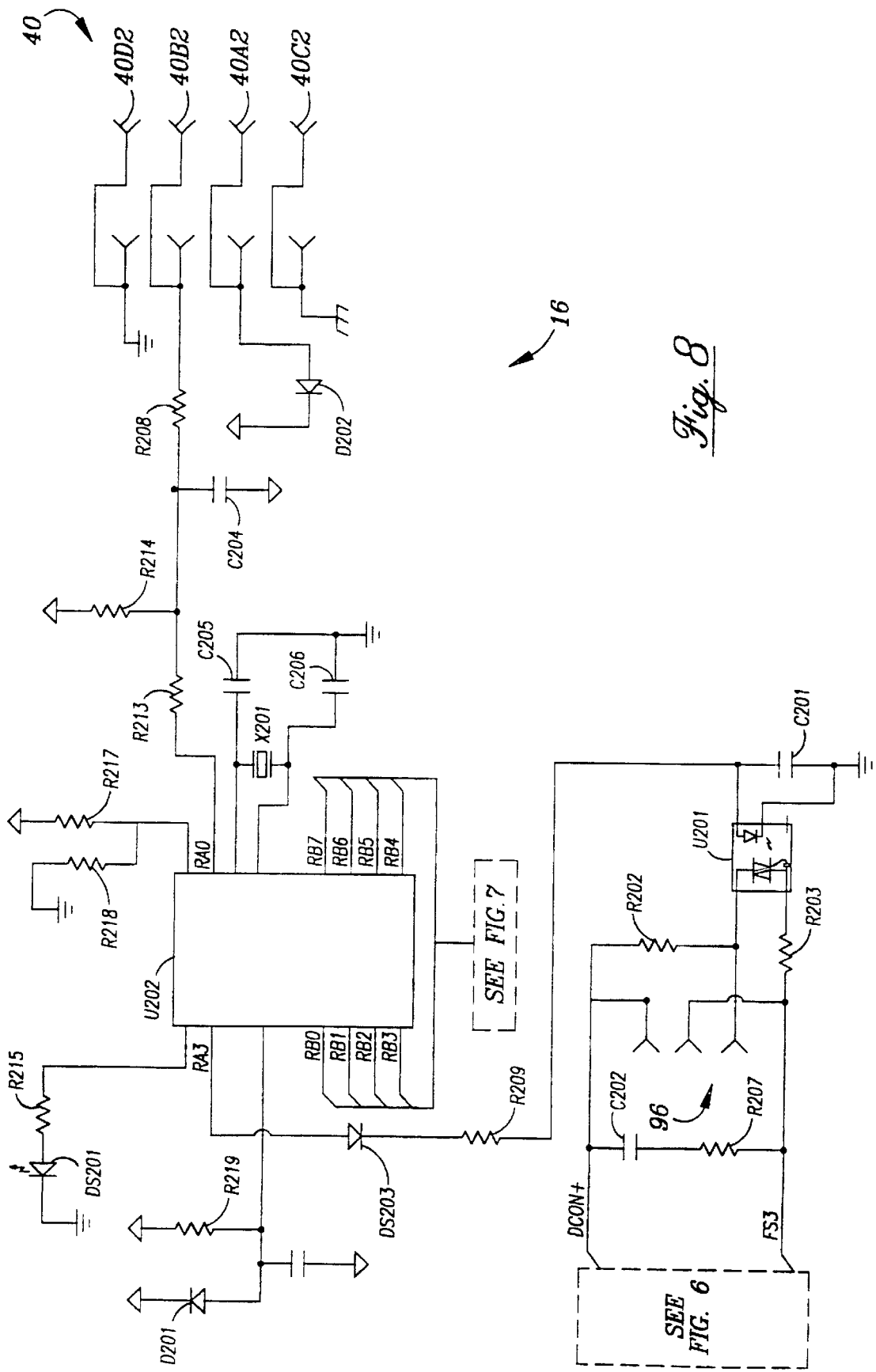
Figure 9:
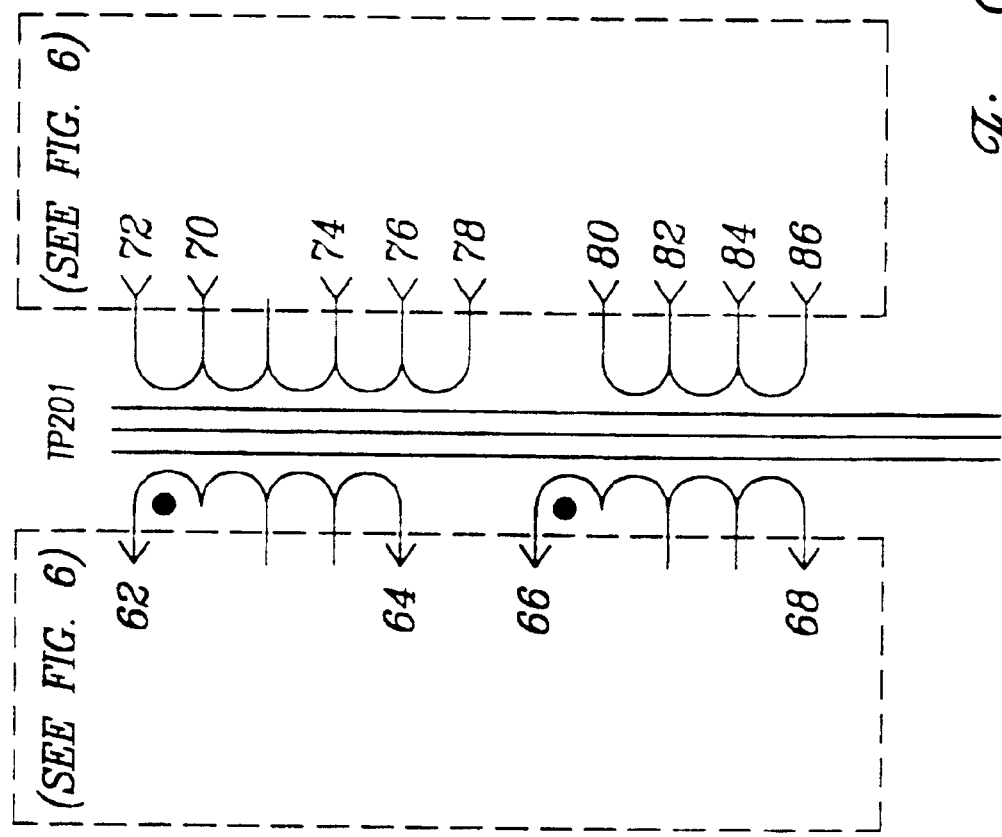

FIG. 6 illustrates the power supply 16 as receiving the line power on power excitation path 28 which is routed to the transformer T201 having input connectors and output connections shown in FIG. 6 but more clearly shown in FIG. 9. FIG. 6 further illustrates a control signal DCON+ developed by a light control circuit to be further described with reference to FIG. 8. FIG. 6 further illustrates fuses F4, F5, F6, F7 that are routed to a terminal board or connector 88. FIG. 6 also illustrates PTC201 serving as a fuse F8 that is routed to connector 90. FIG. 6 further illustrates fuse F9 that is routed to connector 92. The connectors 88, 90 and 92 are provided for additional users that may conveniently interconnect into the distributed intelligence system 10 by means of the serial communication bus 40 in a manner to be further described. The fuses F3, F4, F5, F6, F7, PTC201, and F9 are routed to the circuitry of FIG. 7 by way of signal paths FS3, FS4, FS5, FS6, FS7, FS8, FS9 respectively.

Figure 7:
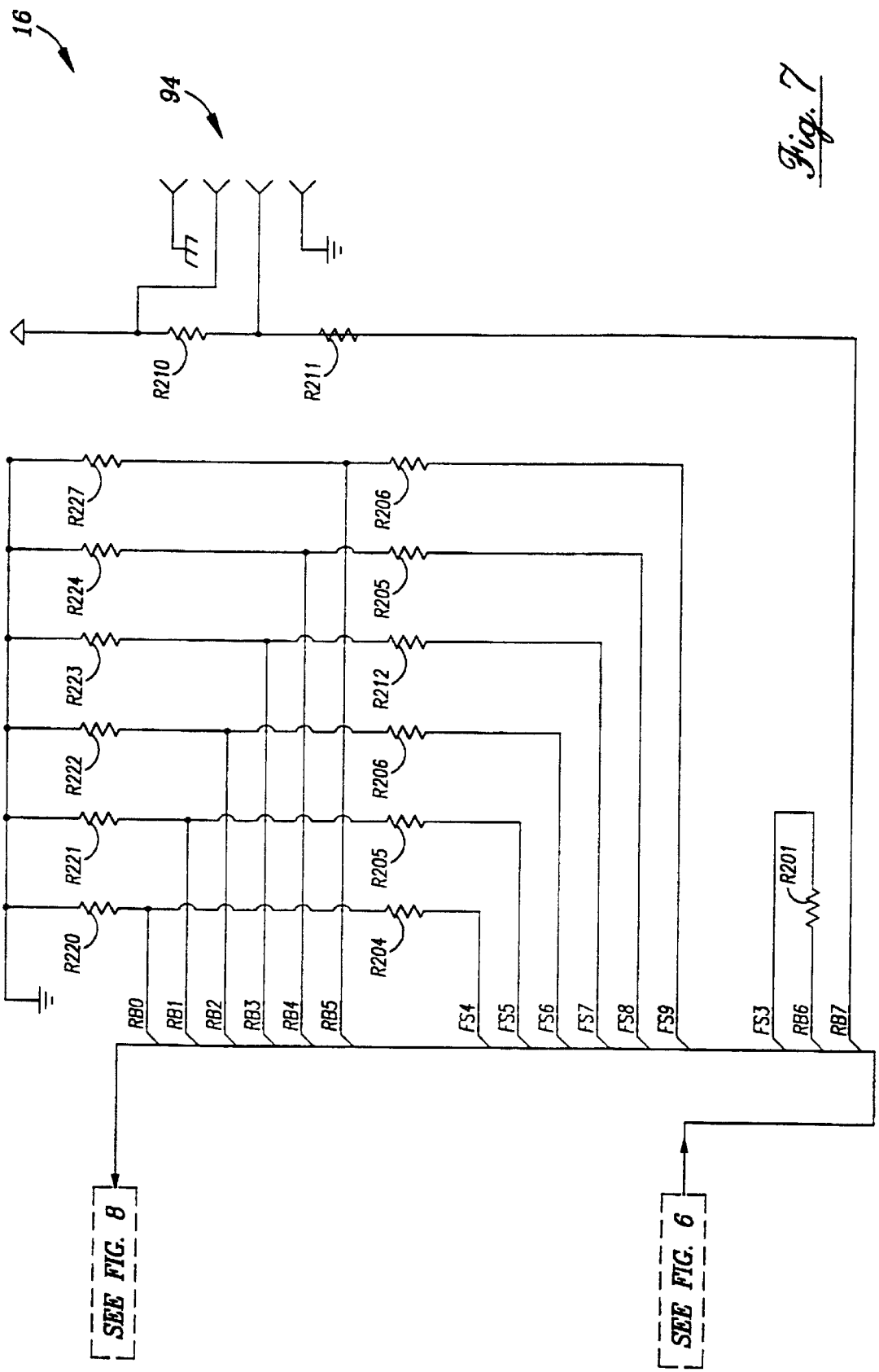

As seen in FIG. 7, the signal path FS3 is routed to signal path RB6 via resistor 201, whereas signal path RB7 is routed to connector 94 via resistor R211. The connector 94 is supplied to the second group of dental tools and equipment for dentistry. The signal paths FS4, FS5, FS6, FS7, FS8 and FS9 are respectively routed to signal paths RB0, RB1, RB2, RB3, RB4 and RB5 via resistors R204, R205, R206, R212, R225 and R226. The signal paths FS3, FS4, FS5, FS6, FS7, FS8, and FS9 allow the microprocessor U20 of FIG. 8 to sense the integrity of the fuses and report a fuse failure to external diagnostic devices if these devices, such as the diagnostic monitor 19 of FIG. 1, which are part of a diagnostic system, request the information. The signal paths RB0, RB1, RB2, RB3, RB4 and RB5 are further illustrated in FIG. 8.

FIG. 8 illustrates a third microcontroller U202 as having signal paths RB0, RB1, RB2, RB3, RB4, RB5, RB6 and RB7. The operation of the third microcontroller U202 is to be more fully described hereinafter. The third microcontroller U202 develops a control signal RA3 that is routed to the optical device U201 via the serial arranged diode DS203 and resistor R209. The optical device U201, in response to the control signal RA3, develops the control voltage DCON that is applied to the dental light 20 via signal path 22 shown in FIG. 6.

The third microcontroller U202 provides a signal RA0 containing the data that is routed to the serial communication bus 40 via conductor 40B2. The serial communication bus 40 related to the power supply 16 further comprises conductors 40A2, 40C2 and 40D2 that respectively carry the VBUS power, the return for the power and data paths, and the frame ground associated with the power supply 16. The data present in signal RA0 communicates with all of the equipment of the distributed intelligence system such as the control console 18 which may be further described with reference to FIG. 10 that comprises a plurality of elements having a typical value or of a type as given in Table 4.

TABLE 4

| ELEMENT | TYPICAL VALUE/TYPE |
|---|---|
| C301 | 0.1 µf |
| C302 | 22 pf |
| C303 | 22 pf |
| C304 | 0.001 µf |
| C305 | 0.1 µf |
| 0306 | 10 µf |
| D301 | Signal Diode |
| D302 | Power Diode |
| SW301 | Membrane Switch |
| SW302 | Membrane Switch |
| SW303 | Membrane Switch |
| SW304 | Membrane Switch |
| SW305 | Membrane Switch |
| SW306 | Membrane Switch |
| SW307 | Membrane Switch |
| X301 | Crystal 10 MHz |
| U301 | PIC 16C54A 10 MHz (XT) (OTP) |
| R301 | 100K ohm |
| R302 | 100K ohm |
| R303 | 100K ohm |
| R305 | 10K ohm |
| R306 | 330 ohm |
| R307 | 100K ohm |
| R308 | 100K ohm |
| R309 | 330 ohm |
| R310 | 330 ohm |
| R311 | 330 ohm |
| R312 | 330 ohm |
| R313 | 330 ohm |
| R314 | 330 ohm |
| R315 | 100K ohm |
| RL4 | 100K ohm |
| RR4 | 100K ohm |

Figure 10:
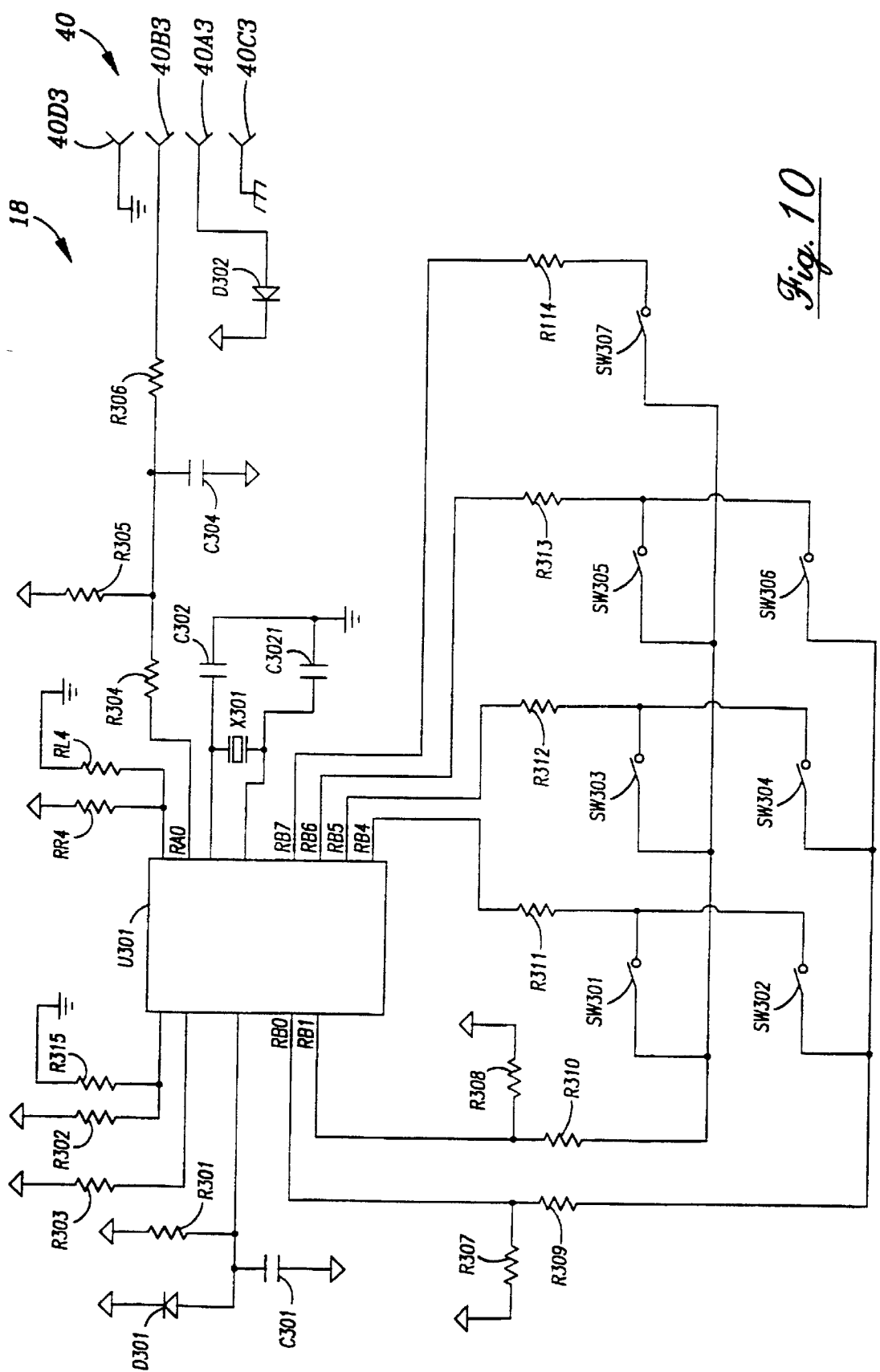
FIG. 10 illustrates the details of the control console of FIG. 1.

FIG. 10 illustrates a fourth microcontroller U301 arranged in a similar manner as the first, second and third microcontrollers and having a signal RA0 which carries the data that is applied to or extracted from the serial communication path 40 via conductor 40B3. The serial communication path 40 related to the control console 18 further has conductive paths 40A3 carrying the power VBUS, conductor 40C3 carrying the return for the power and data lines, and conductor 40D3 carrying the frame ground for the control console 18.

The fourth microprocessor U301 has control signals RB0 and RB1 which are switchably connected to control signals RB4, RB5, RB6 and RB7, via the resistors and switches arranged as shown in FIG. 10. The switches SW301, SW302, SW303, SW304, SW305, SW306 and SW307 of FIG. 10 are control switches that are activated by the dentist so as to initiate the operation of the tools and dental equipment.

As seen in FIG. 1, the diagnostic monitor 19 is attached to the dental bus 40. More particularly, the diagnostic monitor 19 is attached to the power VBUS of bus 40 to supply power thereon and to the data line of bus 40 to supply and receive data thereon. The diagnostic monitor 19 in response to operating routines and having the appropriate protocol means can send control messages to the control circuitry 12, as well as all other attached devices 14, 16 and 18 and to fetch the contents of stored information in the attached devices 12, 14, 16 and 18. This feature is used to automate the steps necessary to set up the system in manufacturing. Thus, a "manufacturing control" routine can act like a human operator to test and set up the dental chair in a manner to be more fully described with reference to FIGS. 11–26.

Furthermore, field service personnel can connect the diagnostic monitor 19 to the dental bus 40 and test peripherals and issue commands to the control circuitry 12. The diagnostic monitor 19 can also read a service history of the device from the EEROM to be described. Moreover, if the system 10 has no power available, power from appropriate circuits of the diagnostic monitor 19 may be provided externally via the dental bus 40. This allows external diagnostic devices to "power up" the bus 40 and check out the devices 12, 14, 16 and 18 without the need to apply power to the control circuitry 12.

It should now be appreciated that the present invention provides a diagnostic monitor 19 that assists in the maintenance and manufacturing check-out of the system 10 of FIG. 1.

It should now be further appreciated that the practice of the present invention provides for a distributed intelligence system having a serial communication bus comprised of only three conductors for controlling first, second, third and fourth groups of tools and equipment for dentistry that are respectively controlled by the operation of first, second, third and fourth microcontrollers that may be further described with reference to FIGS. 11–26.

FIGS. 11–26 illustrate the flow charts visualizing the interrelationship between the various program segments making up the operating routines that are being performed in the first, second, third and fourth microprocessors already described with reference to FIGS. 1–10. The microprocessors 1, 2, 3, and 4 exchange information by way of the serial communication bus 40 and use a communication protocol comprises low and high level commands. As previously mentioned, the serial communication bus 40 may be interchangeable referred to herein, especially for FIGS. 11–26, as a dental bus. High level commands generally direct the individual microprocessor to perform some complex function, such as to move the dental chair to a predefined position. Low level commands are specific to the individual microprocessor board and include such things as commanding the opening of a particular hydraulic control valve. The hardware protocol may utilize signal levels switching between 0 and 5 volts to communicate on the bus. Communication protocol also defines a series of status and diagnostic commands allowing the microprocessors to communication with each other to obtain diagnostic status information therebetween. An overview of the system communication involved in the present invention may be further described with reference to FIG. 11.

Figure 11:
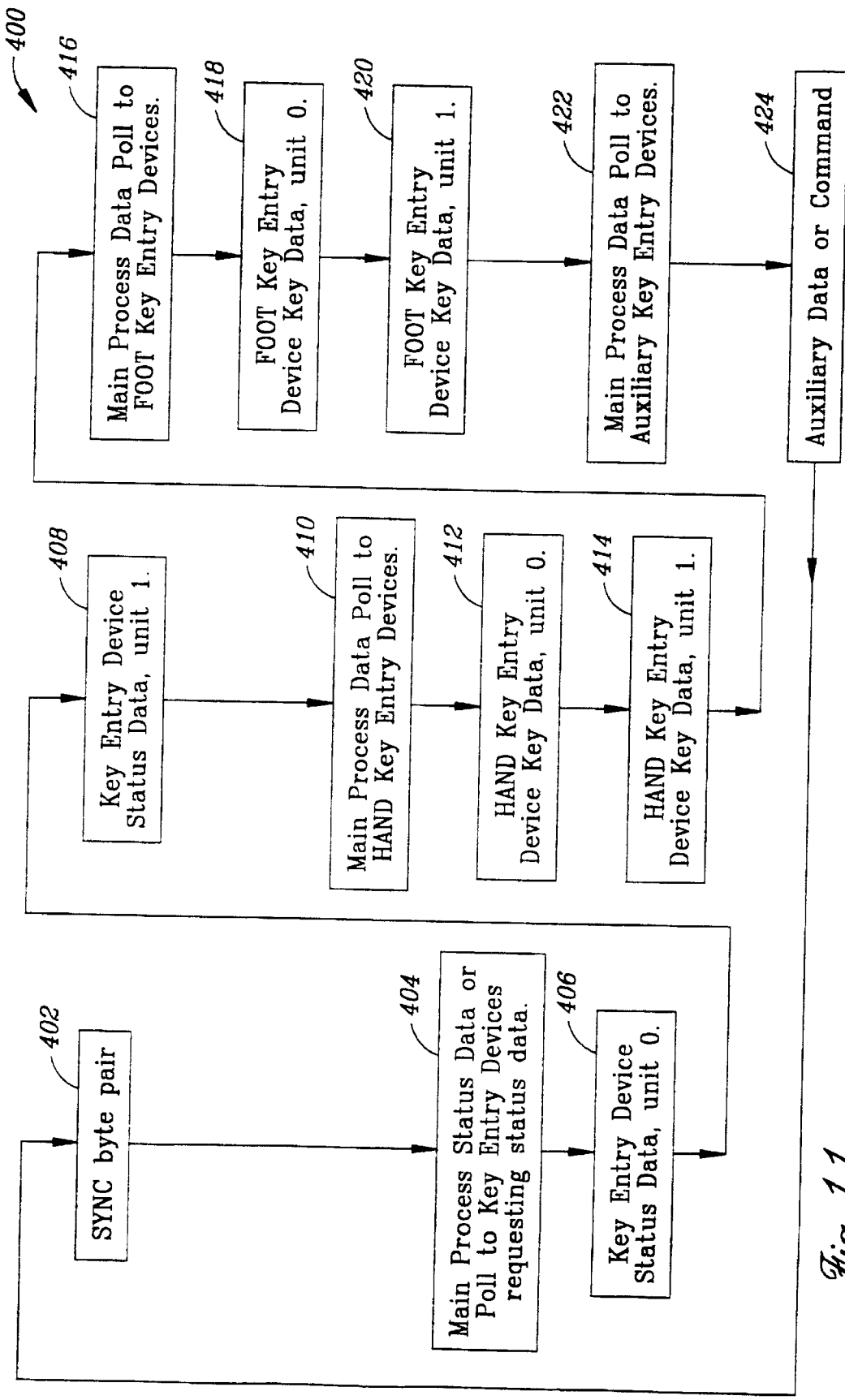
FIG. 11 is a flow chart of the system communications overview of the present invention.

FIG. 11 illustrates a system communication sequence 400 comprised of a plurality of program segments starting with program segment 402 and terminating with a program segment 424. The program segments of FIGS. 11–26 have remarks indicated thereon that give one or more statements of the salient features or operational aspects thereof. Further, the program segments are indicative of subroutines that perform one or more desired tasks in the overall operation of their associated routines.

Program segment 402 provides for synchronization between the various devices described with reference to FIGS. 1–10 and communicating with each other by way of the serial communication bus 40. More particularly, program segment 402 checks for the presence of a master synchronization pulses serving as a means for synchronizing timing between all devices in the serial communication bus 40. The master synchronization pulses comprise sync bytes having a typical value of 55 HEX, comprising alternate 0/1 patterns which allow for the devices on the serial communication bus 40 to adjust their baud rate so as to match that of the main board process routine 500 to be further described with reference to FIG. 12. This sync byte of 55 HEX allows for 10 milliseconds of quiet time which is reserved for the future communication use by processors not described herein. Program segment 402, upon completion, passes control to program segment 404.

The program segment 404 alternates control between polling key entry device status, to be further described, and broadcasting the results of the main board process to be further described with reference to FIG. 12. The main board process of FIG. 12 polls selected keys, such as those of FIGS. 1–10, to determine if the key is ready to send corresponding data and status information. As previously mentioned, the response of the selected keys is recognized by the presence of the appropriate information on the serial communication bus 40 of FIGS. 1–10 and interchangeably referred to herein as the dental bus. The main process interprets program segments 404, 406 and 408 and passes control to program segment 404 which, in turn, passes control to program segment 406 which operates in conjunction with program segment 408.

Program segments 406 and 408 communicate with the serial communication bus 40, and the main board process of FIG. 12 polls the particular device which may be a unit 0 (program segment 406) or a unit 1 (program segment 408), wherein units 0 and 1 may be any device having data entry capability. Typically, and as to be further described, the first unit to respond to being polled is termed unit 0 and the second unit to respond to being polled is unit 1. These units 0 and 1 are related to one series of polling, wherein each of such series has units termed 0 and 1. Upon being polled, program segment 406 returns the status state of the unit 0 to the serial communication bus. Program segment 408 waits for program segment 406 to respond to its being polled and then program segment 408 puts its status data onto the serial communication bus 40 and then passes control to program segment 410.

Program segment 410 cooperates with the main board process in a manner similar to program segment 404. Program segment 410 polls two hand key entry devices such as units 0 and 1. The hand key entry devices associated with program segments 412 and 414, if present, return key pressed data or a stuck switch error code. The stuck switch error code is indicative that the selected switch may be stuck and therefore inoperative. The stuck switch error code alerts the main board process of FIG. 12 to ignore key information from the associated device/unit. This detection of a failure (defective switch) by a remote unit (the control circuitry 12) provides a "safing" condition in which the message from the defective unit is discarded, thereby, preventing the system 10 of the present invention from pursuing an erroneous command. Moreover, this detection provides fault tolerance for the system 10 of the present invention. More particularly, if a unit is determined to be broken, it drops off the bus 40. This allows other units to provide the necessary control functions. This is an important feature of the present invention because it prevents a situation where a device that fails "ON" prevents other operative devices from being utilized. As will be further described, a diagnostic process can be connected to the serial communication bus and by listening or monitoring for the status data responses, determine which switch is stuck. Upon completion of program segment 414, control is passed back to the main board process of FIG. 12, in particular, program segment 416 being interpreted and manipulated by the main board process of FIG. 12.

Program segment 416 examines the foot entry devices and has associated program segments 418 and 420. Program segment 418 and 420 operate in a similar manner as program segments 412 and 414 so that the foot key entry devices, if present and operative, return status and data to the main board process routine 500 of FIG. 12. The stuck switch error code alerts the main board process of FIG. 12 to ignore the foot key entry information from this device/unit. As discussed with reference to program segments 412 and 414, a diagnostic process can be connected to the communication bus and by monitoring the status and data responses determine which switch is stuck. Upon completion, program segment 420 passes control back to program segment 422.

Program segment 422 interrogates the auxiliary key devices associated with program segment 424, and if any are present, return key pressed data, an error code, or extended more complex commands for an auxiliary piece of equipment, such as the diagnostic monitor 19 of FIG. 1 which is associated with the dental chair. The factory test/initialization of the dental chair may be also done by using the dedicated diagnostic monitor 19 of FIG. 1 as an auxiliary device. The diagnostic monitor 19 employing logic and control mechanizations similar to those of the control circuitry 12 moves the chair to its limits, sets EEROM parameters, and does a run-in, base/back up/down cycling of the chair. This feature associated with the diagnostic monitor 19 may be used to access EEROM parameters for maintenance capability or to automate the steps necessary to set up the system 10 in manufacturing. These limits and EEROM parameters are to be further described hereinafter with reference to FIG. 17. The main board process routine 500 may be further described with reference to FIG. 12 composed of FIGS. 12(A), 12(B), 12(C) which cumulatively illustrate the flow chart for the main board process routine 500 of the present invention.

The main board process routine 500 is the operating routine being run in the first microprocessor, that is, microprocessor U1 already described with reference to FIGS. 3 and 4. The interconnections of the microprocessor U1 to devices, such as watch dog timer U2, that affect the main board process 500 are as previously described with reference to FIGS. 1–10. Further, the interconnections of the microprocessors U101, U201 and U301 (second, third and fourth microprocessors) that are controlled by processes to be described hereinafter with reference to FIGS. 13–26, are also as previously described with reference to FIGS. 1–10.

The main board process routine 500 has initialization means comprised of program segments 502, 504, 506 and 508 which when being performed causes any movement of any chair element to be stopped until valid communication is established with at least one of the other processes sending data on the communication bus 40. Upon power up, program segment 502 senses a hardware generated reset and provides an input to program segment 504. Program segment 504, determines the cause of the hardware generated reset and, if the cause is a watchdog timer reset, provides that information to program segment 506 which updates an error statistic tabulation that records the overall errors associated with the system 10 of the present invention. The watchdog timer resets the processor if the bus cycling is not complete within its designated time interval between the start of one cycle and the start of the next cycle. During maintenance, the main board process routine 500 of FIG. 12 issues no polls or sync pulses and from the watchdog timer reset depends on the diagnostic monitor generating proper bus cycles. If the cause of the reset was normal power on condition, that information is passed to program segment 506 in addition to program segment 508.

Program segment 508 initializes an internal storage and external I/O interfaces, while also starting timer 0 and 1 interrupt processors causing the interactive exchange of information on the serial communication bus 40 as determined on periodic basis by external hardware. Upon completion, program segment 508 notifies the main board wait process, to be described with reference to FIG. 13, the timer 0 process 700, to be described with reference to FIG. 14, and the timer 1 process 800, to be described with reference to FIG. 15. In general, the wait process 600 allows key devices to synchronize with the serial communication bus 40 and for their associated analog-to-digital values to settle. Upon completion, program segment 600 passes control to program segment 510.

Program segment 510 determines if the analog-to-digital converter samples associated with the device being polled by the main board process 500 exceed the number 6, and if no, then passes control to program segment 512 which, in turn, saves the previous A/D converter values and fetches or gets new A/D values and passes control to program segment 514.

Program segment 514 determines if the number of A/D samples exceed 3, and if the answer is yes, program segment 514 performs an A/D test routine 900 to be further described with reference to FIG. 16. If the number of samples of program segment 514 is less than 3, program segment 514 passes control back to program segment 510 which again determines if the number of A/D samples exceeds 6 and once the answer is satisfied (yes) passes control to program segment 518 of FIG. 12(B).

Figure 15:
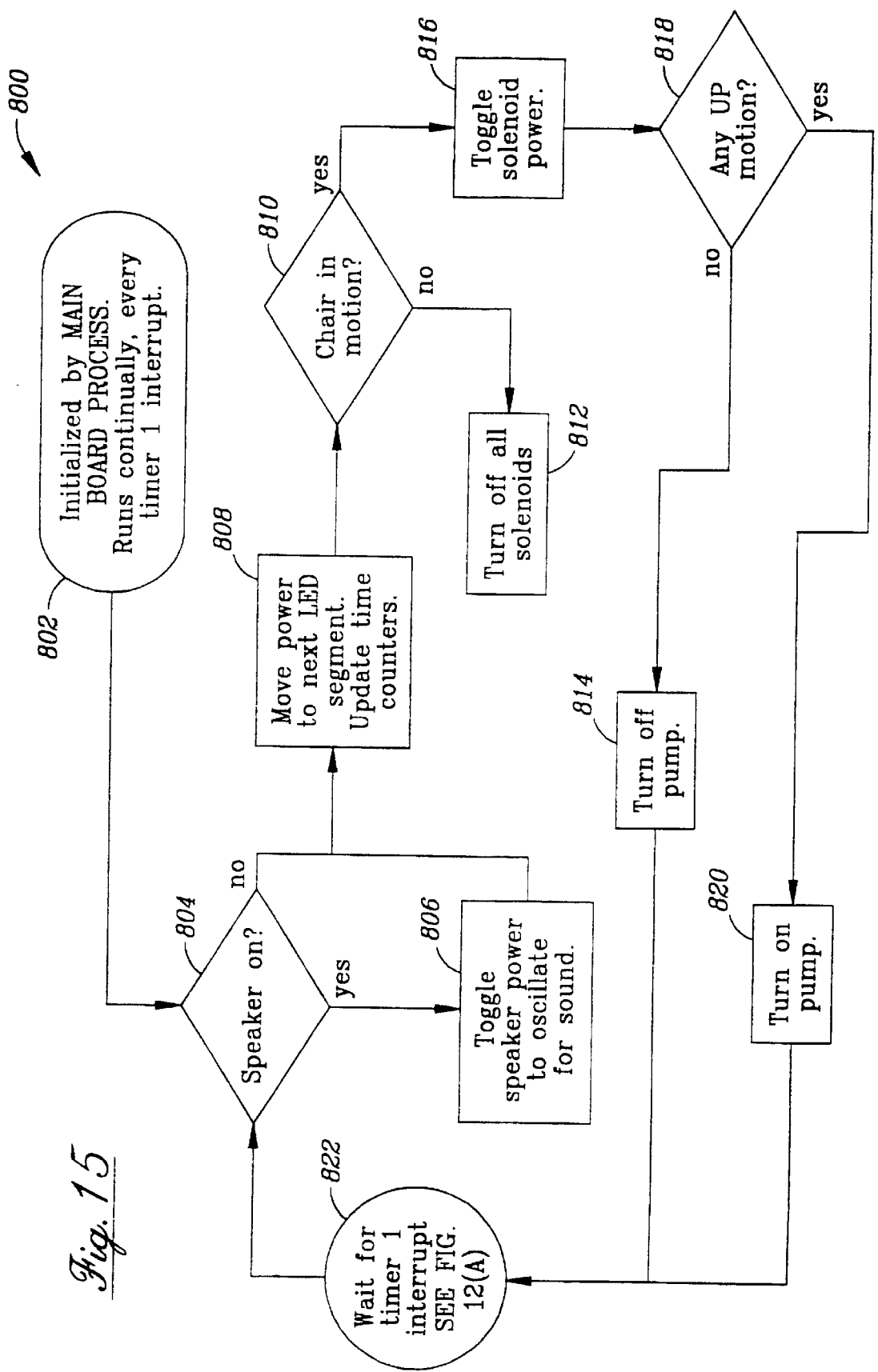
FIG. 15 is a flow chart of the main board process timer 1 routine of the present invention.

Program segment 518 determines if the hardware associated with the A/D converter samples is okay, and if the answer is yes, causes the speaker X2 of FIG. 3, previously described, to be turned on, then waits 100 milliseconds for timer 1 process 800 of FIG. 15 to oscillate the speaker, and then turns the speaker off. Program segment 518 passes control to wait routine 600 to be described with reference to FIG. 13 which, in turn, passes control to read EEROM data blocks routines 1000 to be described with reference to FIG. 17 which, in turn, passes control to program segment 520.

Program segment 520 stops any movement of the dental chair that may be in process and displays any error code that it might receive from program segments 516 and 530 and routines 1000 on appropriate LEDs, such as those described with reference to FIGS. 1–10, and then passes control to program segment 522.

Program segment 522 is related to ALLSTOP which is used to stop any possible chair motion, terminate any multiple key entry procedures and cause the speaker X2 to be beeped once, and then passes control onto program 600 to be described with reference to FIG. 13 which, in turn, essentially waits 200 milliseconds and then passes control to program segment 524 of FIG. 12(C).

Program segment 524 displays the chair status upon appropriate LEDs, such as those described with reference to FIGS. 1–10, and passes control to program segment 526 which is a decisional program segment that determines if any special diagnostic mode should be entered into, and if the answer is yes, then passes control to program segment 528 which performs such limited diagnostics commands.

Program segment 528 (as well as 1030 to be described) cooperates with the array 58 of FIG. 4 of optional control jumpers whose purpose is to allow the service personnel to configure the operation of the system. The microprocessor U1 of the control circuitry 12 senses the presence or absence of these jumpers to make minor modifications to its operational flow. For example, program segments 528 and 1030 sense to detect if one of the jumpers of array 58 is present for mechanical limit setting to occur.

If the answer to the program segment 526 is no, control is passed to wait routine 600, to be described with reference to FIG. 13 which, in turn, essentially causes a wait of 11 milliseconds and then passes control onto program 1100 which is a communications routines 1100 to be further described with reference to FIG. 18 which, in turn, passes control to program segment 534.

Program segment 534 determines if there are any flags for WAITKEYS. WAITKEYS are used to stop any chair motion and to beep the speaker X2 of FIG. 3. WAITKEYS normally occur when the operator has not let go of the associated pressed keys and the operating routines within the U1 microprocessor of FIG. 3 determines such to be in error and sets error (WAITKEYS) flags. This type of internal fault detection is applicable to each of the microprocessors of the present invention. More particularly, each individual microprocessor can determine if it (or its support devices) are defective and, accordingly, refuse to execute any command the individual microprocessor determines to be unsafe. If for the example of the U1 microprocessor, there are no flags for WAITKEYS, control is passed to routines 1200, command execution, to be further described with reference to FIG. 19 which, in turn, passes control to program segment 532 which is similar to program segment 534 that checks for flags for WAITKEYS, and if a WAITKEYS flag is present (yes), control is passed to program segment 516 of FIG. 12(B) previously discussed. If no WAITKEYS flag is present, program segment 532 passes control to program segment 530.

Program segment 530 is a decisional segment which checks for errors requiring ALLSTOPS which stop any motion of the chair and causes a beep of the speaker. If the answer to these questions are no, program segment 530 passes control to program segment 524 and, conversely, if the answer to the questions is yes, program segment 530 passes control to program segment 520 of FIG. 12(B).

Figure 12A:
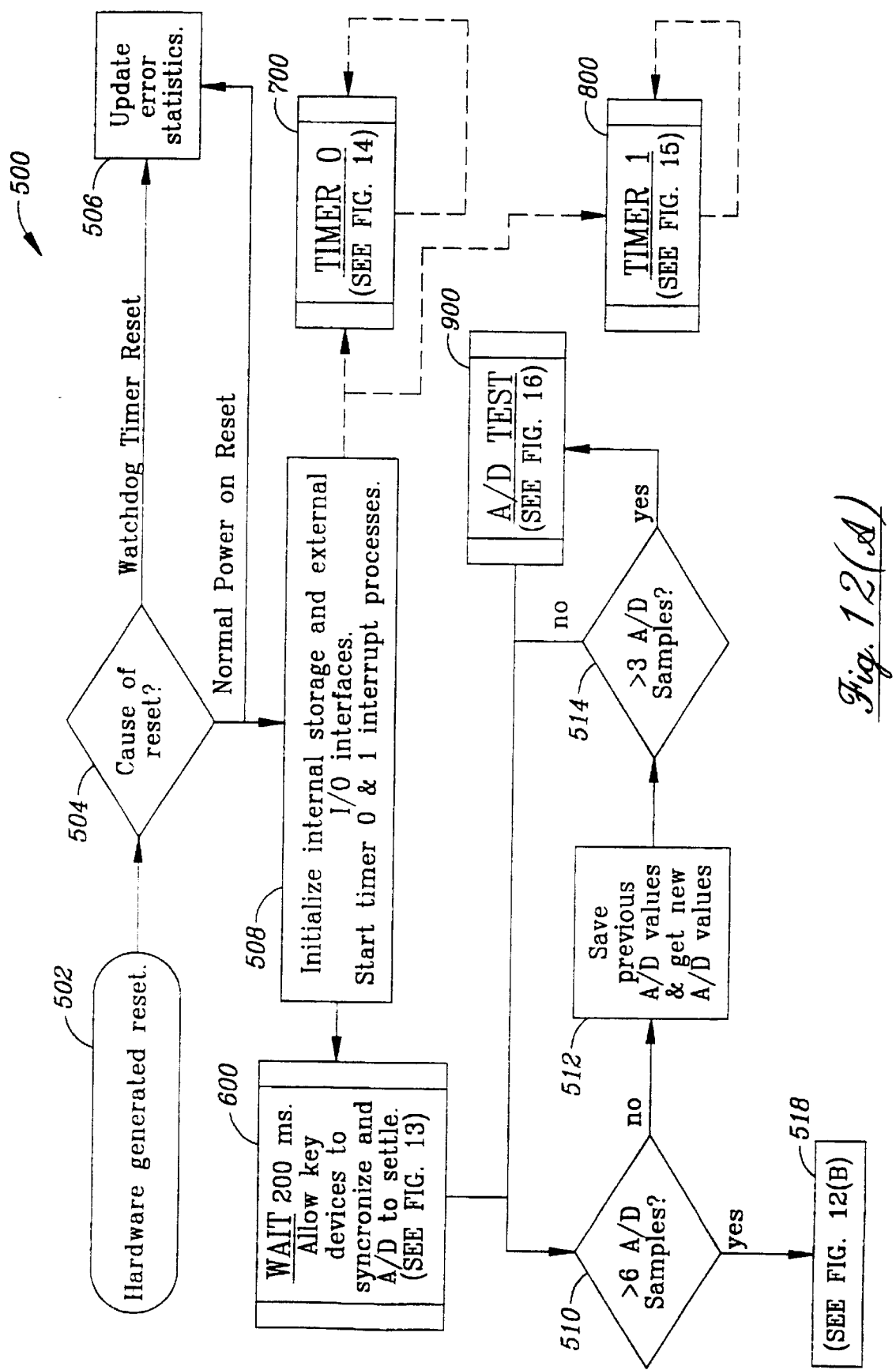
FIG. 12 is composed of FIGS. 12(A), 12(B) and 12(C) that cumulatively illustrate the flow chart of the main board process of the present invention.
Figure 12B:
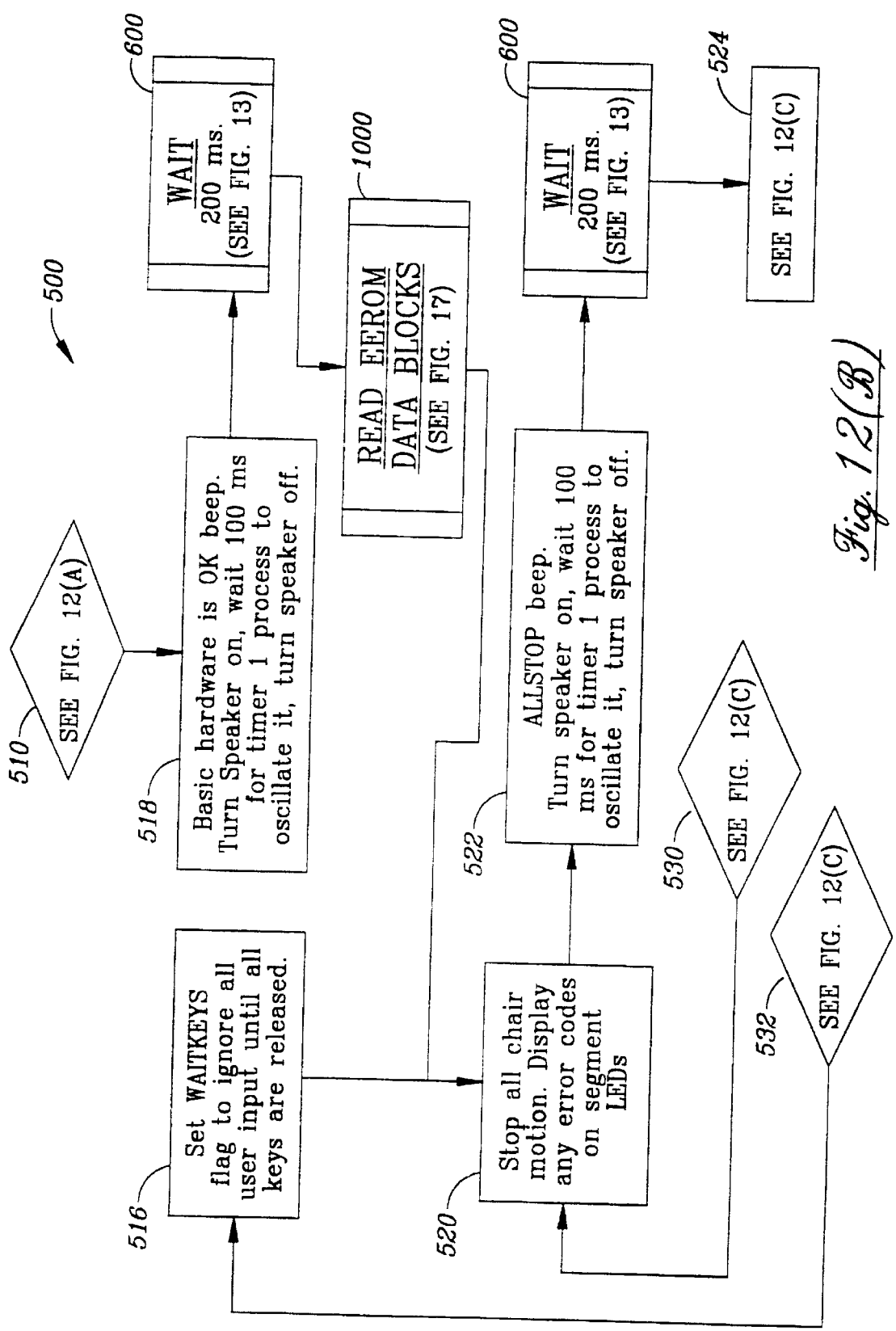

Program segment 516 of FIG. 12(B) that receives control from program segment 532 of FIG. 12(C), sets the WAIT-KEYS flag so as to ignore any further key inputs until all keys are released signifying that the associated key is again operative and then passes control back to program segment 520.

Program segment 524 of FIG. 12(C) displays the status of the answers (no errors) of program segment 530 and then passes control to program segment 526 which operates in a manner as previously described, and passes control, to program 600 which may be further described with reference to FIG. 13

Figure 13:
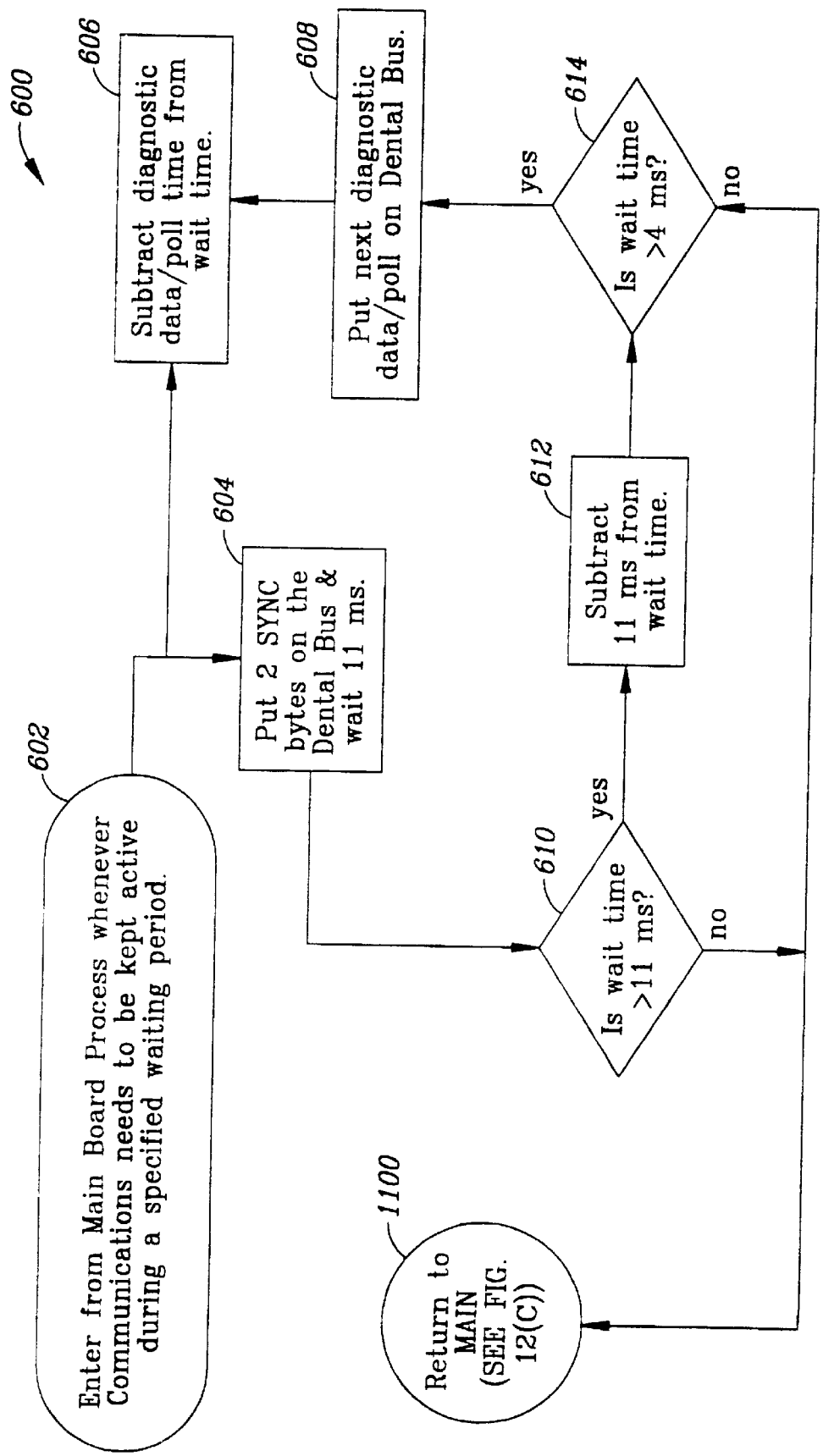
FIG. 13 is a flow chart of the main board process wait routine of the present invention.
Figure 14:
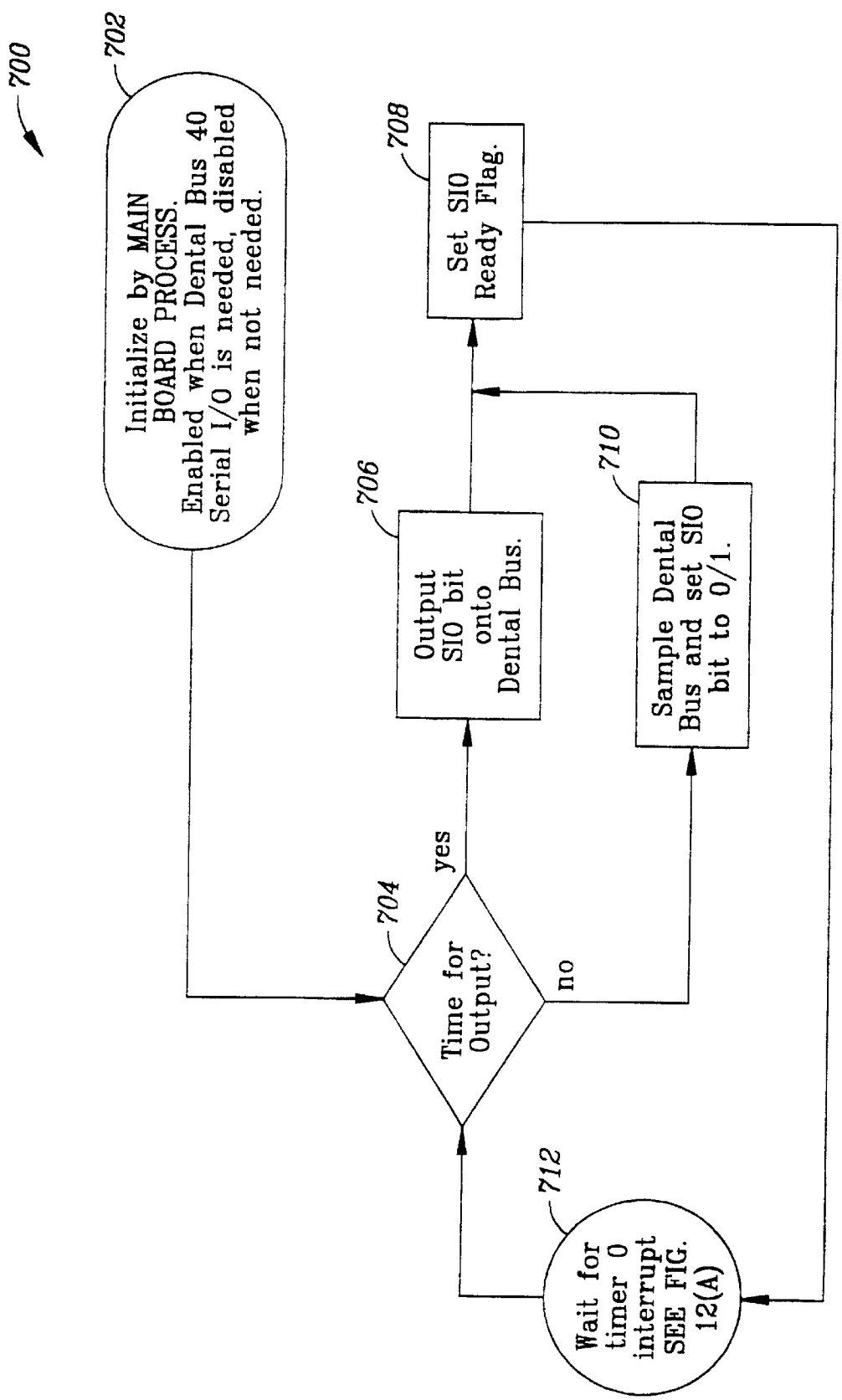
FIG. 14 is a flow chart of the main board process timer 0 routine of the present invention.

FIG. 13 illustrates the main board process wait routine 600 comprised of the program segment 602, 604, 606, 608, 610, 612 and 614 all of which reside in the U1 microprocessor of FIG. 3. Program segment 602, in particular, the remarks shown therein indicates that the main board process wait 600 is entered from the main board process, described with reference to FIG. 12, whenever communications, such as communications being conducted via the serial communications bus 40, need to be kept active during a specified waiting period. Program segments 604 and 608 refer to a dental bus which is the serial communication bus 40 previously described with reference to FIGS. 1–10.

The program segments 604, 606 . . . 614 are arranged in a manner known in the art and as shown in FIG. 13 so as to provide for the different waiting periods involved with the overall sequences described herein with reference to FIGS. 11–26. Upon completion, that is, upon the occurrence of either of the no paths of program segments 610 and 614, control is returned to the routine to which it passes control to, such as main board communications 1100 of FIG. 18, generally illustrated in FIG. 12(C). It should be recognized that the main board process wait routines 600 of FIG. 13, also generally illustrated in FIG. 12(A), may be fetched by many of the routines of FIGS. 11–26 and provide for a desired and appropriate wait period. Similarly, the main board process timer 0 or 1 may be fetched by many of the routines of FIGS. 11–26. The main board process timer 0 generally illustrated in FIG. 12(A) may be further described with reference to FIG. 14.

The main board process timer 0 routine 700 is comprised of program segment 702, 704, 706, 708, 710 and 712, wherein program segments 702, 706 and 708 refer to a dental bus which is the serial communication bus 40 of FIGS. 1–10. The remarks of program segment 702 point out that the main board process timer 0 is initialized by the main board process of FIG. 12A and is enabled when the dental bus 40 serial input output I/O is needed and is disabled when the serial I/O is not needed. Program segment 702 passes control to program segment 704.

Program segment 704 determines if the time for output of any particular routine being run in the microprocessor U1 of FIG. 3 has occurred, and if the answer is yes, passes control to program segment 706 which, in turn, outputs the SIO bit onto the dental bus 40 and then passes control to program segment 708 which sets the SIO ready flag related to the dental bus 40. If the decision of program segment 704 is no, program segment 704 passes control to program segment 710 which samples the dental bus and sets the SIO bit to either a 1 or a 0 and then passes control to program segment 708.

Program segment 708, when completing its function illustrated by its enclosed remarks, passes control to program segment 712 which waits for the timer 0 interrupt to occur which is being sent by program segment 508 of FIG. 12(A). Program segment 508 also creates the interrupt that initiates the main board process timer 1 routine 800 that may be further described with reference to FIG. 15.

FIG. 15 illustrates the main board process timer 1 routine 800 which is being run in the U1 microprocessor of FIG. 3 having the initial program segment 802. The phrase "main board" in the title of the routines of FIGS. 11–26 represents that the routine is being run in the U1 microprocessor. Program segment 802 is initialized by the main board process of FIG. 12 and runs continuously, every timer 1 interrupt. Program segment 802 passes control to program segment 804.

Program segment 804 checks to see if the speaker X2 of FIG. 2 is on, and if no, passes control to program segment 808 and, conversely, if the speaker is on, passes control to program segment 806 which toggles the speaker power to oscillate the speaker for sound and when complete passes control to program segment 808.

Program segment 808 updates the LED display, such as those described with reference to FIGS. 2–10, related to the power and also updates related time counters associated with chair movement and when complete passes control to program segment 810 which determines if the chair is in motion and, if no motion, passes control to program segment 812 which turns off all solenoids and then passes control to program segment 814 which, in turn, turns off the dental chair pump, and when complete passes control back to program segment 822 which waits for timer 1 interrupt which is created by program segment 508 of FIG. 12(A).

Program segment 810 upon determining if the chair is in motion passes control to program segment 816 which toggles the solenoid power related to the chair and then passes control to program segment 818 which, in turn, determines if there is any up motion involved in the chair, and if the determination is yes, passes control to program segment 820 which turns off the dental chair pump and then passes control back to program segment 822 already discussed. If program segment 818 determines that there is not any up motion, it passes control to program segment 814 previously discussed that relinquishes control back to FIG. 12(A). Also shown in FIG. 12(A) is the analog-to-digital routine 900 which may be further described with reference to FIG. 16.

Figure 16:
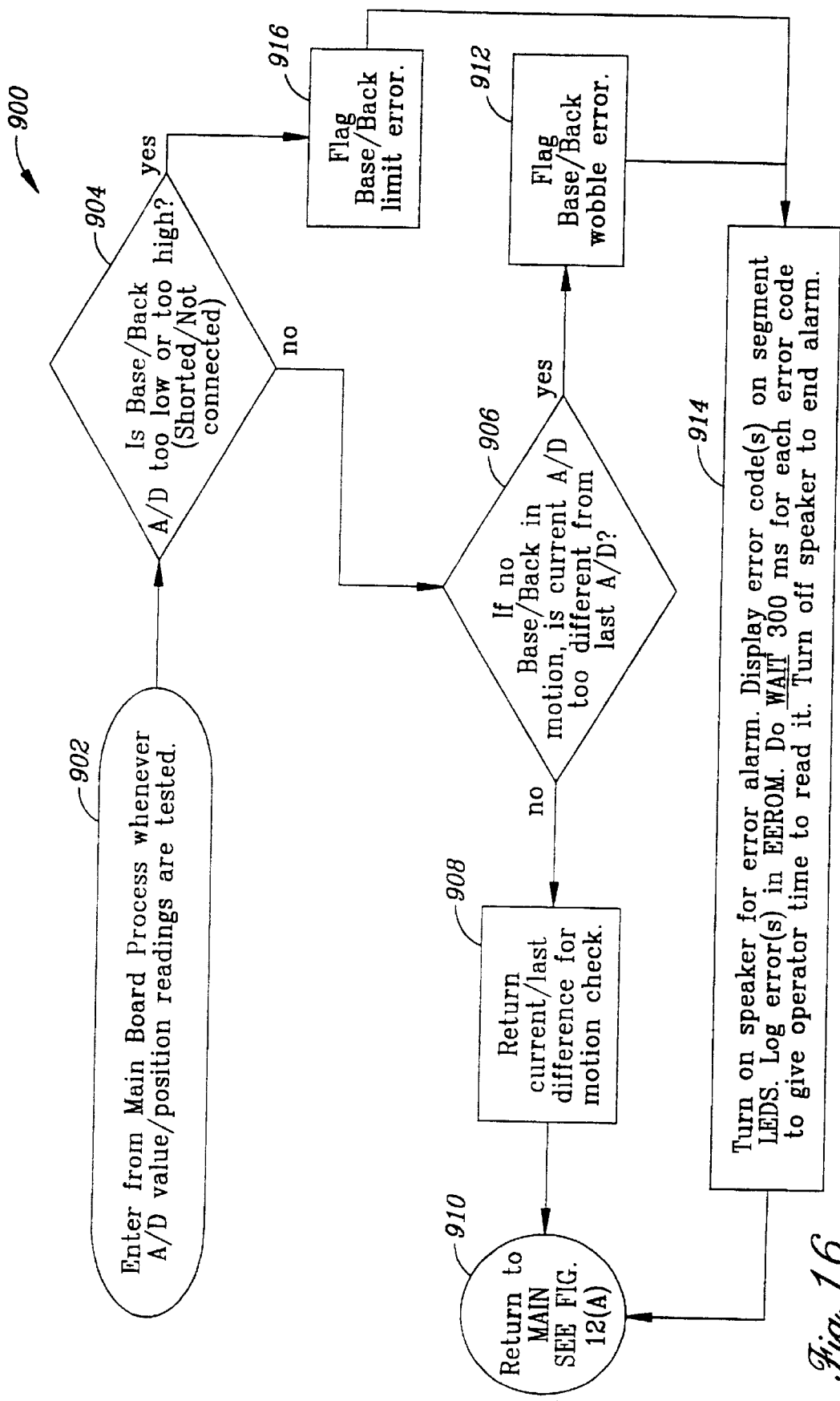
FIG. 16 is a flow chart of the main board process analog-to-digital (A/D) test routine of the present invention.

FIG. 16 illustrates the main board process A/D test routine 900 having an initial or entrance program event 902. The main process A/D test 900 is entered in from the main board process of FIG. 12 whenever A/D value/position readings are tested. The A/D value may indicate the response of any device having an analog output and that monitors such conditions as movement, temperature, sound, etc., and which analog output is converted into a digital quantity. The A/D position is typically the position (actual or desired) of the dental chair being serviced by the distributed intelligent system 10 of the present invention. Program segment 902, from which the request for the A/D test is determined, passes control to program segment 904 which determines if the A/D value related to the base/back position of the dental chair is too low or too high, and if the inquiry yields a no answer, passes control to program segment 906.

Program segment 906 determines if the A/D value is indicative that the base/back is in motion and also if the current A/D value of the base/back position is too different from the last corresponding A/D value, and if the answers to these queries is no, passes control to program segment 908 which, in turn, returns the difference between the current and last A/D values for a motion check limit and then passes control to program segment 910 which returns control to the routines 500, as shown in FIG. 12(B).

The limit checks performed by program segments 904, 906 and 908 are all meant to restrict the motion of the dental chair. These limits are related to hard limits, soft limits, base safety limits, and no motion time limit. These limits checks represent sample of diagnostic routines employed by the present invention to prevent any unwanted error of the system 10 from causing any undue injury to any person being treated by a dental person operating the system 10 of the present invention. Hard limits are the physical extremes that the mechanical structure of the chair base/back can move from between its up and down position. Soft limits are predetermined in the factory and are usually located inside the range of the hard limits. As will be further described with reference to FIG. 17, the EEROM related to the control of the dental chair are used to keep the chair from potential damage by repeated motion stopping at the hard limits. The base safety limit switch may be on the chair itself, and is used to stop the chair if it has disadvantageously come down on top of an unplanned for object. The no motion limit is used to stop the chair motion if the A/D current position readings do not change as to be expected. More particularly, if the dental chair is supposed to be moving, and it is not, then something is wrong and an alarm is generated and the motion of the chair is prevented.

If program segment 906 determines a fault condition, that is, an alarm condition, e.g., the current A/D reading is too different from the last A/D reading, it passes control to program segment 912 which flags the alarm as being a base/back wobble error and then passes control to program segment 914. Program segment 914 also receives a base/back limit error that may be determined by program segment 904.

Program segment 914 turns on the speaker X2 for an alarm error and displays the error code on the LED thereof and logs the error in the EEROM elements of the system 10 to be further described with reference to FIG. 17. It is desired that the operating program wait 300 milliseconds to and from each error code so as to give the operator sufficient time to read the LED displays and to turn off the speaker. The speaker is turned off when the alarm condition has been duly recorded and the program segment 914 passes control to program segment 910 previously discussed and shown in FIG. 12(A) which also illustrates the read EEROM data blocks routine 1000 which may be further described with reference to FIG. 17.

Figure 17A:
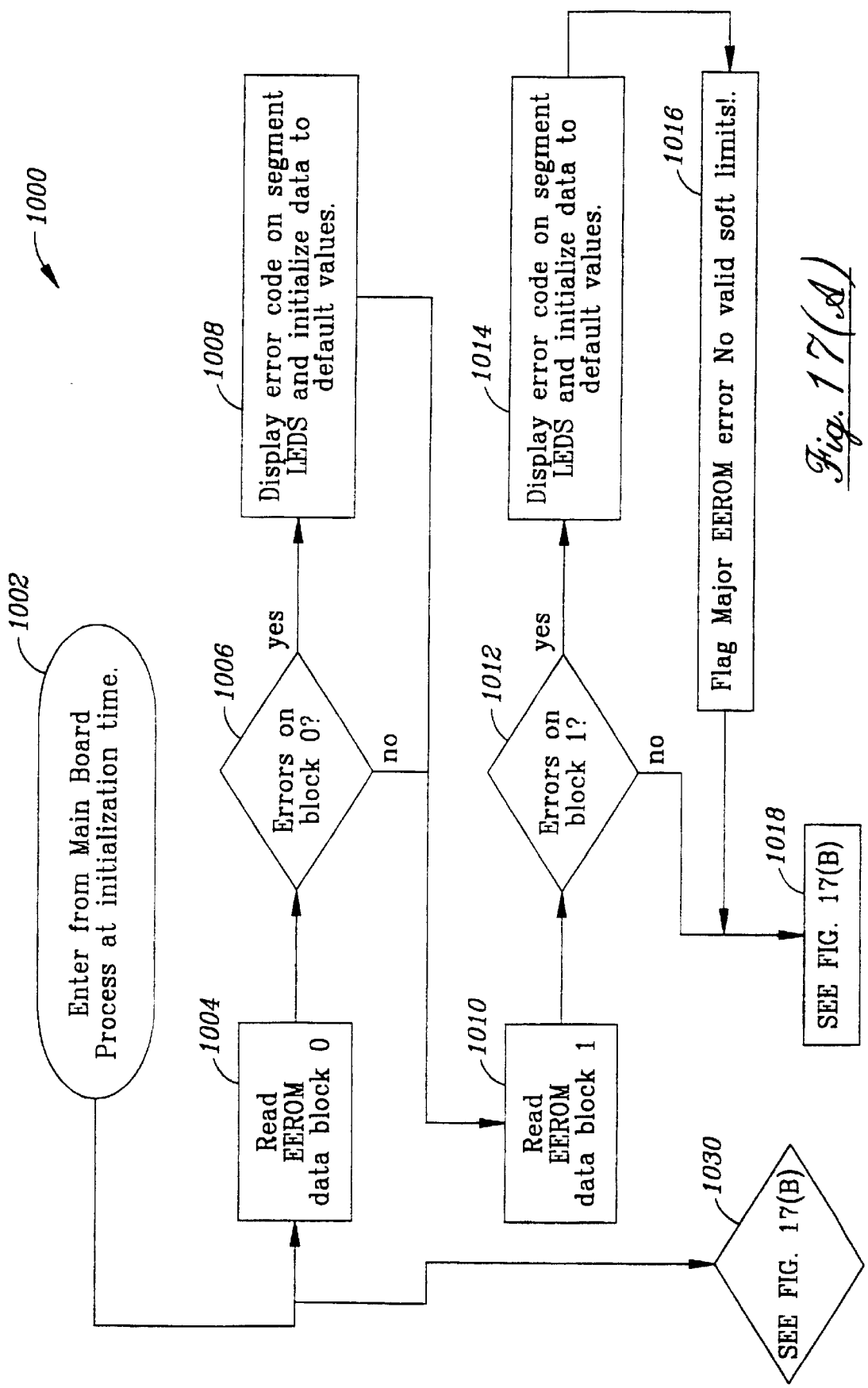
FIG. 17 is composed of FIGS. 17(A) and 17(B) that cumulatively illustrate the flow chart of the main board process read EEROM data blocks routine of the present invention.
Figure 17B:
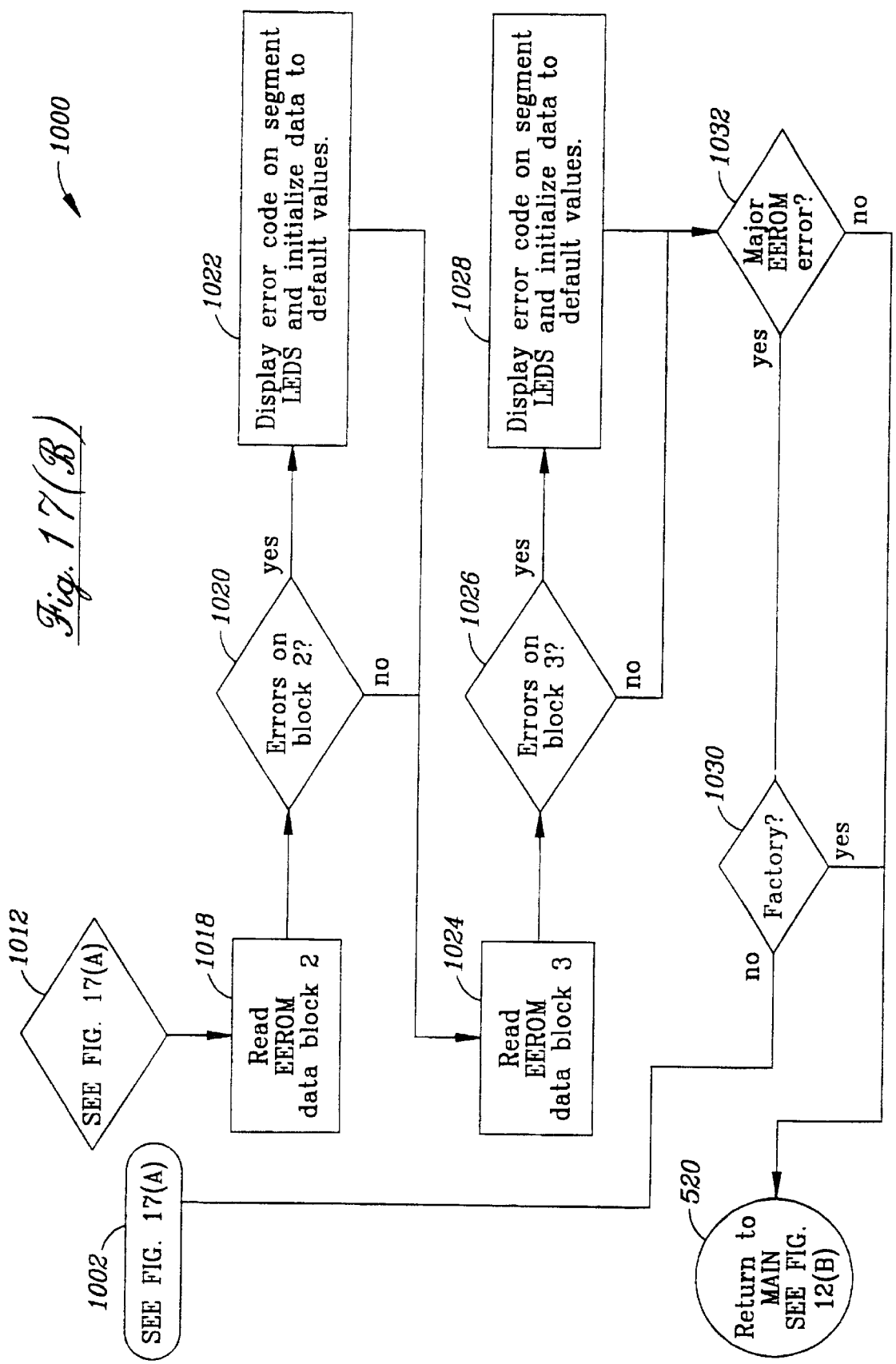

FIG. 17 is composed of FIGS. 17(A) and 17(B) comprised of various program segments arranged as shown therein. The main board process read EEROM data blocks routine 1000 has an initial program segment 1002 which signifies that the routines 1000 are entered in from the main board process of FIG. 12 at the time of initialization, that is, as shown in FIG. 12(B). Essentially the routines 1000 read EEROM data blocks 0, 1, 2, and 3 and analyze to detect their correctness and if errors are detected display a corresponding error code on corresponding LEDs and initialize the related data to the default values. The EEROM data blocks 0, 1, 2 and 3 may be desired positions of the dental chair and related error thereof may be included in their contents and result in the need to display the errors. As seen in FIG. 17(B) after the program segment 1000 is complete (program segment 1030 or 1032) control is passed back to program segment 520 seen in FIG. 12(B). As seen in FIG. 12(C) main board process 500 also acts to pass control to the communication routines 1100 which may be further described with reference to FIG. 18.

Figure 18A:
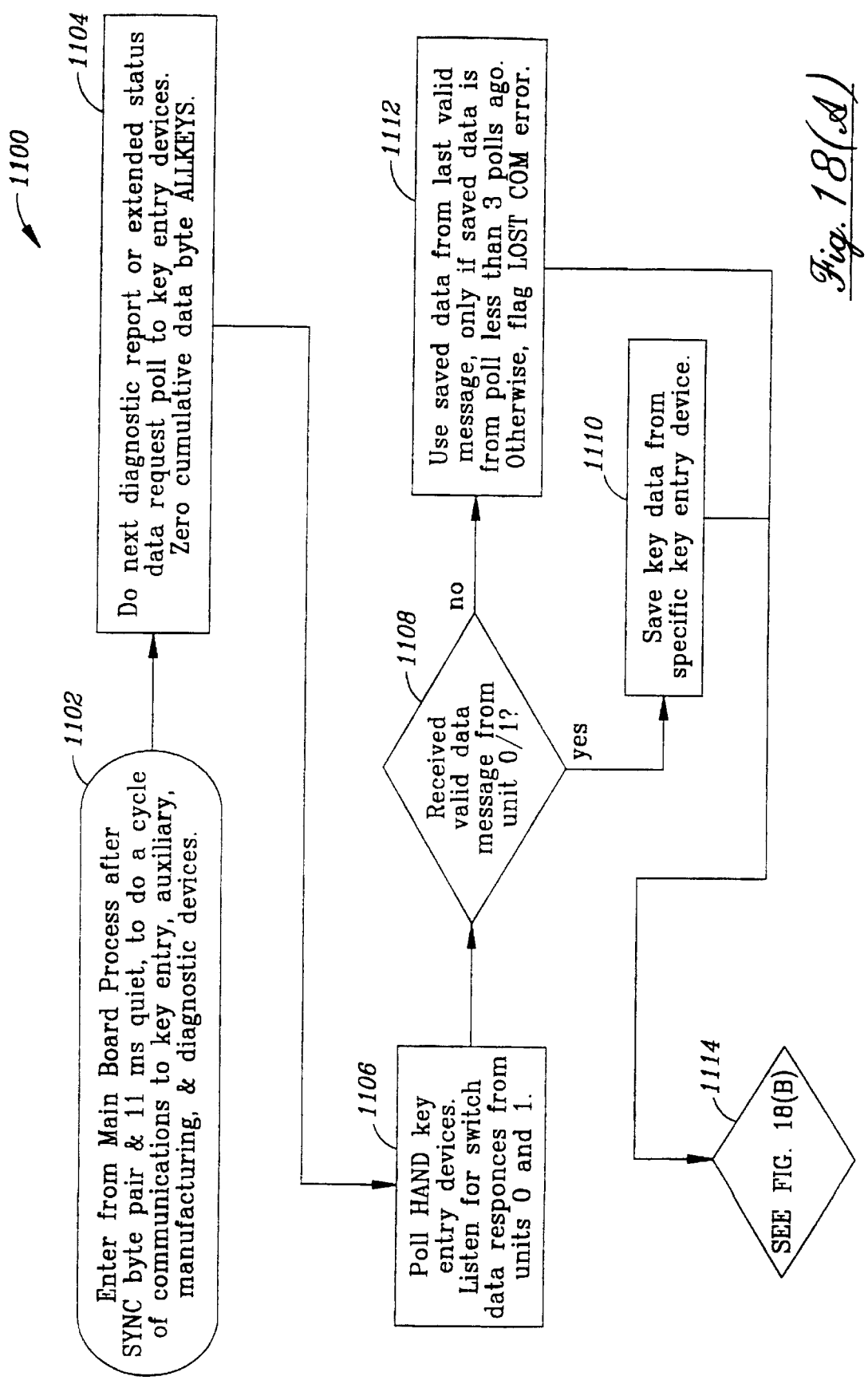
FIG. 18 is composed of FIGS. 18(A), 18(B) and 18(C) that cumulatively illustrate the flow chart of the main board process communications of the present invention.
Figure 18B:
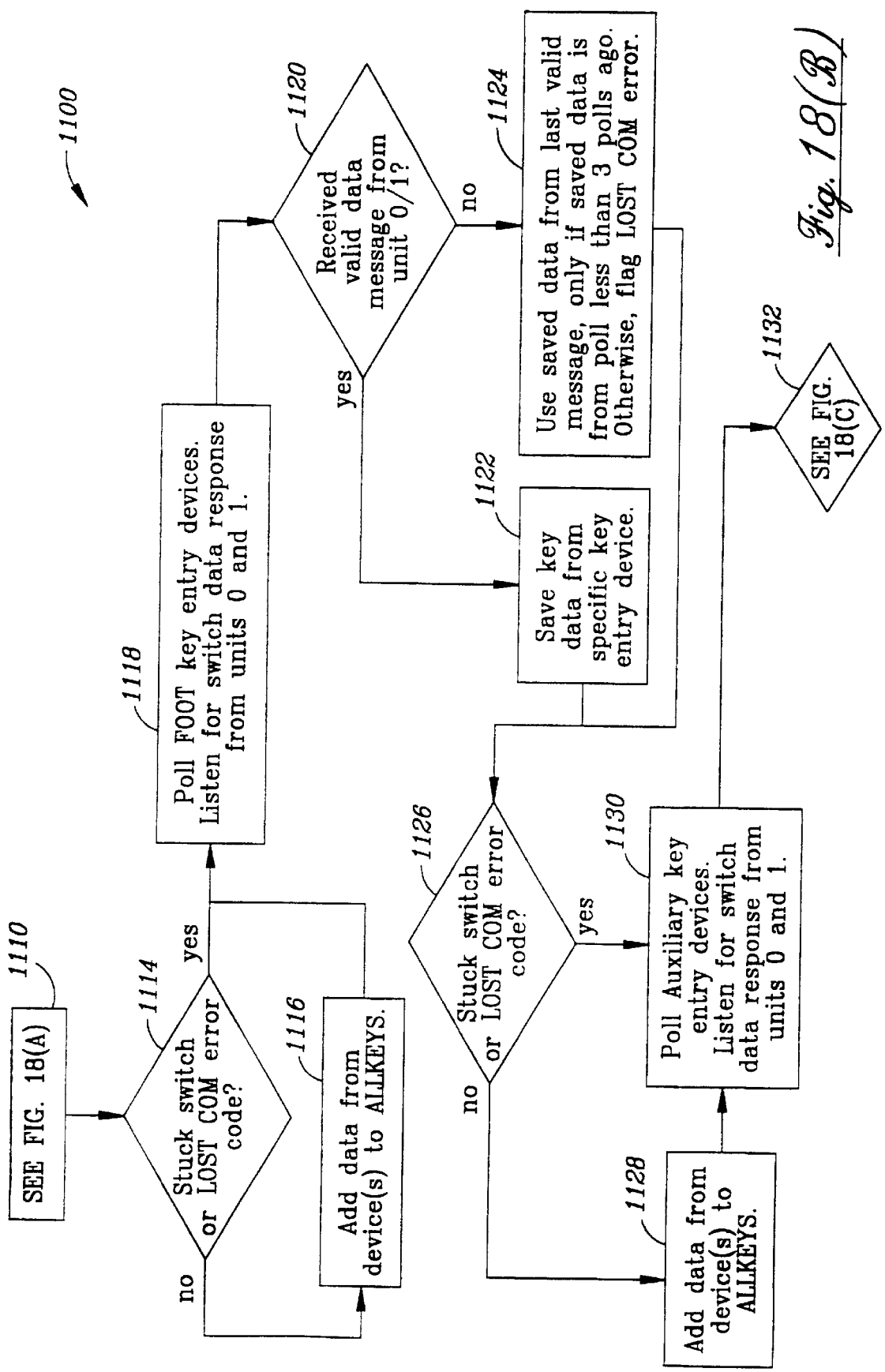
Figure 18C:
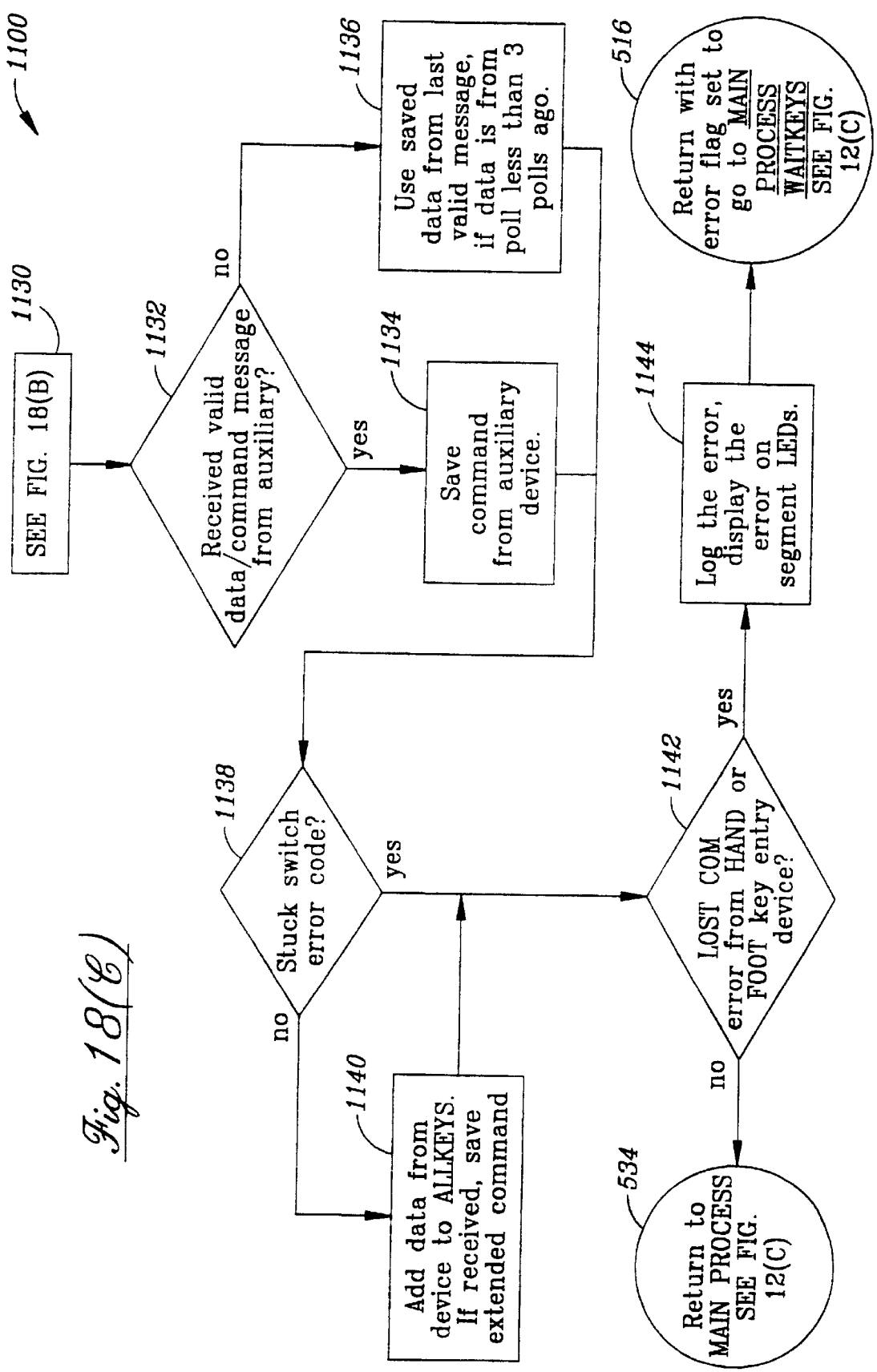

FIG. 18 is composed of FIGS. 18(A), 18(B), and 18(C) all of which cumulatively illustrate the main board process communication routine 1100 having an initial program segment 102 whose remarks point out that the routine 1100 is entered into from the main board process of FIG. 12 after the sync byte pair, used to maintain synchronization of all the devices communicating via the serial communication bus 40, and an 11 milliseconds quiet event have occurred or the routine 1100 is entered into to do a cycle of communication to a key entry to be described with reference to FIG. 20, auxiliary keys, and manufacturing and diagnostic devices such as, the diagnostic monitor 19 of FIG. 1. Program segment 1102 passes control to program segment 1104.

Program segment 1104 performs the next diagnostic report or extended status data request poll to key entry devices and sets the cumulative data byte for the ALLKEYS flag to 0, and then passes control to program segment 1106 which polls the hand key entry devices and determines the response of a data from units 0 or 1 associated with the selected keys, previously described with reference to FIG. 11, and then passes control to program segment 1108.

Program segment 1108 determines if the data from units 0 and 1 are valid and if valid passes control to program segment 1110 and conversely, if invalid, passes control to program segment 1112.

Program segment 1110 saves the data from the specific key entry device polled by program segment 1106 and verified by program segment 1108, whereas program segment 1112 saves the data from the last valid message but only if the saved data is from a poll less than 3 polls ago, otherwise, raises the program flag LOST COM errors. More particularly, the saved valid data was obtained less than three polling cycles ago of program segment 1106 being activated. Program segments 1110 and 1112 both pass control to program segment 1114 shown in FIG. 18(B).

Program segment 1114 determines if the data it receives is related to a stuck switch or possesses a LOST COM error code, and if either determination yields a no answer, program segment 1114 passes control to program segment 1116 which adds the valid data to ALLKEY information and then passes control to program segment 1118 which also receives control from program segment 1114 if the data program segment 1114 receives is indicative of an error.

Program segment 1118 polls the foot key entry devices of FIG. 10 and monitors for the switch data response from unit 0 and 1, previously discussed with reference to FIG. 11, and passes control to program segment 1120.

Program segment 1120 determines if the data received from program segment 1118 are valid, and if yes, passes control to program segment 1122 and, conversely, if the data are invalid, passes control to program segment 1124.

Program segment 1122 saves the data from the specific foot key entry device, and conversely, program segment 1124 uses saved data from the last valid message but only, in a manner similar to program segment 1112, uses the saved data if the last saved message is from a polling sequence which is less than 3 polling sequences ago, otherwise, program segment 1124 raises the flag LOST COM error. Again, the use of the saved data serves as a fault tolerant aspect that allows the present invention to discard erroneous data and continue with the desired process being performed. Program segment 1122 and 1124 both pass control to program segment 1126.

Program segment 1126 operates in a manner similar as program segment 1114, and if the received information is devoid of being indicative of a stuck switch or LOST COM error, passes control to program segment 1128 and, conversely, if program segment 1126 determines that the information is indicative of a stuck switch or includes the LOST COM error code, passes control to program segment 1130 that also receives control passed to it from program segment 1128. Program segment 1128 performs the tasks described for program segment 1116.

Program segment 1130 polls the auxiliary key switch devices and monitors for the switch data response on the serial communication bus 40 in a manner as previously described with reference to FIG. 11. Program segment 1130 then passes control to program segment 1132 of FIG. 18(C).

Program segment 1132 checks to see if the received information from program segment 1130 is a valid data/command message from the auxiliary switches and, if valid, passes control to program segment 1134 and, conversely, if invalid, passes control to program segment 1136.

Program segment 1134 saves the valid data/command message from the auxiliary device and, conversely, program segment 1136 uses the saved information from the last valid message if the data is from a poll that occurred less than 3 polls ago. Program segments 1134 and 1136 both pass control to program segment 1138.

Program segment 1138 determines if the information it received is indicative of a stuck switch and if so provides a stuck switch error code message. If the information is valid, program segment passes control to program segment 1140 and, conversely, if the information received is indicative of an error code, program segment 1138 passes control to program segment 1142.

Program segment 1140 adds the data it received from program segment 1138 to the ALLKEY contents and if it received an extended command also saves such, and when its subroutine is complete, passes control to program segment 1142.

Program segment 1142 determines if the information it received from program segments 1138 and 1140 includes a LOST COM error from hand or foot key entry devices and if no passes control to program segment 534 shown in FIG. 12(C). Conversely, if program segment 1142 did receive a LOST COM error from program segment 1138 then it passes control to program segment 1144 which logs the error, displays the error on the appropriate LEDs and then passes control to program segment 516 also shown in FIG. 12(C). Also shown in FIG. 12(C) is the command execution routines 1200 which may be further described with reference to FIG. 19 composed of FIGS. 19(A), 19(B) and 19(C).

The main board process execution routine 1200 makes reference to various terms, also referred to in FIG. 11, as well as others of FIGS. 12–26, primarily related to keys. More particularly, the routines 1200 make reference to WAITKEYS which is a command function used to stop chair motion and beep the speaker, and wait for a response from the operator indicative that he/she has let go of all of the keys he/she may have depressed. Similarly, the term ALLSTOP is used to stop chair motion, terminate any multiple hit key entry procedures and cause the speaker to be beeped once. Direct motion keys are those keys that may be used to provide direct motion to the dental chair so that it becomes base up, base down, back up and back down. The position entry keys have two position keys 0 and 1 defined. Dependent on the chair, multiple key presses within a brief period of time can be used to select positions 2, 3 and 4 of the chair. The positions 1, 2 and 3 may be predetermined configurations in which the dental chair is oriented favorable to the dentist in his/her treatment of the patient. In addition, when a learn key is held down continuously, multiple key pressers are used to verify the operator'intent to learn/change the remembered position for the selected position number, that is, selected position 2/3/4. If multiple keys have been depressed and their depression is not complete within a predetermined time or count of presses is determined to be incorrect for their intended command, the WAITKEYS flag is set. The occurrence of the WAITKEYS flag causes any chair motion to stop, and for the movement of the chair to wait for the operator to release all keys before allowing new action or motion to be initiated. Again, the practice of the present invention provides fault detection to safeguard the patient.

The main board process command execution routine 1200 has an initial program event 1202 which indicates that the main board process of FIG. 12 causes the entry into the routines 1200 after a successful main board process communication 1100 of FIG. 18. The main board process execution is also entered after key entry devices have been polled, the key data collected, and the desire to act upon such collected data is apparent. The program segment 1202 passes control to program segment 1204.

Program segment 1204 determines if any keys have been pressed, and if the answer is yes, passes control over to program 1206 which, in turn, checks for the flag for WAITKEYS and if present, returns control along with an error flag back to program segment 530 shown in FIG. 12(C). If there is no flag set for WAITKEYS, program segment 1206 passes control to program segment 1208.

Program segment 1208 also receives control from program segment 1210 which, in turn, receives control from program segment 1204 upon its determination that no keys are pressed. Program segment 1210 clears any flags for WAITKEYS and passes control to program segment 1208. Program segment 1208 evaluates the operator's use of the position keys, that is, whether they are pressed and then released or pressed twice quickly, and then passes control to program segment 1212 of FIG. 19(B).

Program segment 1212 determines if the key that was depressed is the LEARN key, and if not, passes control to program segment 1214 which, in turn, determines if the key that was depressed was a direct motion key. If the direct motion key was pressed, then program segment 1214 passes control to program segment 1216.

Program segment 1216 cancels any position motion of the chair that may be in process and sets the motion request to initiate the base/back, up/down as selected by the direct motion key provided that the chair is not commanded to move beyond its preset limits. Program segment 1216 then passes control to program segment 524 as shown in FIG. 19(C).

If program segment 1214 determines that the direct motion keys have not been depressed, then program segment 1214 passes control to program segment 1218 which determines if the entry received from program segment 1214 is a requested position move which is in progress and if the answer is no, program segment 1218 passes control to program segment 1220.

Figure 19A:
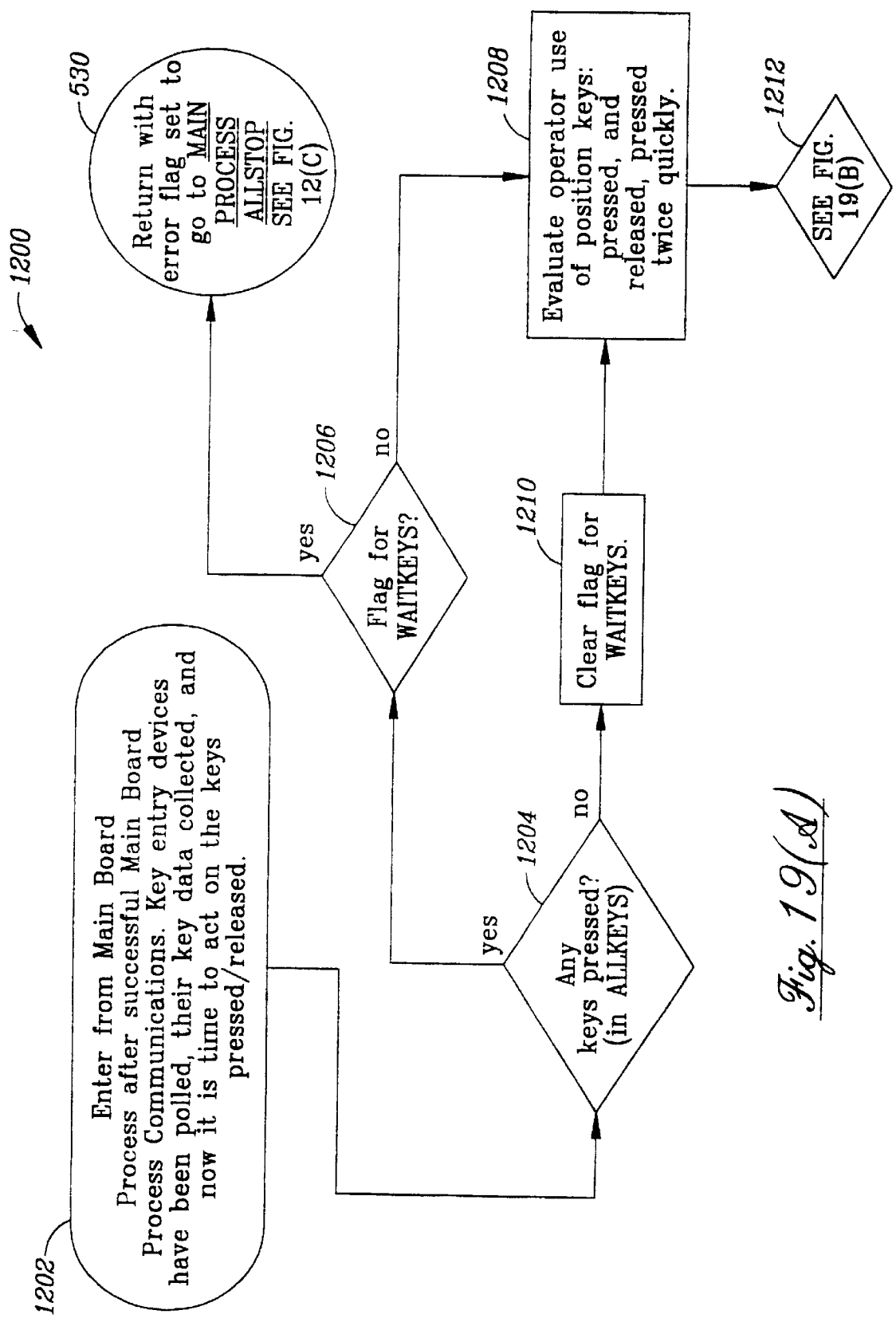
FIG. 19 is composed of FIGS. 19(A), 19(B) and 19(C) that cumulatively illustrate the flow chart of the main board process command execution of the present invention.
Figure 19B:
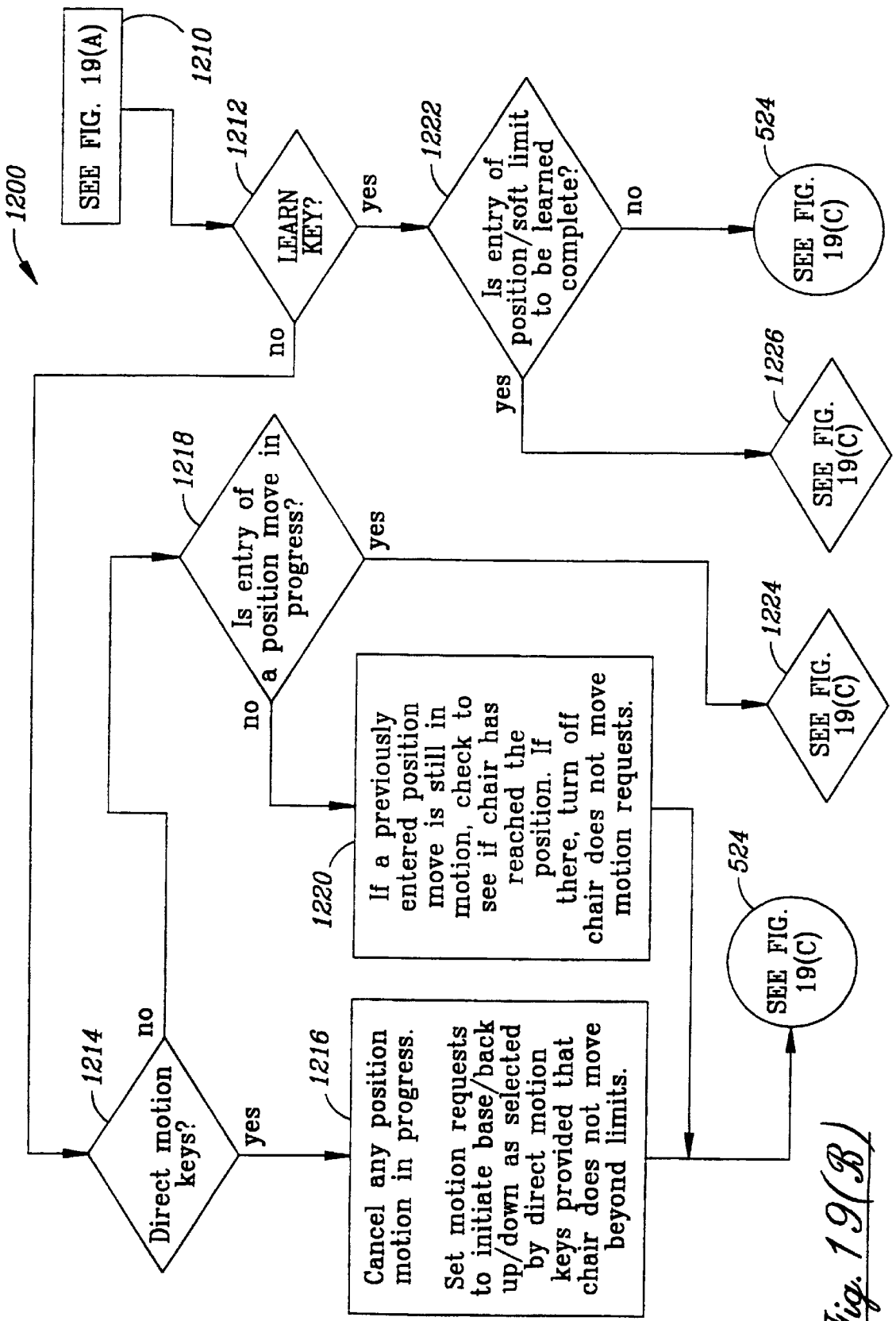
Figure 19C:
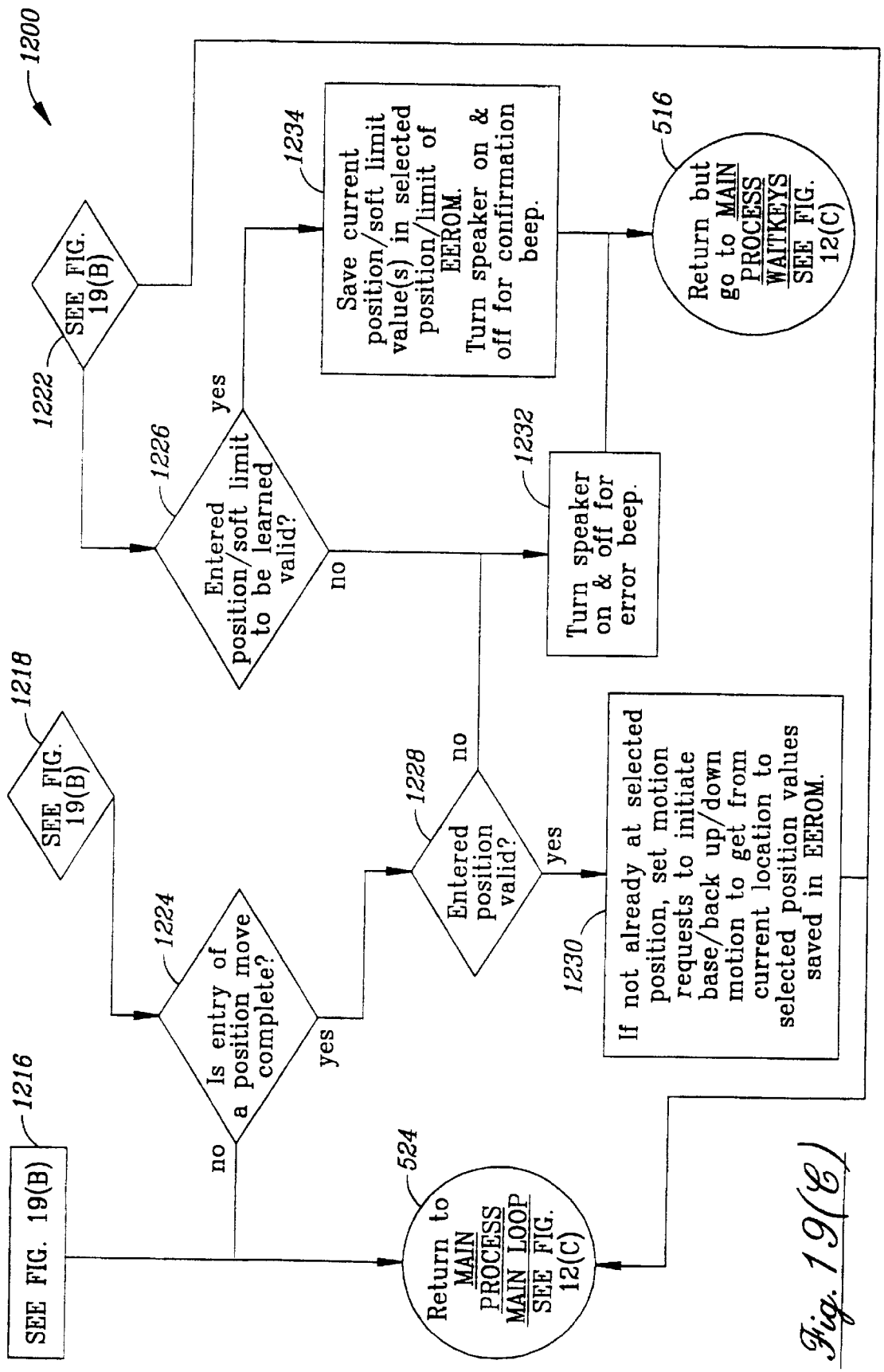

Program segment 1220 determines that if a previously entered position is still in motion, and if so, then checks to see if the dental chair has reached the requested position, and if at the requested desired position, turns off any further motion request and passes control to program segment 524 of FIG. 19(C). The movement of the dental chair is accomplished with cooperation of the main board process timer 1 routines 800 of FIG. 15. If program segment 1218 determines that a position move is in progress, it then passes control to program segment 1224 of FIG. 19(C).

With reference back to program segment 1212, if the LEARN key is depressed, program segment 1212 passes control to program segment 1222 which determines if the entry of the position/soft limit that is to be learned is completed. If the position/soft limit is complete then program segment 1222 passes control to program segment 1226 of FIG. 19(C) and, conversely, if the position/soft limit being learned is not complete, program segment 1226 passes control to program segment 524 of FIG. 19(C).

Program segment 1224 that receives control from program segment 1218 of FIG. 19(B) and determines if the entry of a position move has been completed, and if no, passes control back to program segment 1216 of FIG. 19(B). Conversely, if the entry of a position move has been completed, program segment 1224 passes control to program segment 1228.

Program segment 1228 determines if the entered position received from program segment 1224 is valid, and if valid, passes control to program segment 1230. Program segment 1230 determines if the valid position has already been selected and if so selects the motion request to initiate the base/back, up/down motion to get from the current position to the selected position and saves the selected position in the associated EEROM. Upon completion, program segment 1230 passes control to program segment 524 shown in FIG. 12(C).

With reference back to program segment 1222 of FIG. 19(B), if the LEARN key has been depressed and if the position/soft limit has been completely learned, program segment 1222 passes control to program segment 1226 of FIG. 19(C).

Program segment 1226 determines if the enter position/ software to be learned is valid and if not valid, passes control to program segment 1232 which turns the speaker X2 of FIG. 3 on and off indicative of an error beep, and then passes control to program segment 516 of FIG. 12(C)

If program segment 1226 determines that the enter position/soft limit is valid, then it passes control to program segment 1234. Program segment 1234 saves the current position/soft limit values in selected position/limit location of the EEROM and turns the speaker on and off for a sound to indicate a confirmative beep. Program segment 1234 then passes control to program segment 516 shown in FIG. 12(C). The switches, such as the LEARN switch related to program segment 1234 is read by a key entry process routine 1300 which may be described with reference to FIG. 20 composed of FIGS. 20(A), 20(B) and 20(C).

In general, the key entry process routine 1300 performs initial tests, the first of which is a key entry type in which the associated microprocessor needs to determine which physical type of key entry hardware is attached thereto. The microprocessor of concern has several lines that can be attached to key entry hardware. For example, for individual switches, one line is attached to one switch and some of the lines are not attached to anything, or membrane keypads, such as those preferably used in the present invention and given in Table 4 and cooperating with the microprocessor U301 of FIG. 10. In the membrane switches a line can be connected to about a 5 volt D.C. or 0 volt/ground. Each specific membrane keypad has a unique connection pattern. Identity of the membrane keypad type switch can be determined by setting different lines to output 0/5 volts and then reading the other lines input values.

The second initial test is that the key entry device needs to be detected by the associated microprocessor to determine if any of the switches are "stuck switches." If during an initial start-up time, the associated microprocessor detects that the keys are pressed, it is evaluated and classified as "stuck switches." It is assumed that a normal user does not use keys to try to operate the device within milliseconds of power up, so it is a relatively good assumption that the key entry hardware must be damaged. The "stuck switch" error code provided by the present invention is returned when a poll for data of a particular switch is requested so that the system 10 of the present invention knows enough to ignore keys pressed from that particular key device. Again, the present invention provides fault tolerance, that is, detecting an error but allowing the process to correctly continue. Extended status polls are used to report the actual reading of the keys so that diagnostic processors can evaluate the situation. In addition to the initial task, maintenance tasks are also performed.

The maintenance tasks are of the type that need to take place dependent upon the actual physical type of the key entry hardware that is attached to the associated microprocessor. Some key entry hardware needs more time to evaluate if a key is pressed or not. Some key entry hardware is "noisy" and requires several successive readings of the keys, all yielding the same value (commonly referred to as debouncing) for an accurate result. A task can be doing in one step while the next step is needed to be performed and could read a slower responding device or it could be the nth reading of a "noisy" device and the determination being that a good "debounce" value has been obtained.

The key entry process routines 1400 of FIG. 21 read individual switches as follows. First, all connection lines are used as input. If a 0 is read, the switch is assumed to be depressed, connecting the input line to a 0 volt/ground. If a 1 is read, approximately 5 volts, the switch is not assumed to be pressed and the line is floating high. Membrane switches are read using a basic matrix scan known in the art. Some connection lines are used as line drivers and some are used as input sensor lines. One at a time, a drive line is set to 0. If one of the membrane key pad switches is pressed, a sensor line will read a 0 value instead of a 1 from a 5 volt floating value. Each combination of 1 drive line and one sense line defines a potential "key" location. Assignment of the drive lines, sense lines and the position of each key function depends on which membrane keypad is connected to the key entry device associated with the microprocessor at any one time.

In the overall operation data collision may occur. Data collision is meant to mean that multiple key entry devices are putting different data on the serial communication bus 40 at the same time. This situation can be detected on newer hardware software revision key entry devices as follows. The serial communication bus 40 is driven to 0 for a 0 data on the serial communication bus 40 and allowed to float high to approximately 5 volts for a 1 data bit. When the key entry device is "transmitting" a 1 data bit, the operating program monitoring the serial communication bus 40 detects if another device has driven the serial communication bus 40 to a 0 value. Detecting the 0 when transmitting a 1, detects data collision by another key entry device.

If desired, an alternate hardware software key entry device can be used to avoid data collision by two different variations 1 and 2. In variation 1, a fixed 1 or 0 can be used for unit assignment based on right vs. left handedness of the device dependent upon its location and usage on the dental chair. Only one left and one right handed device is allowed in the system. In variation 2, it may start out with the use of a device as unit 1 listening or monitoring the serial communication bus 40 for unit 0 to respond before its response occurs. If two devices transmit a message equivalent to "no keys pressed" i.e., 0 data bits at the same time, no conflict occurs because no action is requested. The first device to have a switch pressed becomes unit 0. The second unit hears (via the associated operating routines) the first unit responding as unit 0 and so decides to remain unit 1.

FIG. 13 is composed of FIGS. 13(A), 13(B) and 13(C) all of which cumulatively illustrate the key entry process routine 1300 as having an initial program segment 1302. The key entry process 1300 has an initialization process which is the same as the initialization process previously described with reference to FIG. 12. More particularly, the initialization process for a key entry process 1300 comprises program segments 1302, 1304 and 1306 which is equivalent to program segments 502, 504 and 506 respectively previously described. The initialization process is performed on both the microprocessors U101 (FIG. 5) and U301 (FIG. 10) each of which contributes to the servicing of the switches used for the operation of the dental chair. Moreover, the initialization segment for the key entry process 1300 further includes program segment 1310 which initializes the internal storage of the microprocessors U101 and U301, but unlike the program segment 508 for the main board process 500, does not initialize the input/output interfaces nor start the timer 0 and 1 interrupt processors. The program segment 1310, upon completion, passes control to program segment 1308 which monitors the serial communication bus 40 to determine if any communications between the microprocessors of FIGS. 1–10 has been established and then passes control to program segment 1312.

Program segment 1312 detects if a byte has been received, that is, the sync byte previously discussed with reference to program routines 500. If such occurs, the program segment 1312 passes control to program segment 1314 of FIG. 20(B) and, conversely, if no sync byte is received then program segment 1312 passes control to program segment 1316 also of FIG. 20(B).

Program segment 1316 determines if a maintenance task needs to be performed and if so identifies the initial unit 0 or 1 that is assigned for the testing and upon completion passes control to program segment 1332 of FIG. 20(C).

Program segment 1314 receiving information from program segment 1312 determines if a sync byte is present, and if not, passes control to program segment 1318 which, in turn, determines if fewer than 15 sync byte pairs have been received and if the answer is yes, passes control of the program segment 1332 of FIG. 20(C) and, conversely, if the answer of program segment 1318 is no, passes control to the communication routines 1100 previously discussed with reference to FIG. 18.

If program segment 1314 determines that a sync byte is present, then program segment 1314 passes control to program segment 1320 which, in turn, monitors the serial communication bus 40 to determine if a second sync byte is present thereon and measures the time between bit transitions thereof and upon completion passes control to program segment 1322 of FIG. 20(C).

Figure 20A:
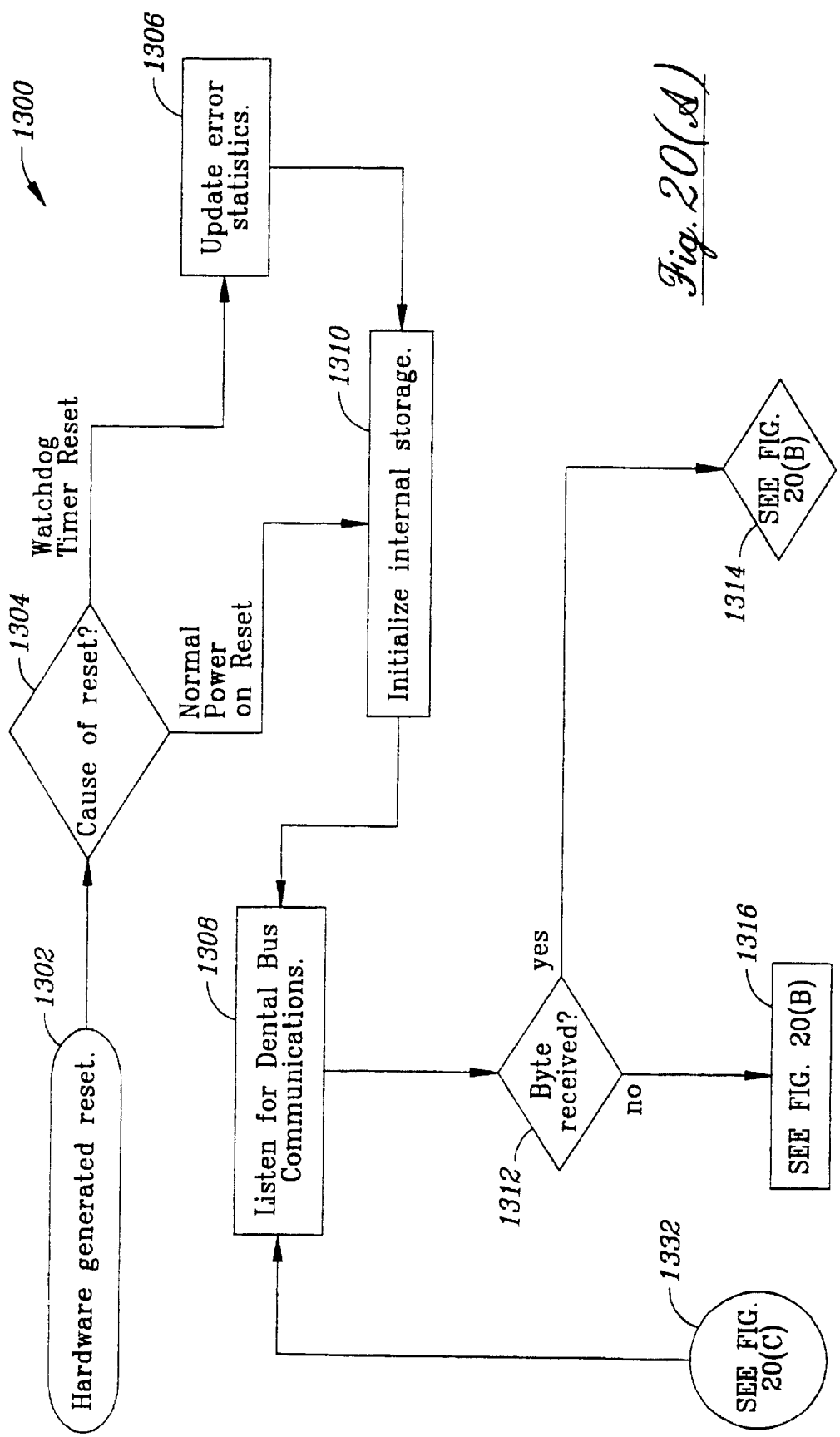
FIG. 20 is composed of FIGS. 20(A), 20(B) and 20(C) that cumulatively illustrate the flow chart of the key entry process of the present invention.
Figure 20B:
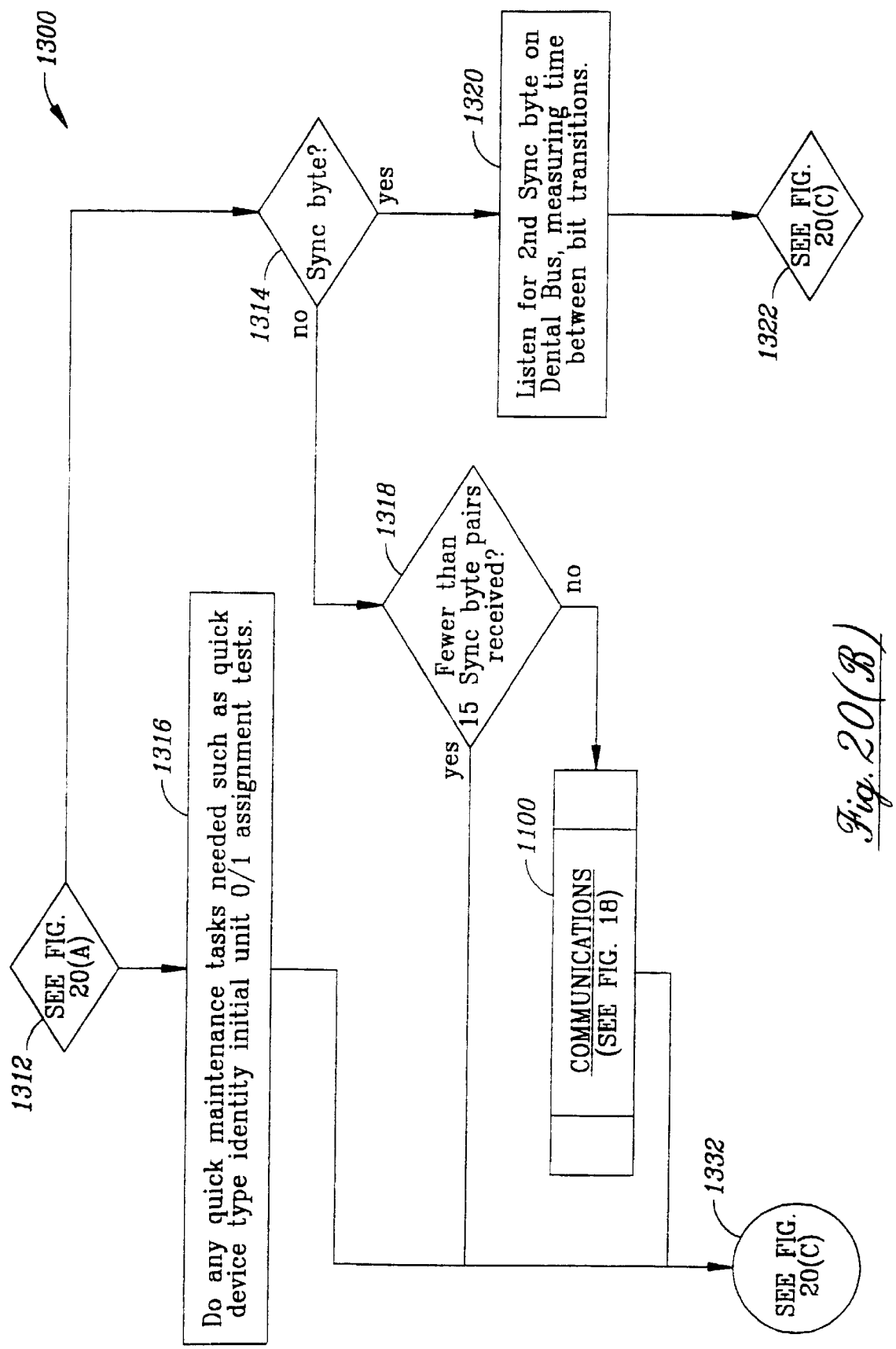

Program segment 1322 monitors for the second byte that is received to determine if such was not a sync byte, and if the detection of program segment 1322 yields an answer of yes, then program segment 1322 passes control to program segment 1332 which, in turn, passes control back to program segment 1308 of FIG. 20(A). If program segment 1322 determines that the second byte received was not a sync pulse then it passes control to program segment 1324.

Program segment 1324 adjusts the baud rate if it is different than that of the main board process 500 described with reference to FIG. 12 and also determines if any maintenance tasks are necessary, and upon completion, program segment 1324 passes control to program segment 1326.

Program segment 1326 determines if fewer than 15 sync byte pairs have been received, and if yes, passes control to program segment 1328 and, conversely, if no, passes control to program segment 1330.

Program segment 1328 determines if the initial task may be of the complex type and also determines if the initial unit is 0 or 1, and if any stuck switch errors have been detected, and then passes control to program segment 1330.

Program segment 1330 does nothing until a total of 10 milliseconds have passed after the receipt of the second sync determines by program segment 1322, and after such time has passed, passes control to program segment 1332 previously described. If a sync byte has been received as determined by the routines 1300 of FIG. 20, then the key entry process communication routine 1400 is entered into and may be further described with reference to FIG. 21 composed of FIGS. 21(A) and 21(B).

The key entry process communication routine 1400 has an initial program segment 402 whose remarks state that the routine 1400 is connected from the key entry process 1300 of FIG. 20 when a byte has been received and it is not a sync byte. More particularly, more than 15 sync byte pairs have been received, the baud rate has been initialized, and other start up statistics have been initialized. Program segment 1402 passes control to program segment 1404.

Figure 21A:
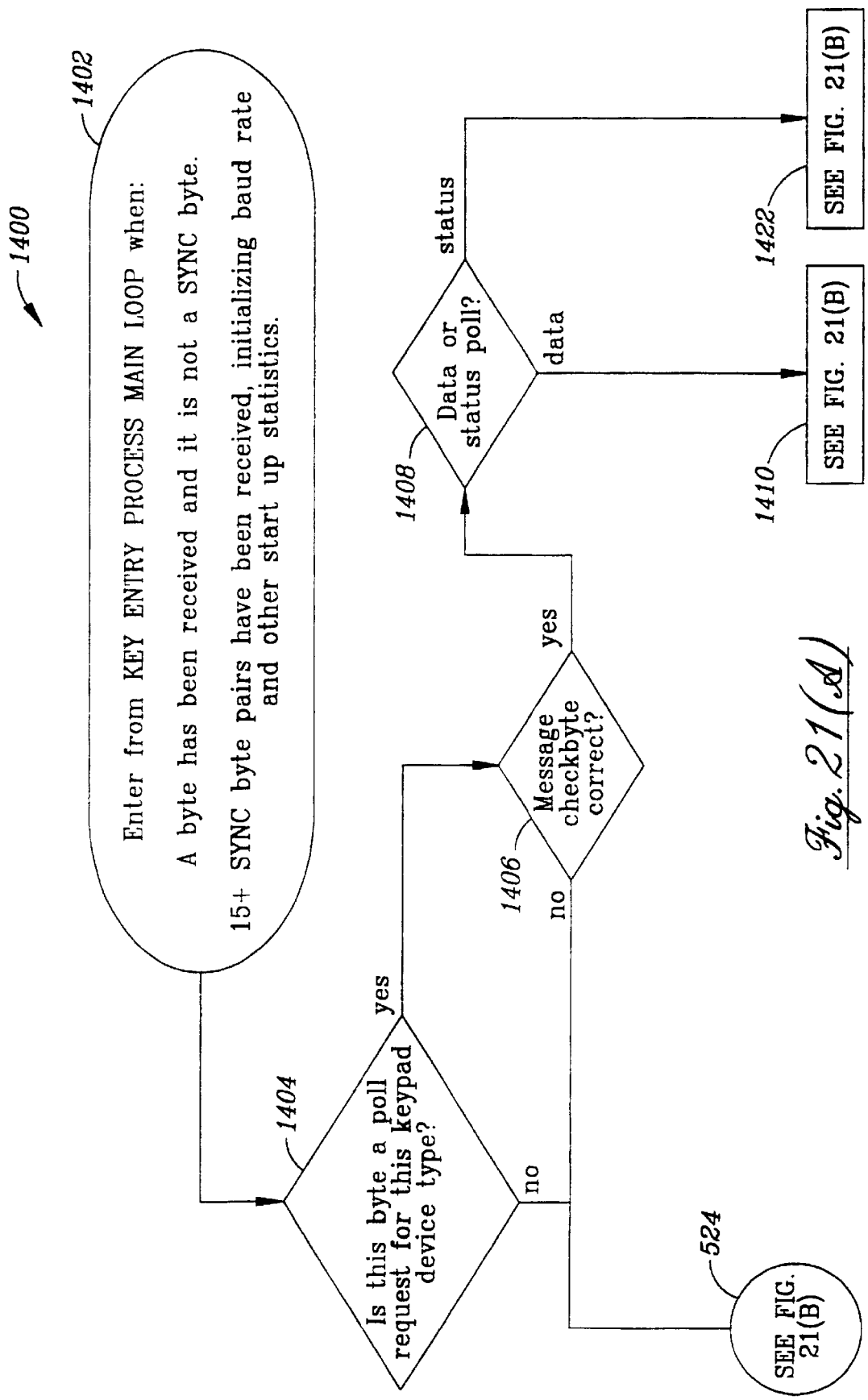
FIG. 21 is composed of FIGS. 21(A) and 21(B) that cumulatively illustrate the flow chart of the key entry process communications of the present invention.
Figure 21B:
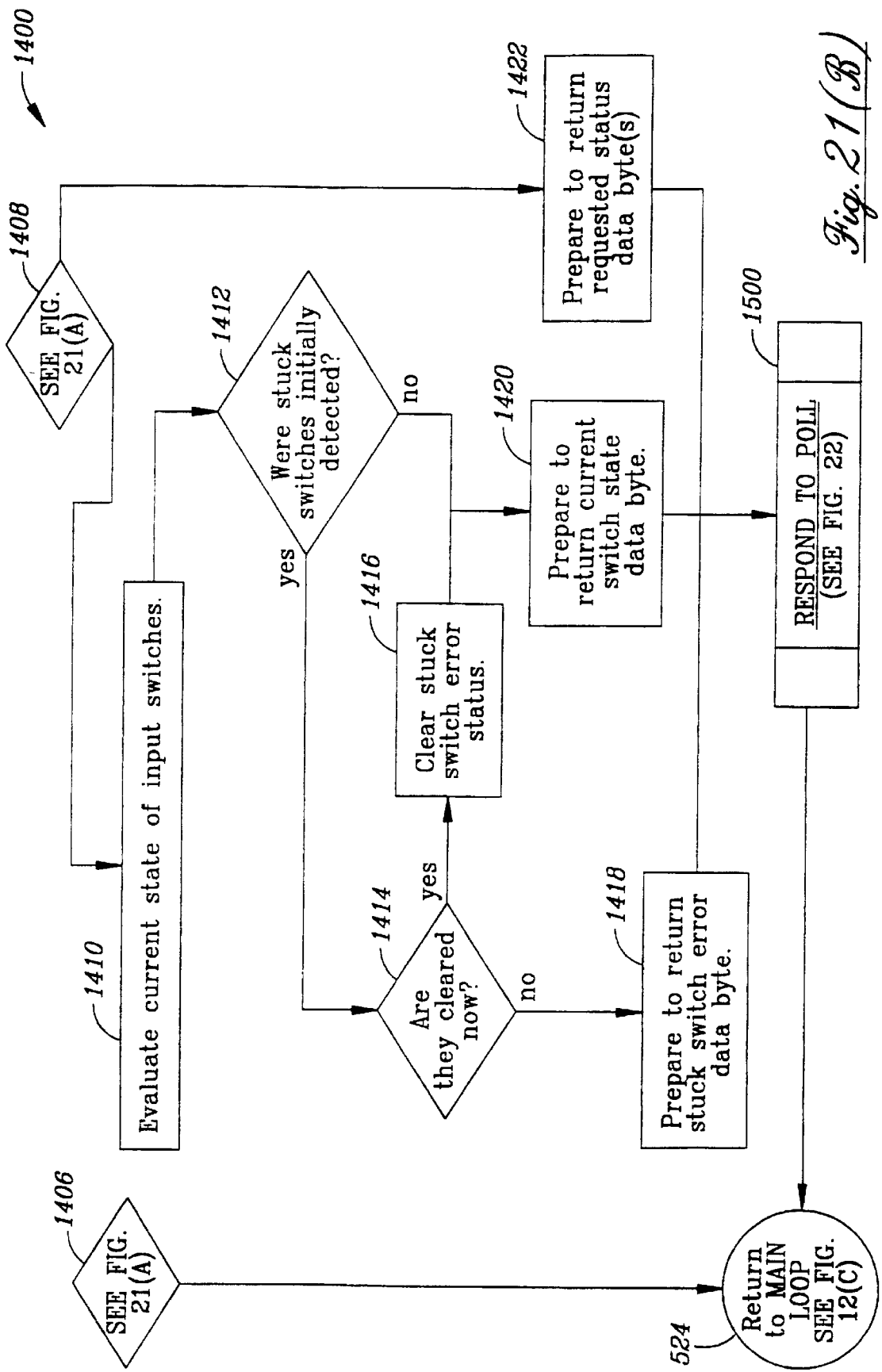

Program segment 1404 determines if the received byte is a poll request for a particular keypad device, and if so, passes control to program segment 1406 and, conversely, if not, passes control to program segment 524 shown in FIG. 21(B). Program segment 1406 checks the correctness of the message it received (again performing another self-check diagnostic routine for a remote device) and if correct, passes control to program segment 1408 and, conversely, if incorrect, passes control to program segment 524 of FIG. 21(B).

Program segment 1408 determines if the received message is a data or status poll type request, and if a data request, passes control to program segment 1410 of FIG. 21(B) and, conversely, if status request passes control to program segment 1422 also of FIG. 21(B).

Program segment 1410 evaluates the current state of the input switches and then passes control to program segment 1412.

Program segment 1412 checks the input switches to determine if any switches were stuck switches. If any switches have been detected as being stuck, program segment 1412 passes control to program segment 1414 and, conversely, if no stuck switches have been detected, program segment 1412 passes control to program segment 1420.

Program segment 1414 verifies that all the stuck switches are now clear, and if yes, passes control to program segment 1416 which clears stuck switch error status and then passes control to program segment 1420. Conversely, if the stuck switches have not been cleared, program segment 1414 passes control to program segment 1418 which prepares and returns a stuck switch error data byte back onto the serial communication bus 40 to be responded to by the receiving unit so that the data of the stuck switch is ignored.

Program segment 1420 passes control to program routines 1500 which are the key entry process respond to poll routine and may be further described with reference to FIG. 22.

The key entry process respond to poll routine 1500 has an initial program segment 1502 whose remarks state that the key entry process respond to poll routine 1500 is entered into under key entry process communication routines 1400 when a valid poll message for a particular device of interest has been heard or detected on the serial communication bus 40. Program segment 1502 passes control to program segment 1504.

Program segment 1504 detects if keys are pressed and if the answer is yes, passes control to program segment 1506 and, conversely, if the answer is no, passes control to program segment 1508.

Program segment 1506 determines if another unit that has responded has been detected on the serial communication bus 40 as unit 0. If the answer is no, program segment 1506 passes control to program segment 1510 which, in turn, designates the unit as unit 0 and then passes control to program segment 1508. If program segment 1506 detects that another unit has responded as unit 0 then it passes control to program segment 1508.

Figure 22A:
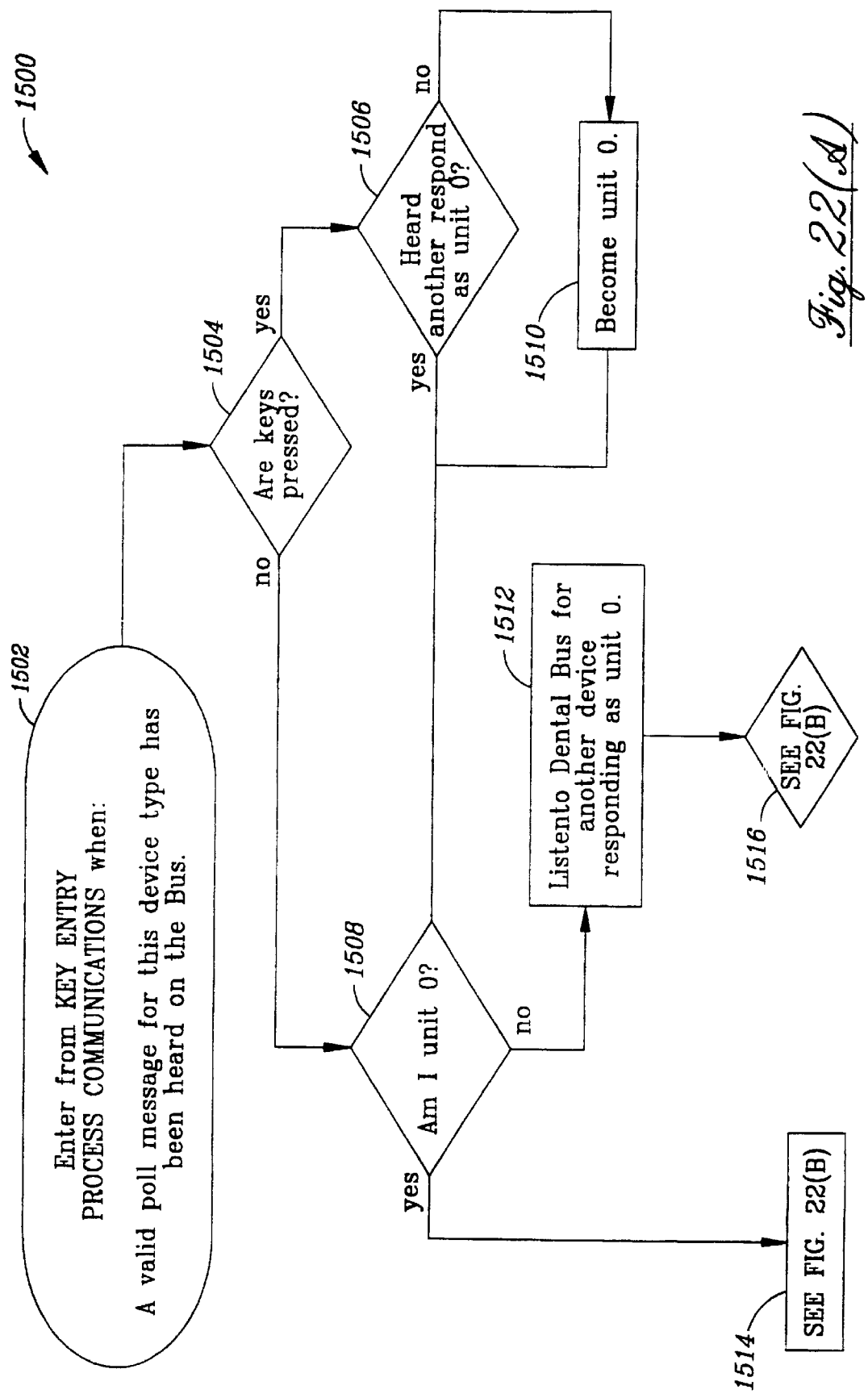
FIG. 22 is composed of FIGS. 22(A) and 22(B) that cumulatively illustrate the flow chart of the key entry process response to polling requests by the main board process of the present invention.
Figure 22B:
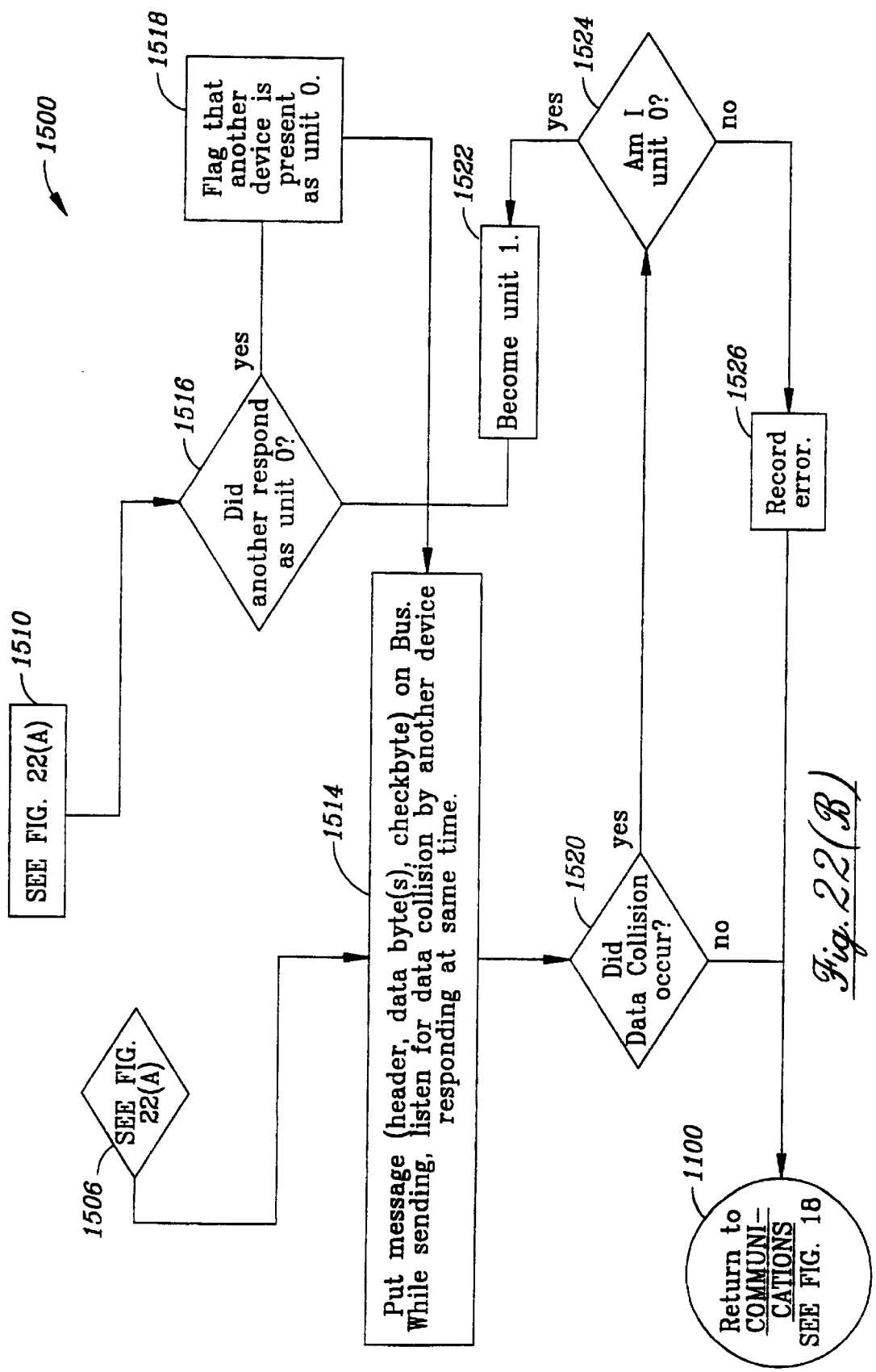

Program segment 1508 detects if the responding unit is 0, and if so, passes control to program segment 1514 of FIG. 22(B) and, conversely, if no, passes control to program segment 1512 of FIG. 22(A) which, in turn, listens or monitors the serial communication bus 40 for another device responding as unit 0, and then passes control to program segment 1516 of FIG. 22(B).

Program segment 1516 determines if another unit has responded as a unit 0, and if the answer is yes, program segment 1516 passes control to program segment 1518 which provides an error flag that another device is already present as unit 0 and passes control to program segment 1514. Program segment 1516 if detecting another that did not respond as unit 0, passes control to program segment 1522 so that the detected unit becomes unit 1.

Program segment 1514 upon receiving the information from program segments 1506 and 1518, puts a message on the serial communication bus 40 comprising header, data bytes, and check bytes and while sending such a message, listens or monitors for any data collision, previously described, caused by another device responding at that same time. Program segment 1514 then passes control to program segment 1520.

Program segment 1520 determines if any data collision has occurred and if so passes control to program segment 1524 and, conversely, if no data collision has occurred passes control back to communication routine 1100 of FIG. 18.

Program segment 1524 determines if the information that it receives is associated with unit 0 and if so passes control back to program segment 1522 and, conversely, if no, passes control to program segment 1526 which records the error and then passes control to communication routine 1100 of FIG. 18.

All of the programs described with reference to FIGS. 11–22 cooperate with logic elements of power supply 16 previously described with reference to FIGS. 6, 7, 8 and 9. As previously mentioned, the diagnostic monitor 19 of FIG. 1 may supply power via the dental bus 40 (V Bus) to power supply 16, as well as devices 12, 14 and 18 of FIG. 1, to activate the control electronics of all the distributed processors in the absence of power from the control circuitry 12. The power supply 16, activated by either the control circuitry 12 or the diagnostic monitor 19, has an operating routine power supply process routine 1600 which may be further described with reference to FIG. 23 composed of FIGS. 23(A), 23(B) and 23(C).

The power supply process routine 1600 resides in the microprocessor U202 of FIG. 8 and has an initializing procedure comprised of program segments 1602, 1604, 1606, and 1608, which are substantially the same as program segments 1302, 1304, 1306, and 1310 of the key entry process 1300 previously described. Program segment 1608 passes control to program segment 1612.

Program segment 1612 checks to see if there has been a lost communication flag error set and if yes, passes control to program segment 1614 which notes the flag and drives the appropriate LED light off and then passes control to program segment 1616 that also has control passed to it from program segment 1612 if the lost communication flag had not been set. Again, the practice of the present invention provides a fault detection by one microprocessor of the operation of another remote microprocessor.

Figure 23A:
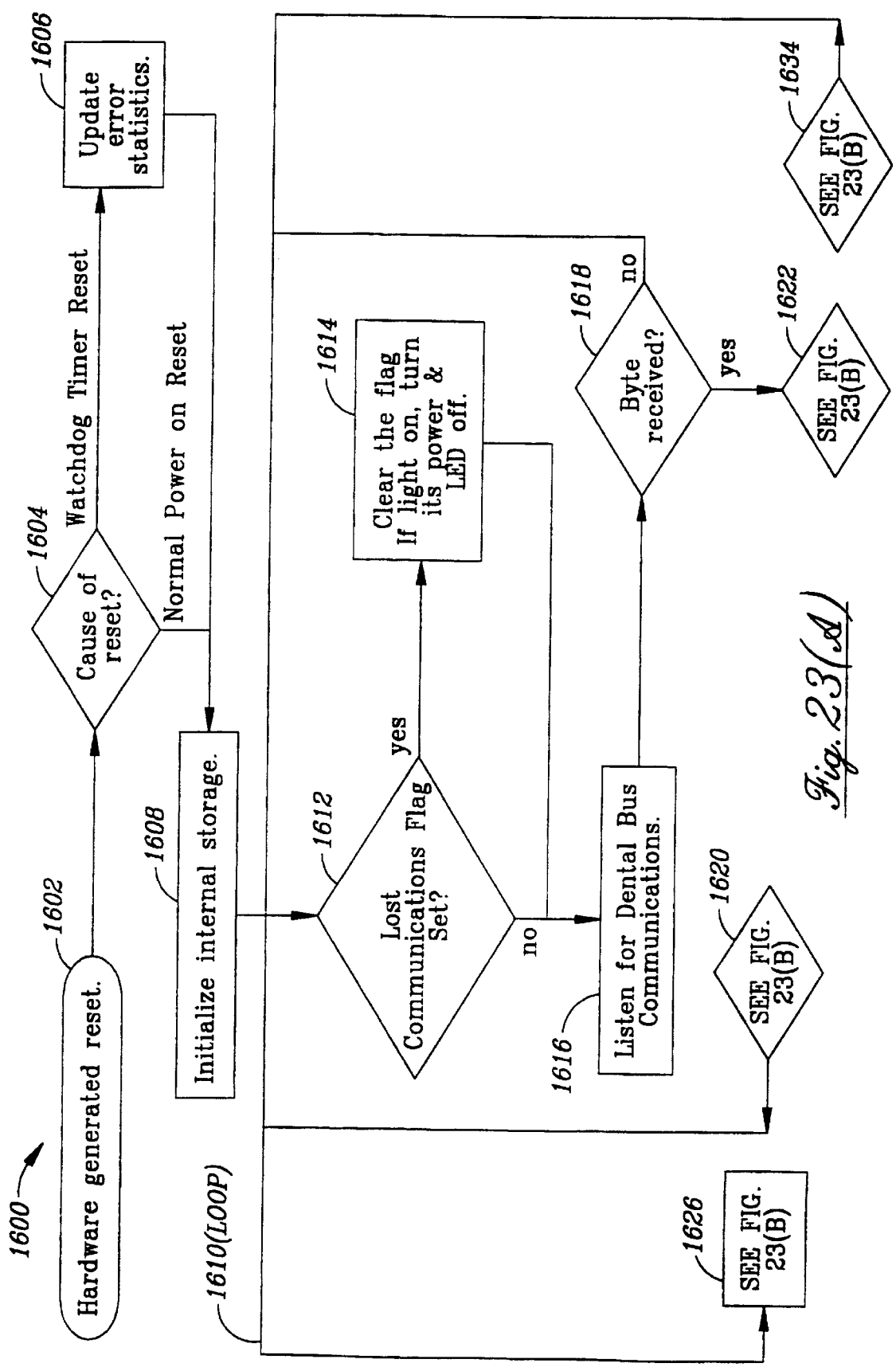
FIG. 23 is composed of FIGS. 23(A), 23(B) and 23(C) that cumulatively illustrate the flow chart of the power supply process of the present invention.
Figure 23B:
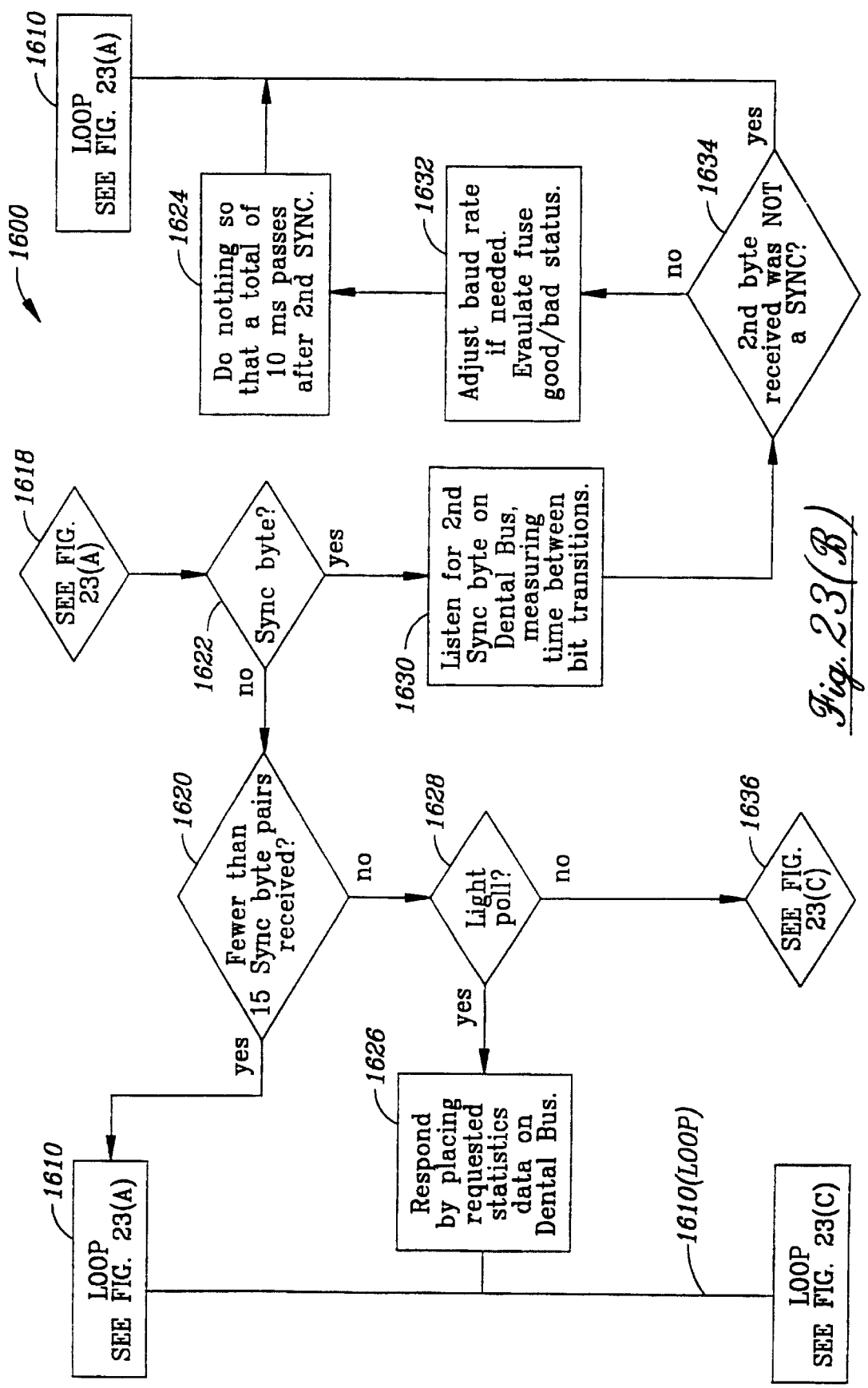

Program segment 1616 monitors the serial communication bus 40 for the occurrence of data (communications) from the connected microprocessors of FIGS. 1–10 and passes control to program segment 1618 which, in turn, monitors for the occurrence of a byte and if such a byte is not received, passes control to loop 1610, but if a byte is received, passes control to program segment 1622 of FIG. 23(B).

Program segment 1622 determines if a sync byte has been received, and if no, passes control to program segment 1620 which, in turn, determines if fewer than 15 sync byte pairs have been received, and if yes, passes control back to loop 1610 of FIG. 23(A), and if no, passes control to program segment 1628 which, in turn, checks to determine if the light related to the poll being performed is lit, and if the answer is yes, then passes control to program segment 1626 which, in turn, responds by placing the requested statistics data on the serial communication bus 40 and then passes control back to loop 1610. If program segment 1628 determines that the poll is not for an associated light, then control is passed to program segment 1636 of FIG. 23(C).

With reference back to program segment 1622, if a sync byte has been detected, program segment 1622 passes control to program segment 1630 which listens to detect if a second sync byte has occurred on the serial communication bus 40 by measuring time between bit transitions on the serial communication bus 40 and then passes control to program segment 1634.

Program segment 1634 determines if the second byte that was received by program segment 1622 was not a sync pulse, and if yes, passes control back to loop 1610 of FIG. 23(A) and, conversely, if no, program segment 1634 passes control to program segment 1632.

Program segment 1632 determines if the baud rate associated with the microprocessor U202 of FIG. 2 needs to be adjusted so as to conform to the main board baud rate and also program segment 1632 determines or checks the status of the fuses of FIGS. 1–10. Program segment 1632 upon completion, passes control to program segment 1624 which does nothing so that a total of 10 milliseconds may pass after the occurrence of the second sync byte and then program segment 1624 passes control to program segment 1610.

Figure 23C:
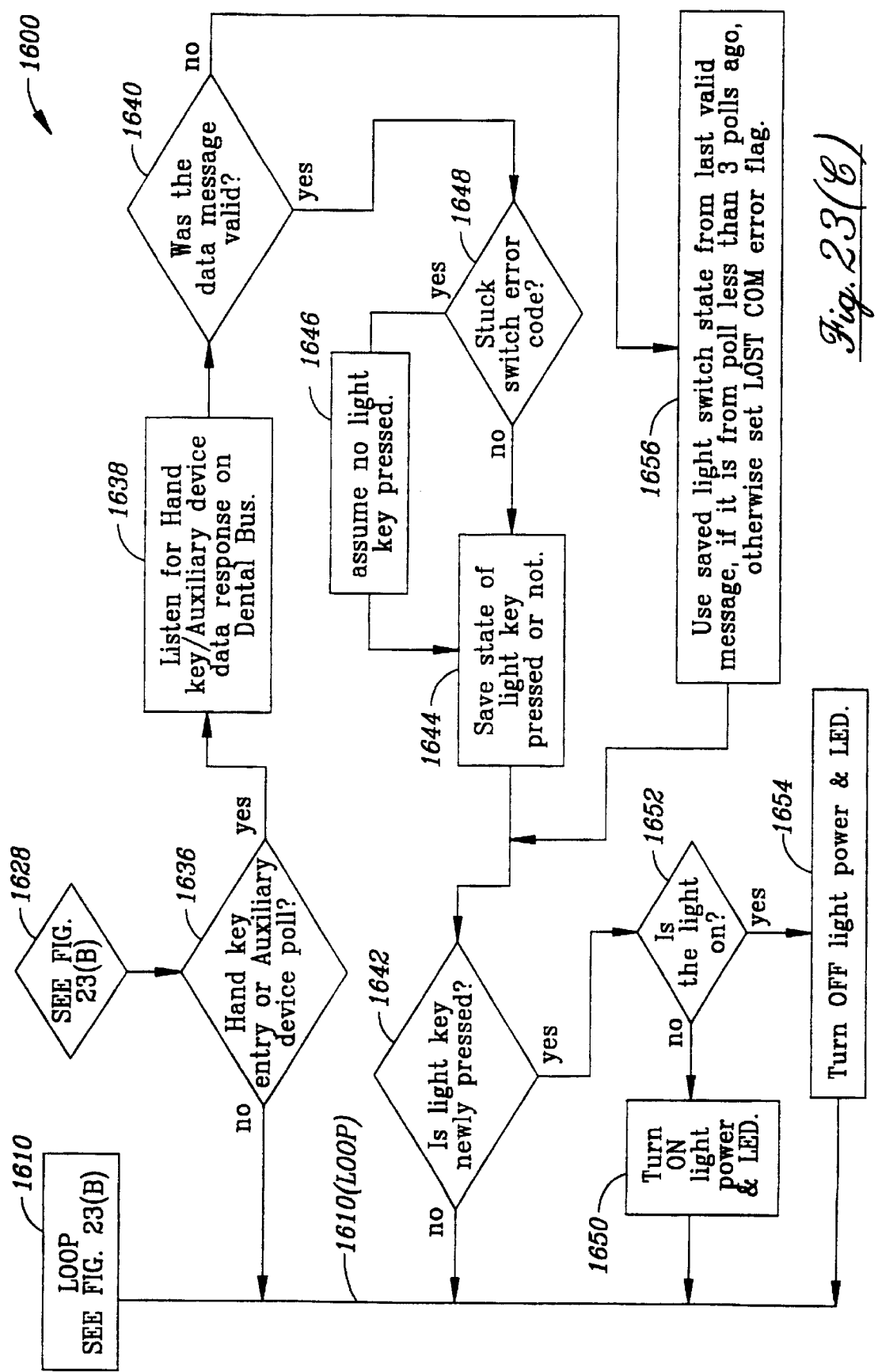

With reference back to program segment 1628 that passes control to program segment 1636 if a light is not applicable to the poll being serviced, program segment 1636 of FIG. 23(C) determines if the device is a hand key entry or auxiliary device poll. If neither of these inquiries are satisfied, program segment 1636 passes control back to loop 1610 and, conversely, if either of these inquiries is satisfied, program segment 1636 passes control to program segment 1638.

Program segment 1638 monitors or listens to the serial communication bus 40 to determine the presence of data indicative of a hand key or indicative of an auxiliary device and then passes control to program segment 1640.

Program segment 1640 determines if the monitored message that is received is valid, and if invalid, passes control to program segment 1656 which uses the saved light switch state from the last valid message if it is from a poll less than 3 polls ago, otherwise, sets the LOST COM error flag. If program segment 1640 detects that a valid message has been received, it passes control to program segment 1648.

Program segment 1648 determines if the message indicates a stuck switch error code, and if no, passes control to program segment 1644 and, conversely, if yes passes control to program segment 1646 which assumes no light key has been pressed which, in turn, passes control to program segment 1644.

Program segment 1644 saves the state of the light switch whether it is pressed or not, and then passes control to program segment 1642 which, in turn, determines if the light switch is a newly pressed light switch, and if no, passes control to the loop 1610 and, conversely, if the light switch is new, passes control to program segment 1652.

Program segment 1652 determines if the detected light is on, and if the answer is no, program segment 1652 passes control to program segment 1650 which, in turn, turns on the appropriate light power and the associated LED. If program segment 1652 determines that the light power is on, program segment 1652 passes control to program segment 1654 which turns off light power and the associated LED and passes control to the loop 1610 of FIG. 23(A) which, in turn, continues to loop until the power supply process 1600 is requested to again render its operation. The application and removal of power to the lights and LED determined by power supply process routine 1600 of FIG. 23, as well as the other routines of FIGS. 11–22 and 24–26, is be way of the interconnections shown in FIGS. 1–10.

The practice of the present invention provides for a serial parallel adapter process routine 1700 which is related to both the accommodation of an old board and a new board. The serial parallel adapter routine 1700 is the routine that allows each of the microprocessors U1, U101, U201 and U301 to communicate with the serial communication bus 40, sometimes referred to as the dental bus. The serial parallel adapter process 1700 may be further described with reference to FIG. 24 which is composed of FIGS. 24(A) and 24(B).

The serial parallel adapter process 1700 comprises an initialization segment composed of program segments 1702, 1704, 1706, and 1708 which is substantially the same as program segments 1302, 1304, 1306, and 1310, previously discussed with reference to FIG. 20. Program segment 1708 passes control to program segment 1712.

Figure 24A:
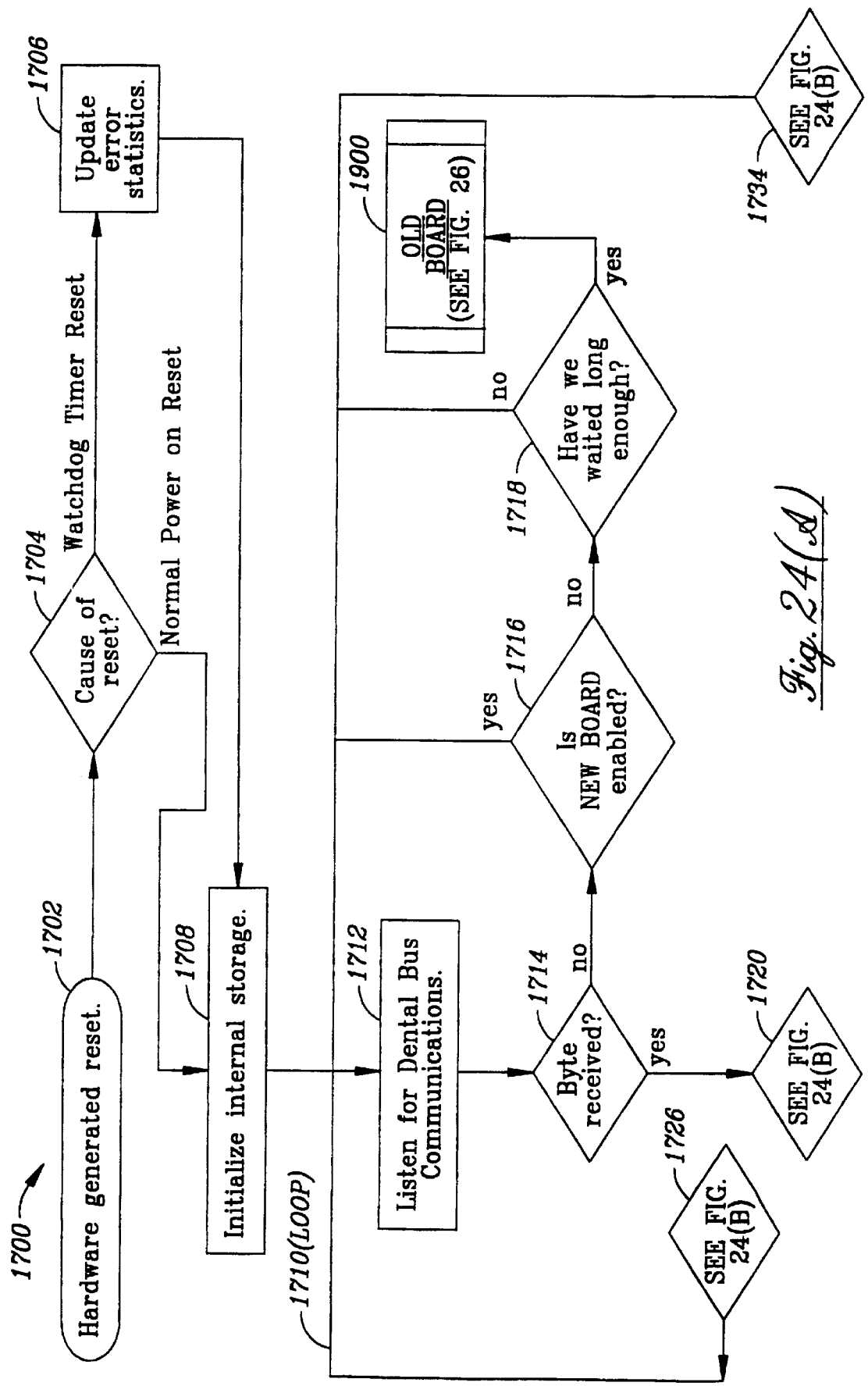
FIG. 24 is composed of FIGS. 24(A) and 24(B) that cumulatively illustrate the flow of the Serial/Parallel Adapter (SPA) process of the present invention.
Figure 24B:
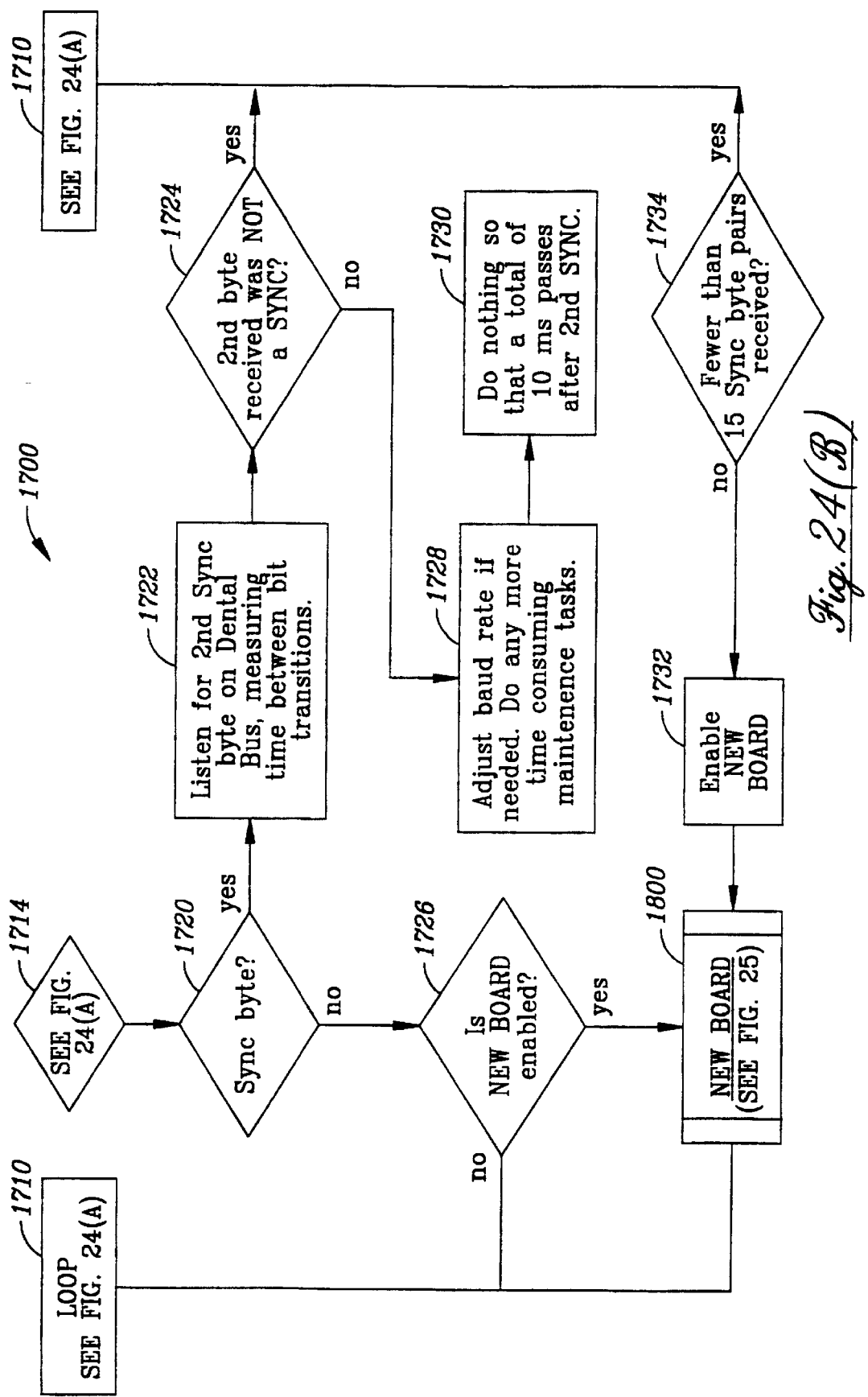

Program segment 1712 monitors the serial communication bus 40 to determine if any communications thereon is present and then passes control to program segment 1714 which monitors the serial communication bus 40 to determine if any byte has been received, and if so, passes control to program segment 1720 of FIG. 24(B) and, conversely, if no passes control to program segment 1716.

Program segment 1716 determines if a new board has been enabled, and if yes, then passes control back to the loop 1710 and, conversely, if no, passes control to program segment 1718.

Program segment 1718 determines if enough time has been allocated for the enabling of the new board. Program segment 1718 if detecting that enough time has not elapsed then passes control to loop 1710 and, conversely, if enough time has elapsed, passes control to old board program routine 1900 that is to be further discussed with reference to FIG. 26.

With reference to program segment 1720 of FIG. 24(B) that receives control from program segment 1714, program segment 1720 determines if a sync byte has occurred and, if yes, then passes control to program segment 1722.

Program segment 1722 monitors the serial communication bus 40 to detect if the second sync byte has occurred by measuring the time between bit transitions on the serial communication bus 40 and then passes control to program segment 1724 which, in turn, determines if a second byte has been received and whether it is a sync byte or not, and if the answer is yes, then program segment 1724 passes control to program segment 1710 and, conversely, if the answer of program segment is no, it passes control to program segment 1728.

Figure 26:
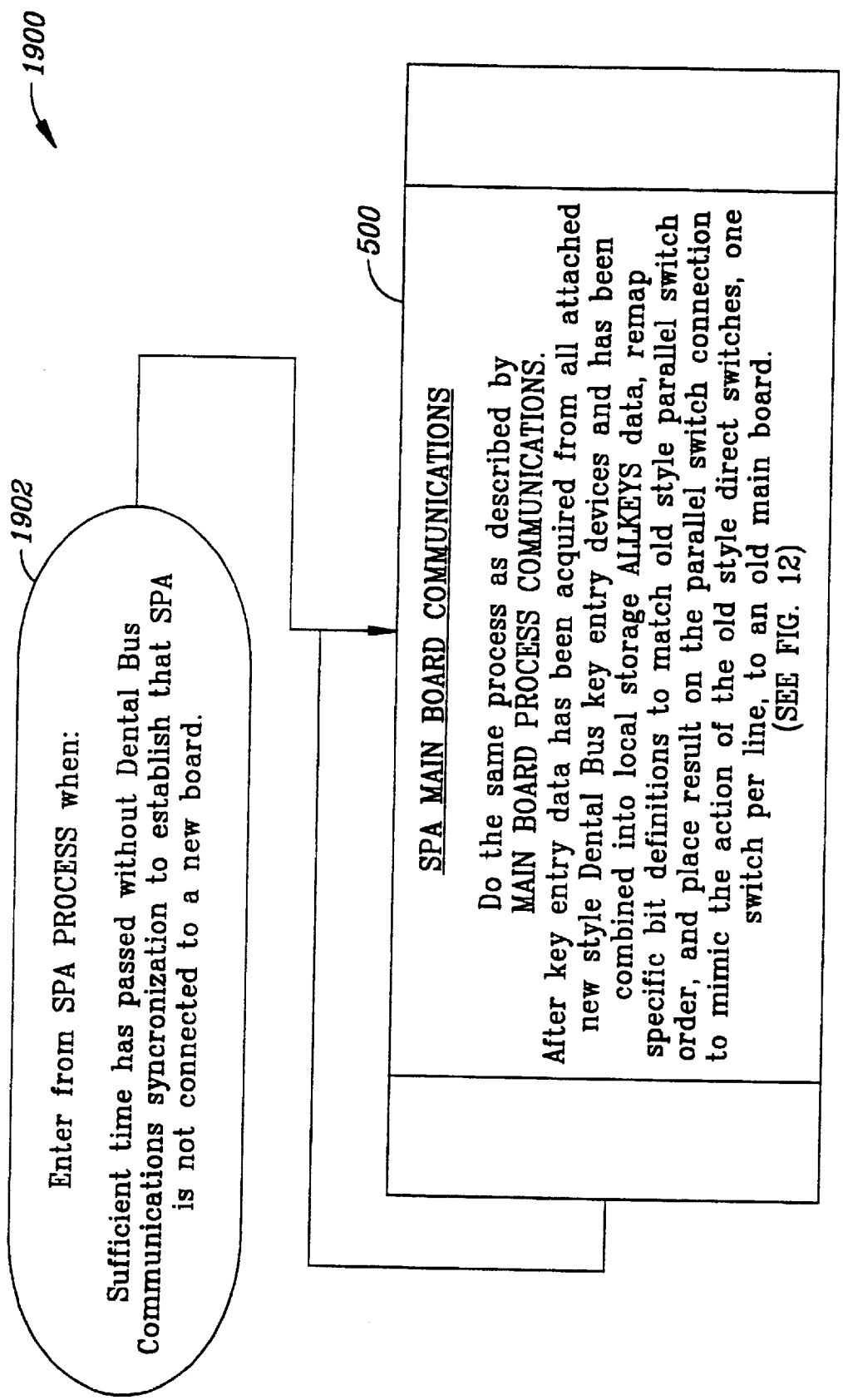
FIG. 26 illustrates the main features of the SPA process for an old board related to the present invention.

With reference back to program segment 1720, if a sync byte has not been received, program segment 1720 passes control to program segment 1726 which determines if a new board has been enabled, and if no, then passes control to program segment 1710 and, conversely, if yes, passes control to new board routine 1800 of FIG. 26.

With reference back to program segment 1728, if the second byte received by program segment 1724 was not a sync byte, program segment 1728 allows for the possible adjustment of the baud rate and may perform some maintenance task if desired and then passes control to program segment 1730 which, in turn, does nothing until 10 milliseconds has passed after the receipt of the second sync byte by program segment 1720, and then passes control to program segment 1734.

Program segment 1734 determines if fewer than 15 sync byte pairs have been received and if yes, then passes control to program segment 1710 and, conversely, if no passes control to program segment 1732 that enables a new board. Program segment 1732 passes control to new board routine 1800 which may be further described with reference to FIG. 25.

Figure 25:
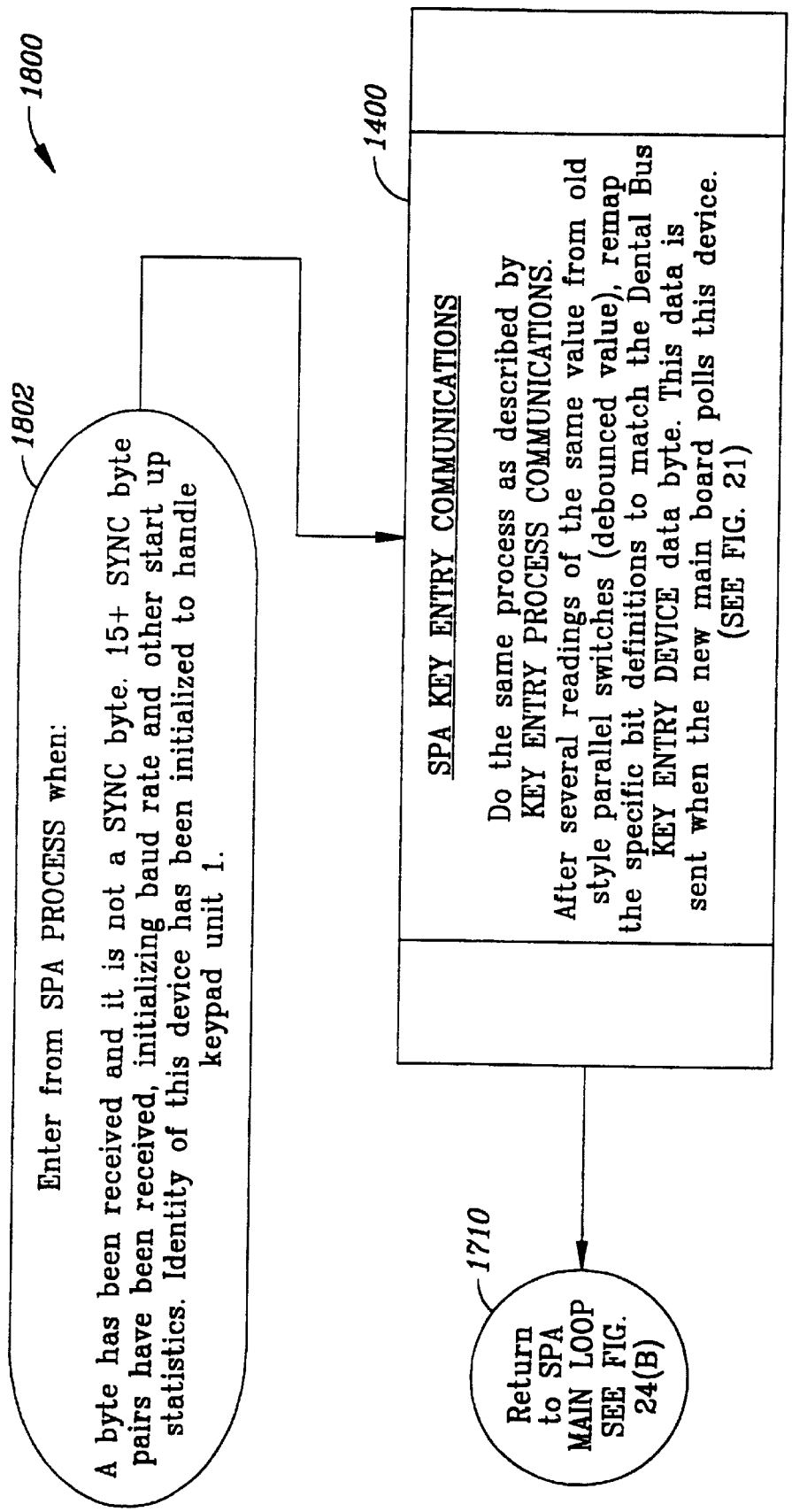
FIG. 25 illustrates the main features of the SPA process for a new board related to the present invention.

FIG. 25 illustrates the essential features of the serial parallel adapter process related to new board routine 1800 having an initial event 1802 which, in turn, has remarks stating that this process of FIG. 25 is entered into when a byte has been received and it is not a sync byte. More particularly, more than 15 sync byte pairs have been received, causing the initializing baud rate and start up statistics to be performed and the identity of the device as having been initialized to handle a keyboard pad unit 1. Program segment 1802 passes control to program routines 1400 which are the SPA keyboard entry communications which is the same as already described for the keyboard entry process communication routine 1400. After the routines 1400 have been completed control is passed to program segment 1710 of FIG. 24(B).

The serial parallel adapter process is also related to the use of old board which have SPA processor old board routine 1900 that may be further described with reference to FIG. 26. The SPA processor old board routine 1900 has an initial program segment 1902 which, in turn, has remarks therein that indicate that the SPA process old board routine 1900 is entered into when the SPA process determines that a sufficient time has passed without any serial communication bus synchronization so as to establish that a SPA is not connected to a new board. Program segment 1902 passes control to program segment 1500 which serves as the SPA main board communication and which is the main board process communication previously described with reference to FIG. 12.

It should now be appreciated that the practice of the present invention provides for operating routines that not only allow for the communications of the microprocessors 1, 2, 3 and 4 of the present invention, previously described, onto serial communication bus 40, but also provides for operating diagnostic routines that allows for the distributed intelligent system 10 of the present invention to be automatically serviced while at the same time preventing any undue error of the system 10 from causing any undue injury to any patient being treated by a dental person operating the system 10 of the present invention.

Furthermore, it should be appreciated that the present invention provides fault detection including detection of faults internal to the microprocessors of the present invention and the detection by one microprocessor of faults of a remote microprocessor. Further, the present invention provides fault tolerance in which errors from units are detected, but the information from other operating units is substituted therefor allowing the desired process to successfully continue. Moreover, the present invention provides the diagnostic monitor of FIG. 1 to supply external power under fault condition and to supply control commands for manufacturing and service purposes.

Although some of the variations and modifications of the present invention may be readily apparent to those skilled in the art, in light of the above teaching, it is, therefore, to be understood that, within the scope of the appended claims the invention may be other than and specifically described herein.

What we claim is:

1. A distributed intelligence system for controlling a plurality of groups of tools and equipment all used in dentistry, said system comprising:

(a) control circuitry generating first control signals applied to a first group of said tools and equipment and receiving first status signals from said first group of tools and equipment, said control circuitry including a first microcontroller containing predetermined routines for said generation of said first control signals and for being responsive to said first status signals, said control circuitry having protocol means for accommodating a serial communication bus;

(b) one or more foot switches for generating second control signals applied to a second group of said tools and equipment and receiving second status signals from said second group of tools and equipment, said one or more foot switches including a second microcontroller containing predetermined routines for said generation of said second control signals and for being responsive to said second status signals, said one or more switches having protocol means for accommodating a serial communication bus;

(c) control console generating third control signals applied to a third group of said tools and equipment and receiving third status signals from said third group of tools and equipment, said control console including a third microcontroller containing predetermined routines for said generation of said third control signals and for being responsive to said third status signals, said control console having protocol means for accommodating a serial communication bus;

(d) power supply means connected to said control circuitry, to said one or more foot switches and to said control console, said power supply means generating fourth control signals applied to a fourth group of said tools and equipment and receiving fourth status signals from said fourth group of tools and equipment, said power supply including a fourth microcontroller containing predetermined routines for said generation of said fourth control signals and for being responsive to said fourth status signals, said power supply having protocol means for accommodating a serial communication bus;

(e) cable means for interconnecting said protocol means of said control circuitry, said one or more foot switches, said control console and said power supply.

2. The distributed intelligence system according to claim 1, wherein said cable means comprises:

(a) a first conductor carrying power excitation;

(b) a second conductor carrying data; and (c) a third conductor serving as a return path for said power excitation and said data.

3. The distributed intelligence system according to claim 1, wherein each of said first, second, third and fourth microcontroller have a reduced instruction set computer (RISC) computer architecture.

4. The distributed intelligence system according to claim 1, wherein each of said first, second, third and fourth microcontrollers include diagnostic routines to respectively control the operation of said first, second, third and fourth groups of said tools and said equipment.

5. The distributed intelligence system according to claim 1, wherein said first, second, third and fourth microcontrollers communicate with each other over said serial communication bus.

6. The distributed intelligence system according to claim 2 further comprising a diagnostic monitor connected to said cable means and supplying said power excitation on said first conductor to said control circuitry, to said one or more foot switches, to said control console and to said power supply means, and also supplying said data on said second conductor to said control circuitry, to said one or more foot switches, to said control console and to said power supply means.

7. The distributed intelligence system according to claim 4, wherein said diagnostic routines include:
   (i) fault detection routines for detecting internal faults of each of said first, second, third and fourth microcontroller;
   (ii) fault detection routines wherein each of said first, second, third and fourth microcontrollers detects faults of each other;
   (iii) fault detection routines that allow for the detections of errors in a first unit connected to any of said first, second, third and fourth microcontrollers and then substitute a second unit for said first unit.

8. The distributed intelligence system according to claim 4, wherein said diagnostic routines include fault tolerant routines.

9. The distributed intelligence system according to claim 1, wherein each of said first, second, third and fourth microcontrollers include safety related routines to respectively control the operation of said first, second, and third and fourth groups of said tools and said equipment.

* * * * *